(12) United States Patent
Nagai et al.

(10) Patent No.: US 7,977,429 B2
(45) Date of Patent: Jul. 12, 2011

(54) POLYMERS AND USES THEREOF

(75) Inventors: Naoshi Nagai, Sodegaura (JP);
Masahiko Mitsuzuka, Sodegaura (JP);
Kazuoki Nakai, Sodegaura (JP);
Motoaki Isokawa, Sodegaura (JP);
Shiro Nakatsuka, Sodegaura (JP); Daiki Taneichi, Sodegaura (JP); Shirou Honma, Sodegaura (JP); Toshimitsu Narutaki, Sodegaura (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 1133 days.

(21) Appl. No.: 10/587,419

(22) PCT Filed: Jan. 20, 2005

(86) PCT No.: PCT/JP2005/000701
§ 371 (c)(1),
(2), (4) Date: Jul. 28, 2006

(87) PCT Pub. No.: WO2005/073282
PCT Pub. Date: Aug. 11, 2005

(65) Prior Publication Data
US 2007/0154431 A1   Jul. 5, 2007

(30) Foreign Application Priority Data

Jan. 30, 2004 (JP) ................................ 2004-022930
Jun. 8, 2004 (JP) ................................ 2004-170473

(51) Int. Cl.
*C08L 63/00* (2006.01)
(52) U.S. Cl. ........ 525/107; 525/165; 525/187; 525/408; 525/412; 525/438; 525/449; 525/476; 525/523; 525/533
(58) Field of Classification Search .................. 525/107, 525/165, 187, 408, 412, 438, 449, 476, 523, 525/533
See application file for complete search history.

(56) References Cited

U.S. PATENT DOCUMENTS

| | | | |
|---|---|---|---|
| 4,904,732 A | 2/1990 | Iwahara et al. | |
| 4,981,605 A | 1/1991 | Tsutsui et al. | |
| 5,008,338 A * | 4/1991 | Riddick et al. ................ | 525/177 |
| 5,252,677 A | 10/1993 | Tomita et al. | |
| 5,444,125 A | 8/1995 | Tomita et al. | |
| 5,811,483 A * | 9/1998 | Close ............ | 524/500 |
| 5,939,495 A | 8/1999 | Kioka et al. | |
| 5,962,572 A * | 10/1999 | Chen ............ | 524/474 |
| 6,084,030 A | 7/2000 | Janssen et al. | |
| 6,248,837 B1 | 6/2001 | Chung et al. | |
| 2003/0027955 A1 | 2/2003 | Ishii et al. | |

FOREIGN PATENT DOCUMENTS

| | | |
|---|---|---|
| EP | 0 329 891 A2 | 8/1989 |
| EP | 1 186 619 A2 | 3/2002 |
| EP | 1 408 058 A1 | 4/2004 |
| JP | 63-006003 A | 1/1988 |
| JP | 63-023904 | 2/1988 |
| JP | 63-101428 A | 5/1988 |
| JP | 01-217007 A | 8/1989 |
| JP | 04-055403 A | 2/1992 |
| JP | 4-328109 A | 11/1992 |
| JP | 5-125194 A | 5/1993 |
| JP | 7-78098 B2 | 8/1995 |
| JP | 07-780988 B2 | 8/1995 |
| JP | 07-091338 B2 | 10/1995 |
| JP | 7-91338 B2 | 10/1995 |
| JP | 7-103181 B2 | 11/1995 |
| JP | 07-103181 B2 | 11/1995 |
| JP | 09-003173 A | 1/1997 |
| JP | 10-036480 A | 2/1998 |
| JP | 10-077289 A | 3/1998 |
| JP | 2000-239312 A | 9/2000 |
| JP | 2001-002731 A | 1/2001 |
| JP | 2001-217007 A | 8/2001 |
| JP | 2002-226321 A | 8/2002 |
| JP | 2003-073412 A | 3/2003 |
| JP | 2003-292602 * | 10/2003 |
| JP | 2003-292602 A | 10/2003 |
| JP | 2003-292741 A | 10/2003 |
| JP | 2003-73412 A | 12/2003 |
| WO | WO 98/02472 A1 | 1/1998 |

OTHER PUBLICATIONS

Machine Translation of JP 2003-292602; T. Tsutomu and I. Toshio; Oct. 15, 2003; p. 1-12 [online], accessed via the Internet [retrieved on Feb. 19, 2010], URL:<http://www4.ipdl.inpit.go.jp/Tokujitu/PAJdetail.ipdl?N0000=60&N0120=01&N2001=2&N3001=2003-292602>.*
Supplementary European Search Report issued in corresponding European patent Application No. EP 05 70 3929 dated Mar. 29, 2010.
Office Action issued Apr. 27, 2010, in corresponding Japanese Application No.2005-020883.
Office Action issued Jan. 20, 2009, in corresponding Japanese Patent Application No. 2005-174628.

* cited by examiner

*Primary Examiner* — David Wu
*Assistant Examiner* — Robert Jones
(74) *Attorney, Agent, or Firm* — Buchanan Ingersoll & Rooney PC

(57) ABSTRACT

Polymers having polyolefin segments as the side chain, with a structural unit represented by the following Formula (1):

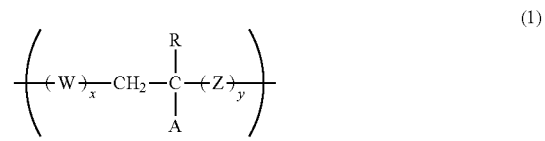

wherein A is an olefin polymer having a weight average molecular weight of 400 to 500,000; R is H, an alkyl group, or an aralkyl group; W and Z are each O, HN, or S; and x and y are each 0 or 1, with the proviso that at least one of them is 1. The polymer can be applied as an antistatic agent, a cosmetic additive, a releasing agent for toner, a pigment dispersant, a lubricant for vinyl chloride resins, a coating material, an emulsion composition and the like.

68 Claims, No Drawings

POLYMERS AND USES THEREOF

TECHNICAL FIELD

The present invention relates to novel polymers having polyolefins as the side chain, and uses thereof. More particularly, the invention relates to novel polymers having polyolefins with a weight average molecular weight of 400 to 500,000 as the side chain, and uses thereof.

BACKGROUND ART

Ethylenic polymers or α-olefin polymers have non-polar molecular structures and insufficient affinities to other substances, and thus it is being attempted to introduce various functional groups to the polymers. For example, the following polymers having functional groups introduced at the terminals have been reported.

(1) A polymer obtained by attaching unsaturated carboxylic acids having 3 to 10 carbon atoms, such as maleic acid, to the terminals of a liquid ethylenic polymer or a liquid α-olefin containing a double bond at one terminal, (for example, JP-B No. 7-78098), a polymer modified by epoxidation of the terminals (for example, JP-B No. 7-91338), a polymer modified by hydroxylation of the terminals (for example, JP-B No. 7-103181);

(2) A polymer resulting from epoxidation, hydroxylation or sulfonation of the terminals of a syndiotactic α-olefin polymer containing a double bond at one terminal (for example, U.S. Pat. No. 5,252,677);

(3) A polymer resulting from hydroxylation-, epoxidation, maleination, sulfonation, silylation or halogenation of a double bond at one end of an ethylenic polymer (for example, JP-A No. 2001-2731 and JP-A No. 2003-73412); and (4) A halogen-terminated polymer, a carboxyl-terminated polymer, an amino-terminated polymer or the like, derived from a polymer having hydroxyl at one terminal that is obtained by oxidation of a low molecular weight polyethylene (for example, JP-A No. 1-217007).

Among these reported examples, the polymers of groups (1) to (3) are polymers obtained by modification of polymers having double bonds at one terminal. These polymers can be used in various applications, but their application fields are limited because the modification methods are limited, the contents of functional groups may be small depending on the modification methods, and the like.

The polymers of group (4) are polymers obtained by modification of single-terminal hydroxylation products of low molecular weight polyethylene, and for example, those prepared by chemical modification, such as Unilin (registered trademark), which are primary alcohols resulting from 80 to 85% modification of the terminals of polyethylene having up to 50 carbon atoms on the average, are known. However, their application fields are limited because the molecular weight of the starting material Unilin is limited to relatively low molecular weights, the type of polymer is limited to polyethylene, and the like.

Furthermore, it is known that highly functional, controlled polymers such as comb-like polymers can be obtained by copolymerizing polymers or oligomers that are polymerizable due to the presence of the introduced functional groups, as generally referred to as macromonomers, with other monomers. Many examples of the polymers having polyolefinic macromonomers as the component are known, but polyolefinic macromonomers having polymerizable unsaturated groups have smaller amounts of polar groups and are difficult to be used for the purpose of modifying polyolefins. Other known polymers having polymerizable functional groups include a polymer having hydroxyl groups at the terminals (JP-A No. 9-3173), and a polymer having epoxy groups within the polyolefin chains (JP-A No. 4-55403); however, since the former is rendered polymerizable by further reacting with a tetracarboxylic acid, the polymers obtained by using this macromonomer have limited structures. The latter has a plurality of alkylene oxides having a statistic distribution in one polyolefin chain, and thus there occur problems such as that crosslinking takes place during the reaction of alkylene oxide. Therefore, it is difficult to obtain a polymer having a structure comprising a controlled polyolefin skeleton and a skeleton containing polar groups, by effectively utilizing the latter polymer as the macromonomer.

[Patent Document 1] JP-B No. 7-78098
[Patent Document 2] JP-B No. 7-91338
[Patent Document 3] JP-B No. 7-103181
[Patent Document 4] U.S. Pat. No. 5,252,677
[Patent Document 5] JP-A No. 2001-2731
[Patent Document 6] JP-A No. 2003-73412
[Patent Document 7] JP-A No. 1-217007
[Patent Document 8] JP-A No. 9-3173
[Patent Document 9] JP-A No. 4-55403

DISCLOSURE OF THE INVENTION

Problems to be Solved by the Invention

The present invention is to provide novel polymers containing polyolefin segments and having controlled structures, and to disclose the applicability of the polymers having such controlled structures to a variety of uses.

The invention is to provide a novel polymer as described, containing a structural unit having polyolefin as the side chain and having oxygen atoms in the main chain, and to provide a novel material containing this polymer as an application of the polymer.

The invention is to provide a novel polymer as described above, which is a novel polyolefin-containing polysiloxane having a siloxane skeleton at the polymer terminals, and a method for preparation thereof, and also to provide a cosmetic material containing the polyolefin-containing polysiloxane as an application of the polymer.

The invention is to provide a novel polymer as described above, having specific functional groups at the positions of two carbon atoms adjacent to the polymer terminal, and to provide a novel material containing this polymer.

Means to Solve the Problems

According to the invention, a novel polymer contains polyolefin segments having at least a structural unit represented by the following Formula (1):

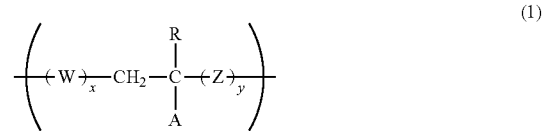

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; W and Z are each independently an oxygen atom, an NH group or a sulfur atom; and x and y are each 0 or 1, with the proviso that at least one of them is 1.

A suitable example of the polymer having the structural unit represented by the above Formula (1) is a polymer having a structural unit represented by the following Formula (2) (Polymer (I)):

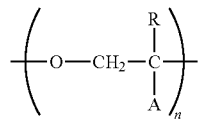
(2)

wherein A and R are as defined in Formula (1), and n is an integer of 1 or greater.

Another suitable example of the polymer having the structural unit represented by the above Formula (1) is a polysiloxane compound containing the structural unit represented by the above Formula (2) (Polymer (II)).

Further suitable example of the polymer having the structural unit represented by the above Formula (1) is a polymer represented by the following Formula (14) (Polymer (III)):

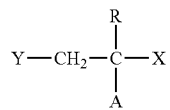
(14)

wherein A and R are as defined in the above Formula (1); X and Y are such that one of them is a hydroxyl group, a polyalkylene glycol group or an acyloxy group, and the other is a group represented by any of the following Formula (15), Formula (16) and Formula (17), a cyano group, a carboxyl group, an ester group or an amide group; and X and Y may be bonded to each other to form a 5-membered ring;

-E-R$^7$ (15)

wherein E is an oxygen atom or a sulfur atom; and R$^7$ is a hydrogen atom, a hydrocarbon group, an acyl group or a polyalkylene glycol group;

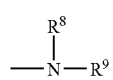
(16)

wherein R$^8$ and R$^9$, which may be identical or different, are each a hydrogen atom, a hydrocarbon group, an acyl group or a polyalkylene glycol group; and

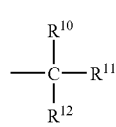
(17)

wherein R$^{10}$ to R$^{12}$, which may be identical or different, are each a hydrogen atom, a hydrocarbon group, an acyl group, a cyano group, a carboxyl group, an ester group or an amide group.

Examples of the novel polymers provided by the invention will be specifically described in the following detailed description.

The novel polymers provided by the invention exhibit specific properties as polymers themselves as well as in compositions with other materials. The polymers are also very useful since suitable uses are provided in accordance with the properties. Such uses will be also clarified in the following description.

Effect of the Invention

According to the invention, various novel polymers containing polyolefin segments can be provided.

The polyolefinic macromonomers constituting the basis of the polymers of the invention are advantageous in economic aspect since expensive starting materials are not used for the monomer.

Further, according to the invention, a novel polymer containing a structural unit having polyolefin as the side chain and having oxygen atoms in the main chain can be provided, and as applications of this polymer, there can be also provided an antistatic agent, an adhesive, a coating composition, molded articles and the like, which are novel materials containing the polymer.

The polyolefin-containing polysiloxane provided by the invention has, for example, improved make-up maintenance and compatibility with oily ingredients as compared with conventional materials, and an excellent sense of use as a cosmetic material, thus being useful particularly as an additive for the cosmetic material for makeup.

Furthermore, according to the invention, a novel polymer having specific functional groups at two positions adjacent to the polymer terminal can be provided. This polymer also does not use expensive starting materials for the monomer, and thus is economically advantageous.

The above polymers can be used to provide materials appropriate for a releasing agent for toner, a pigment dispersing agent, a lubricant for vinyl chloride resins, an emulsion composition and the like.

BEST MODE FOR CARRYING OUT THE INVENTION

Hereinafter, embodiments of the present invention will be described.

The polymer of the invention has at least a structural unit represented by the following Formula (1):

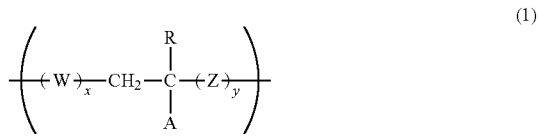
(1)

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; W and Z are each independently an oxygen atom, an NH group or a sulfur atom; and x and y are each 0 or 1, with the proviso that at least one of them is 1.

Examples of the olefin having 2 to 20 carbon atoms include α-olefins such as ethylene, propylene, 1-butene and 1-hexene, and the polymer may be a homopolymer or copolymer of these olefins, or even a product of copolymerization with other polymerizable unsaturated compounds within the scope of not impairing the characteristics. Among these, ethylene, propylene and 1-butene are particularly preferred.

In Formula (1), the group represented by A is preferably a group formed by homopolymerization of ethylene, copolymerization of ethylene with an α-olefin having 3 to 20 carbon atoms, or homopolymerization of an α-olefin having 3 to 20 carbon atoms.

The weight average molecular weight (Mw) of the group represented by A as measured by gel permeation chromatography (hereinafter, abbreviated to GPC) is 400 to 500,000, preferably 800 to 200,000, and more preferably 1,000 to 100,000. The weight average molecular weight (Mw) as used herein is a value calibrated with polystyrene standards.

The ratio of the weight average molecular weight (Mw) and the number average molecular weight (Mn), both measured by GPC, of the group represented by A in Formula (1), that is, the molecular weight distribution (Mw/Mn), is not particularly limited and may range from 1.0 to a few tens; however, in view of uniformity of the properties, the ratio is preferably 4.0 or less, particularly preferably 3.0 or less.

The weight average molecular weight (Mw) and molecular weight distribution (Mw/Mn) of the group represented by A can be measured using, for example, a GPC-150 available from Millipore Corp. under the following conditions.

Separating column: TSK GNH HT (column size: diameter 7.5 mm, length: 300 mm)
Column temperature: 140° C.
Mobile phase: o-dichlorobenzene (Wako Pure Chemical Industries, Ltd.)
Antioxidant: 0.025% by weight of butylhydroxytoluene (Takeda Pharmaceutical Co., Ltd.)
Flow rate: 1.0 ml/min
Sample concentration: 0.1% by weight
Sample injection amount: 500 µl
Detector: differential refractometer R is hydrogen or a hydrocarbon group having 1 to 18 carbon atoms, which is a substituent attached to a double bond of the olefin constituting A, and may be exemplified by hydrogen, a methyl group, an ethyl group, a propyl group or the like.

Polymer (I)

Among the polymers containing the structural unit represented by the Formula (1) above, one preferred polymer is a polymer containing the structural unit represented by the following Formula (2) (hereinafter, referred to as Polymer (I)):

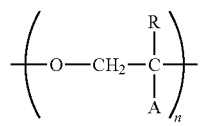
(2)

wherein A and R are as defined in Formula (1), and n is an integer of 1 or greater.

In Polymer (I) of the invention, the content of the structural unit represented by Formula (2) is not limited as long as the polymer contains the structural unit represented by Formula (2), and the preferred range varies depending on the use of the polymer. When the polymer is used as an antistatic agent, the content is generally 1 to 99% by mole.

The same applies when the polymer is a polymer having hydroxyl groups at both terminals.

A preferred embodiment of Polymer (I) of the invention is a polymer of the above Formula (2) having hydroxyl group at both terminals (Polymer I-a).

Polymer (I) of the invention is a polymer having the structural unit of Formula (2), which can be prepared through a reaction with a compound reactive to a hydroxyl group or an epoxy group. For example, the polymer has an ether bond, an ester bond, a urethane bond, an amide bond or a carbonate bond. Further specific examples also include block copolymers resulted from a reaction with siloxane.

These polymers can be obtained by ring-opening polymerization or copolymerization of an epoxy compound obtained by epoxidating a polyolefin having an unsaturated group at one terminal, as described later. If water or a diol is used as the initiator, a polymer having hydroxyl groups at both terminals can be obtained.

An embodiment in which Polymer (I) is a Polymer (I-b) having the structural unit represented by the above Formula (2) and a structural unit represented by the following Formula (4) as the repeating units, will be described. The repeating units are repeating units of (2) and (4), and the repeating pattern may be any of block, alternating and random patterns.

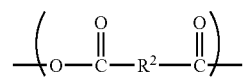
(4)

wherein $R^2$ is a divalent hydrocarbon group having 1 to 20 carbon atoms which may have a heteroatom.

In Formula (4), the hydrocarbon group of $R^2$ is not particularly limited, but examples thereof include an alkylene group such as a methylene group and an ethylene group; a cycloalkylene group such as a cyclohexylene group; an arylene group such as a phenylene group or a xylylene group; and the above-mentioned groups having part of their hydrogen atoms substituted with hydrocarbon groups, heteroatoms or hydrocarbon groups substituted with heteroatoms. The polymer can be prepared, for example, by condensing a commercially available dicarboxylic acid having the corresponding structure that is employed as a monomer unit, with a diol having the structural unit of Formula (2). Here, other polymerization component, for example, a hydroxycarboxylic acid, other diol, a dicarboxylic acid of other structure or the like, can be also copolymerized.

The weight average molecular weight of Polymer (I) is not particularly limited, and the preferred range varies depending on the use. But, the weight average molecular weight is generally 1,000 to 1,000,000, and when the polymer is used as a molding material, the value is generally about 10,000 to 500,000.

Another embodiment of the polymer of the invention is a Polymer (I-c) having the structural unit represented by the above Formula (2) and a structural unit represented by the following Formula (5) as the repeating units. The repeating units are repeating units of (2) and (5), and the repeating pattern may be any of block, alternating and random patterns.

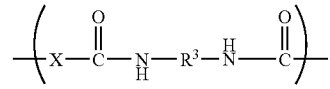
(5)

wherein X is an oxygen atom or an NH group, and $R^3$ is a divalent hydrocarbon group having 1 to 20 carbon atoms which may contain a heteroatom.

In Formula (5), the hydrocarbon group of $R^3$ may be exemplified by those listed as the hydrocarbon group of $R^2$ of the above-described Formula (4), and the polymer can be prepared by condensing a commercially available diisocyanate as a monomer unit, with a diol having the structural unit of Formula (2). Here, other polymerization component, for example, other diol, a diisocyanate of other structure or the like, can be also copolymerized.

The weight average molecular weight of the polymer is not particularly limited, and the preferred range varies depending on the use. But, the weight average molecular weight is generally 1,000 to 1,000,000, and when the polymer is used as a molding material, the value is generally about 10,000 to 500,000.

Further embodiment of the polymer of the invention is a Polymer (I-d) having the structural unit represented by the above Formula (2) and a structural unit represented by the following Formula (6) as the repeating units.

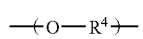  (6)

wherein $R^4$ is a divalent hydrocarbon group having 1 to 20 carbon atoms which may contain a heteroatom.

In Formula (6), the hydrocarbon group of $R^4$ is not particularly limited, but examples thereof include an alkylene group such as a methylene group, an ethylene group, a propylene group, a butylene group and a hexylene group; a cycloalkylene group such as a cyclohexylene group; an arylene group such as a phenylene group, a xylylene group and a biphenylene group; and the above-mentioned groups having part of their hydrogen atoms substituted with hydrocarbon groups, heteroatoms or hydrocarbon groups substituted with heteroatoms. Preferred ones are an ethylene group or a propylene group formed by polymerizing an alkylene oxide such as commercially available ethylene oxide or propylene oxide, and a methylene group which is a polymer of formaldehyde. The hydrocarbon group can be prepared by ring-opening polymerization of an alkylene oxide with an epoxy compound obtained by epoxidating a polyolefin having an unsaturated group at one terminal as described later, and the hydrocarbon group may be of a random copolymer structure resulting from simultaneous copolymerization, or a block copolymer structure resulting from sequential polymerization.

As is clear from the purpose of the invention, the ratio of the two components may be any ratio, as long as both the components are contained.

The total weight average molecular weight is not limited, but in general, the weight average molecular weight is generally 1,000 to 1,000,000, and is about 1,000 to 100,000 for the use as a compatibilizing agent, an antistatic agent or the like.

Polymer (I) of the invention can be prepared by the following method.

First, among the target polymers, a polyolefin represented by the following Formula (7), having a double bond at one terminal, is prepared as the monomer corresponding to the structure represented by Formula (2):

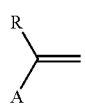  (7)

wherein A and R are as defined in Formula (2); A is a polymer of an olefin having 2 to 20 carbon atoms, whose weight average molecular weight is 400 to 500,000; and R is a hydrogen atom, or an alkyl group or an aralkyl group having 1 to 18 carbon atoms.

This polyolefin can be prepared by the following methods:

(1) A polymerization method of using a transition metal compound having a salicylaldimine ligand as described in JP-A No. 2000-239312, JP-A No. 2001-2731, JP-A No. 2003-73412 and the like, as the polymerization catalyst;

(2) A polymerization method of using a titanium-based catalyst comprising a titanium compound and an organic aluminum compound;

(3) A polymerization method of using a vanadium-based catalyst comprising a vanadium compound and an organic aluminum compound; and (4) A polymerization method of using a metallocene type catalyst comprising a metallocene compound such as zirconocene and an organic aluminum oxy compound (aluminoxane).

Among these methods (1) to (4), particularly according to method (1), the above-described polyolefin can be prepared with good yield. In method (1), a polyolefin having a double bond at one terminal can be prepared by polymerizing or copolymerizing the above-mentioned olefin in the presence of a transition metal compound having a salicylaldimine ligand.

The polymerization of olefin according to method (1) can be carried out by either a liquid phase polymerization method such as solution polymerization or suspension polymerization, or a gas phase polymerization method. Detailed conditions and the like are already known, and the polyolefin can be prepared by referring to the above-described patent documents.

The proportion of the vinyl or vinylidene type double bond, as measured by $^1$H-NMR, in the low molecular weight ethylenic polymer of the invention (hereinafter, this proportion is referred to as the "content of single terminal vinyl group") is 50% or more, more preferably 70% or more, and even more preferably 80% or more, of the total single terminals. The measurement by $^1$H-NMR was carried out at 120° C. after completely dissolving the polymer in deuterated 1,1,2,2-tetrachloroethane, which functions both as the lock solvent and the solvent, in a sample tube for measurement. For the chemical shift, the peak of deuterated 1,1,2,2-tetrachloroethane was set at 5.92 ppm, and the chemical shift values of other peaks were determined on this basis.

The content of single terminal vinyl group in a low molecular weight polymer comprising ethylene only is determined by $^1$H-NMR. The peaks (A) of the three protons for saturated terminal methyl group are observed at 0.65 to 0.85 ppm, and the peaks (B) of the three protons for the vinyl group are observed at 4.70 to 5.00 ppm and 5.50 to 5.80 ppm. When the peak areas of peak (A) and peak (B) are taken as $S_A$ and $S_B$, respectively, the content of double bond (U %) is calculated by the following formula:

$$U(\%) = S_B \times 200/(S_A + S_B).$$

The molecular weight of the polyolefin obtained according to method (1) can be adjusted by adding hydrogen to the polymerization system, by varying the polymerization temperature, or by changing the kind of catalyst used.

Subsequently, the polyolefin is epoxified, that is, the double bonds at the terminals of the polyolefin are oxidized, to obtain a polymer containing a terminal epoxy group as represented by the following Formula (8):

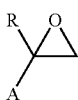
 (8)

wherein A and R are identical with the groups defined in Formula (7).

The weight average molecular weight of the group represented by A can be determined as the value obtained by deducting the molecular weight of the group represented by R and the molecular weight 42 of an epoxy group from the weight average molecular weight of the epoxy-terminated polymer.

The method for epoxidating a polyolefin is not particularly limited, but the following methods can be mentioned:

(1) Oxidation by peracid such as performic acid, peracetic acid or perbenzoic acid;

(2) Oxidation by titanosilicate and hydrogen peroxide;

(3) Oxidation by a rhenium oxide catalyst such as methyltrioxorhenium, and hydrogen peroxide;

(4) Oxidation by a porphyrin complex catalyst such as manganese porphyrin or iron porphyrin, and hydrogen peroxide or hypochlorite;

(5) Oxidation by a salen complex such as manganese salen, and hydrogen peroxide or hypochlorite;

(6) Oxidation by a TACN complex such as manganese triazacyclononane (TACN) complex, and hydrogen peroxide; and (7) Oxidation by hydrogen peroxide in the presence of a Group VI transition metal catalyst such as a tungsten compound, and a phase transfer catalyst.

Among the methods (1) to (7), methods (1) and (7) are particularly preferred in view of activity.

The epoxy content in the total single terminals of the epoxy-terminated polymer is determined by $^1$H-NMR. For example, in the case of a polymer obtained by epoxidation of a double bond-terminated polymer comprising ethylene only, the peaks (C) of the three protons for saturated terminal methyl group are observed at 0.65 to 0.90 ppm, and the peaks (D) of the three protons corresponding to the epoxy group are observed at 2.30 to 2.40 ppm, 2.60 to 2.70 ppm, and 2.80 to 2.90 ppm for each proton. When the epoxy modification is not sufficient, the peaks (E) for the three-proton fraction at the terminal double bond are observed at 4.70 to 5.00 ppm for two protons, and 5.50 to 5.80 ppm for one proton. When the respective peak areas of peaks (C), (D) and (E) are taken as $S_C$, $S_D$ and $S_E$, respectively, the epoxy group content (Ep(%)) is calculated by the following formula:

$$Ep(\%)=S_D \times 200/(S_C+S_D+S_E).$$

Further, for example, an epoxy-terminated polymer having a low molecular weight Mw of about 400 to 600 that can be used is VIKOLOX (registered trademark, Arkema Inc.).

A polymer having the structural unit of Formula (1) can be produced by ring-opening polymerization of the epoxy-terminated polymer obtained by the above method. For the catalyst, polymerization conditions and the like, known ring-opening polymerization methods for alkylene oxide can be used, and for example, examples of obtaining polyol by polymerizing various monomers are disclosed in Otsu, Takayuki, "Revised Polymer Synthesis Chemistry," Kabushiki Kaisha Kagaku Doujin, January 1971, p. 172-180. The catalyst used in the ring-opening polymerization may include, as described in the above literature, Lewis acids such as $AlCl_3$, $SbCl_5$, $BF_3$, and $FeCl_3$ exclusively for cationic polymerization; hydroxides or alkoxides of alkali metals, amines and phosphazene catalysts exclusively for anionic polymerization; and oxides, carbonates and alkoxides of alkaline earth metals, or alkoxides of Al, Zn, Fe and the like exclusively for coordinate anionic polymerization. Here, the phosphazene catalysts that can be used may be exemplified by those compounds described in JP-A No. 10-77289, specifically the products resulting from changing the anion of commercially available tetrakis[tris(dimethylamino)phosphoranilidenamino]phosphonium chloride into an alkoxy anion by using an alkali metal alkoxide.

In the presence of the above-described catalyst, a homopolymer of the epoxy-terminated polymer can be obtained by ring-opening polymerization of only an epoxy-terminated polymer using an active hydrogen compound such as water, amine, diol or polyol as the initiator, and a copolymer can be obtained by ring-opening polymerization of the epoxy-terminated polymer with other alkylene oxides.

For the reaction solvent, those inert to epoxy-terminated polymers and alkylene oxides can be used, and mention may be made of aliphatic hydrocarbons such as n-hexane and the like, alicyclic hydrocarbons such as cyclohexane and the like, aromatic hydrocarbons such as toluene, xylene and the like, ethers such as dioxane and the like, halogenated hydrocarbons such as dichlorobenzene and the like.

The amount of the catalyst to be used is such that, for the catalysts other than phosphazene catalysts, the amount is preferably in the range of 0.05 to 5 moles, and more preferably in the range of 0.1 to 3 moles, based on 1 mole of the epoxy-terminated polymer as the starting material. The amount of phosphazene catalyst to be used is preferably $1 \times 10^{-4}$ to $5 \times 10^{-1}$ moles, and more preferably $5 \times 10^{-4}$ to $1 \times 10^{-1}$ moles, based on 1 mole of the epoxy-terminated polymer, in the aspects of rate of polymerization, economic efficiency and the like.

The reaction temperature is usually 25 to 150° C., and preferably 50 to 110° C., and although the reaction time varies depending on the reaction conditions such as the amount of catalyst, reaction temperature, reactivity of olefins and the like, it is usually a few minutes to 50 hours.

When water or diol is used as the initiator, a polymer having hydroxyl groups at both terminals (I-a) can be obtained. Further, when a polyether polyol having a specific molecular weight obtained by preliminarily polymerizing alkylene oxide is used as the initiator, it becomes possible to introduce a hydrophilic unit having a predetermined molecular weight, and production of a block copolymer having hydroxyl groups at both terminals, which has desired properties, is facilitated.

For the polyether polyol, mention may be made of polyethylene glycol, polypropylene glycol, polytetraethylene glycol and the like, and among these, polyethylene glycol and polypropylene glycol are preferred.

The Polymer (I-b) having the structural unit represented by the above Formula (2) and the structural unit represented by the above Formula (4) as repeating units can be produced by the following method.

(1) Reaction between the polymer having hydroxyl groups at both terminals (I-a), and a dicarboxylic acid corresponding to Formula (4).

(2) Reaction between the epoxy-terminated polymer and a dicarboxylic acid corresponding to Formula (4).

(3) Reaction between a polyester polyol obtained by condensation reaction between a dicarboxylic acid corresponding to Formula (4) and a diol, and an epoxy-terminated polymer.

Here, general diols may be co-existent in the reactions of (1) and (2).

The dicarboxylic acid is as described above, and more specifically, various commercially available dicarboxylic acids such as oxalic acid, maleic acid, phthalic acid, isophthalic acid, terephthalic acid and the like can be used without modification.

For the diols, mention may be made of aliphatic diols such as ethylene glycol, propylene glycol, butanediol and the like, and aromatic diols such as biphenol, bisphenol A and the like. Optionally, triols such as glycerin and the like also can be used. These diols can be obtained individually or in combination of two or more species.

The method for forming an ester bonding from an alcohol and a carboxylic acid is well known, and mention may be made of a method of removing water in the presence of dehydration catalyst, a method of changing the carboxylic acid into an anhydride or an acid chloride and then allowing the product to react in the presence of a base such as amine, or the like, without being particularly limited. For the method of conducting a direct reaction between an epoxide and a carboxylic acid, known methods also can be disclosed such as a method of carrying out the reaction in the presence of an alkali metal salt of the carboxylic acid or the like.

The Polymer (I-c) having the structural unit represented by the above Formula (2) and the structural unit represented by Formula (5) as repeating units can be produced by the following method.

(1) Reaction between the above-described epoxy-terminated polymer and a diisocyanate corresponding to Formula (5).

(2) Reaction between the above-described Polymer (I-a) and a diisocyanate corresponding to Formula (5).

(3) Reaction between the above-described Polymer (1-b) and a diisocyanate corresponding to Formula (5).

As the diisocyanate usable for the production of Polymer (I-c), for example, among those disclosed in Matsudaira, Nobutaka et al., ed., "Polyurethane", Maki-Shoten Publishing Co. (1964), pp. 13-18, those having 3 to 23 carbon atoms can be used. Specifically, hexamethylene diisocyanate, xylylene diisocyanate, toluene diisocyanate, diphenylmethane diisocyanate and the like can be used, and these may be used individually or in combination of a plurality thereof.

Moreover, it is also possible to use a small amount of polyisocyanate such as monoisocyanate or triisocyanate in combination.

For the method of reacting the two substances, there are known a number of methods as disclosed in the above-mentioned literature, and known methods such as a method of heating in the presence of salt of tin, amine or the like can be employed.

The Polymer (I-d) having the structural unit represented by the above Formula (2) and the structural unit represented by Formula (6) as repeating units can be produced by various methods as described above, but it is common to carry out polymerization in the same manner as in the method of polymerizing a corresponding epoxide and the above-described epoxy-terminated polymer.

Polymer (II)

Among the polymers containing the structural unit represented by the above Formula (1), another preferred polymer is a polysiloxane comprising a polymer containing the structural unit represented by Formula (2) (hereinafter, referred to as Polymer (II)).

As a preferred example of the Polymer (II) of the invention, a polysiloxane compound represented by the following Formula (9) can be mentioned:

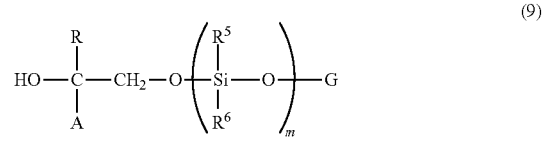

wherein A and R are as defined above in Formula (1); $R^5$ and $R^6$, which may be identical or different, are respectively a hydrogen atom, an alkyl group, a cycloalkyl group, an aryl group, or an alkenyl group, all having 1 to 10 carbon atoms; and m is a number from 1 to 3,000.

G is a hydrogen atom, an alkyl group having 1 to 5 carbon atoms, an alkali metal, or a group represented by the following Formula (10):

wherein A and R are as defined above in Formula (1).

The polyolefin-comprising polysiloxane of the invention can be prepared by reacting an epoxy-terminated polymer represented by the above Formula (8) or an α,β-dihydroxy polymer represented by the following Formula (11), with a chain-like polysiloxane represented by the following Formula (12) or a cyclic polysiloxane represented by the following Formula (13) in the presence of an acid or basic catalyst:

wherein A and R are as defined above in Formula (1);

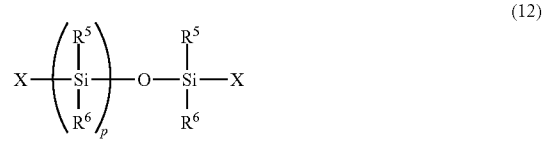

in which Formulas (12) and (13), $R^5$ and $R^6$ are as defined above in Formula (9). In Formula (12), X is a hydroxyl group, an alkoxy group having 1 to 5 carbon atoms or a halogen atom; and p is a number from 0 to 3000. In Formula (13), Y represents direct bonding to the cyclic structure; and q is an integer from 1 to 50.

The α,β-dihydroxy polymer represented by Formula (11) can be obtained by reacting an epoxy-terminated polymer and water.

For the alkyl group, cycloalkyl group and alkenyl group having 1 to 10 carbon atoms for $R^5$ and $R^6$ in the Formulas (9),

(12) and (13), mention may be made of a methyl group, an ethyl group, a propyl group, a vinyl group, a butyl group, a pentyl group, a hexyl group, a cyclohexyl group and the like. For the aryl group having 1 to 10 carbon atoms for $R^5$ and $R^6$, mention may be made of a phenyl group and a naphthyl group. Among these, a methyl group and a phenyl group are particularly preferred.

In Formula (9), G, the alkyl group having 1 to 5 carbon atoms may be exemplified by a methyl group, an ethyl group, a propyl group, a butyl group or the like. The alkali metal may be exemplified by lithium, sodium, potassium, rubidium or cesium.

For the alkoxy group having 1 to 5 carbon atoms for X in Formula (12), mention may be made of a methoxy group, an ethoxy group, a propoxy group, a butoxy group, a pentyloxy group and the like. For the halogen atom for X, mention may be made of a fluorine atom, a chlorine atom, a bromine atom, an iodine atom or the like.

<Process of Producing Polyolefin-Containing Polysiloxane>

A polyolefin-containing polysiloxane can be obtained by reacting an epoxy-terminated polymer or an α,β-dihydroxy polymer as the starting material, with the siloxane represented by the above Formula (12) or (13) in the presence of an acid or base catalyst.

Examples of the acid catalyst include mineral acids such as hydrochloric acid, sulfuric acid, phosphoric acid and the like; sulfonic acids such as p-toluenesulfonic acid and the like; solid acids such as Amberlist-15 (registered trademark); Lewis acids such as boron trifluoride ether complex, boron trichloride, boron tribromide, aluminum trichloride, aluminum tribromide, tin tetrachloride, zinc dichloride and the like.

Examples of the base catalyst include hydroxides, carbonates and hydrogen carbonates of alkali metals such as lithium, sodium, potassium, cesium and the like; hydroxides, carbonates and hydrogen carbonates of alkaline earth metals such as magnesium, calcium and the like; organic amines such as pyridine, 4-dimethylaminopyridine, triethylamine and the like; weakly basic ion exchange resins such as Amberlist-21 (registered trademark), Amberlist-93 (registered trademark) and the like; and the like.

The amount of the acid or base catalyst to be used is preferably 0.001- to 10-folds by weight, more preferably 0.01- to 5-folds by weight, and most preferably 0.05- to 2-folds by weight, with respect to the epoxy-terminated polymer or the α,β-dihydroxy polymer. Such acid or base catalyst may be used individually or in combination of two or more species.

For the reaction solvent, those inert to the epoxy-terminated polymer or the α,β-dihydroxy polymer as the starting material can be used, and examples thereof include aliphatic hydrocarbons such as n-hexane and the like; alicyclic hydrocarbons such as cyclohexane and the like; aromatic hydrocarbons such as toluene, xylene and the like; esters such as ethyl acetate and the like; ketones such as acetone, methyl ethyl ketone, methyl isobutyl ketone, diethyl ketone, methyl propyl ketone and the like; ethers such as tetrahydrofuran, 1,4-dioxane and the like, halogenated hydrocarbons such as chloroform, dichloroethane, trichloroethane, dichlorobenzene and the like; and the like. As far as the starting material epoxy-terminated polymer is insoluble to the solvent, aromatic hydrocarbon such as toluene, xylene and the like are preferred. The amount of the solvent to be used depends on the solubility of the starting material, but the amount is preferably 0.8- to 100-folds by weight, more preferably 1- to 50-folds by weight, and even more preferably 2- to 20-folds by weight, with respect to the epoxy-terminated polymer of the starting material.

Examples of the chain-like polysiloxane of Formula (12) include 1,1,3,3-tetramethyldisiloxane, 1,1,3,3-tetraisopropyldisiloxane, 1,1,3,3-tetramethyl-1,3-dichlorodisiloxane, hexamethyldisiloxane, 1,5-dichlorohexamethyltrisiloxane, octamethyltetrasiloxane, 1,7-dichlorooctamethyltetrasiloxane, 1,3-dichloro-1,3-diphenyldisiloxane, 1,3-dichloro-1,3-dimethyl-1,3-diphenyldisiloxane, 1,3-dimethyl-1,3-diphenyldisiloxane, 1,3-diphenyltetramethoxydisiloxane, 1,1,3,3,5,5-hexamethyldiethoxysiloxane, 1,3-dihydroxytetramethyldisiloxane, 1,7-dimethoxyoctamethyltetrasiloxane, 1,9-dichlorodecamethylpentasiloxane, 1,3-dimethoxytetramethyldisiloxane, 1,3-diacetoxytetramethyldisiloxane, bis(trimethylsiloxy)dichlorosilane, tetramethyldisiloxane and the like.

Examples of the cyclic polysiloxane of Formula (13) include decamethylcyclopentasiloxane, hexamethylcyclotrisiloxane, octamethylcyclotetrasiloxane, 1,3,5,7-tetramethylcyclotetrasiloxane, octaphenylcyclotetrasiloxane, hexaethylcyclotrisiloxane, 1,3,5,7-tetramethyl-1,3,5,7-tetravinylcyclotetrasiloxane, dodecamethylcyclohexasiloxane, 1,3,5,7,9-pentamethylcyclopentasiloxane, 1,3,5,7,9-pentamethyl-1,3,5,7,9-pentavinylcyclopentasiloxane, 1,3,5-trimethyl-1,3,5-triphenylcyclotrisiloxane, 1,3,5-trimethyl-1,3,5-trivinylcyclotrisiloxane, 1,3,5,7,9,11-hexamethylcyclohexasiloxane, 1,3,5,7,9-pentamethylcyclopentasiloxane, 1,3,5,7-tetramethyl-1,3,5,7-tetravinylcyclotetrasiloxane, and the like.

The reaction can be carried out, for example, as follows. An epoxy-terminated polymer or an α,β-dihydroxy polymer, a chain-like or cyclic polysiloxane, and an acid or base catalyst are charged into a reactor and mixed, and the temperature is elevated until the mixture homogeneously dissolves. Here, the polysiloxane may be used in advance as a salt of an alkali metal or an alkaline earth metal. The reaction temperature is preferably a temperature at which the epoxy-terminated polymer used dissolves. The reaction temperature is preferably 25 to 300° C., more preferably 50 to 250° C., and even more preferably 80 to 200° C. Depending on the compound and solvent used, the reaction temperature may exceed the boiling point, and thus appropriate reaction apparatus such as autoclave should be selected. The reaction time may vary depending on the reaction conditions such as the amount of catalyst used, reaction temperature, reactivity of the polymers and the like, but is usually from a few minutes to 50 hours.

In the process for production of the invention, less generation of side products occurs, and after the reaction, a desired polyolefin-containing polysiloxane can be obtained by removing excessive catalyst, polysiloxane and reaction solvent through simple operations such as crystallization, washing and the like. For the reaction, the reaction can be also carried out with the epoxy-terminated polymer or α,β-dihydroxy polymer as the starting material obtained directly from its production process without being isolated and purified.

The number of siloxane unit contained in the polysiloxane of the invention can be measured by $^1$H-NMR. For example, in the case of the polyolefin-containing polysiloxane obtained by modifying an epoxy-terminated polymer comprising ethylene only with dimethylsiloxane, the number of the siloxane unit can be calculated from the peak-area ratio of the peaks for the 3 protons for a methyl group at one terminal (0.9 ppm) or the peak for the 1 proton at the base of a hydroxyl group (3.3 ppm) generated by siloxane modification, and the peak corresponding to the 6 protons for two methyl groups bound to silicon (0.1 ppm), that is, the 6 protons per 1 unit of dimethylsiloxane.

Conventionally known polyolefin-containing polysiloxane are such that, as disclosed in JP-A No. 4-126723, the average carbon number of the alkyl group added to the siloxane is 30 or less, the proportion of the silicone moiety is large, and the pour point is low. Thus, such polyolefin-containing polysiloxane is in the oily state, and its film formability or glazing effect cannot be said to be excellent.

Furthermore, when a polyolefin-containing polysiloxane having 30 or less carbon atoms in average is used as a cosmetic material, there is known a method of adding silicone oil so as to impart good stretching and smoothness. Since the cosmetic material obtained by this method has low surface tension, the cosmetic material spreads on the skin and has insufficient sustainability, moreover the compatibility with other oily components in the cosmetic material is poor.

In order to improve the compatibility, JP-B No. 5-53767 discloses a method of combining a polyolefin-containing polysiloxane having 30 or less carbon atoms in average with silicone oil and mixing them. This method could result in improvement in the compatibility, but the film formability was deteriorated.

Furthermore, JP-A No. 2000-198847 used a polysiloxane having 32 to 70 carbon atoms in average in order to improve the film formability, but the length of the alkyl group was insufficient, and sufficient improvement in the compatibility with other oily components was not obtained. Thus, there is a demand for a method for improving both the compatibility of a cosmetic material with other oily components, and the film formability as a cosmetic material.

Polymer (III)

Among the polymers containing the structural unit represented by the above Formula (1), another preferred example of the polymer is a novel polymer having specific functional groups on two positions that are adjacent to a polymer terminal, as represented by the following Formula (14) (hereinafter, referred to as Polymer (III)):

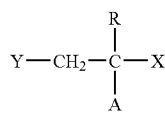
(14)

wherein A and R are as defined in the above Formula (1); X and Y are such that one of them is a hydroxyl group, a polyalkylene glycol group or an acyloxy group, while the other is a group represented by any of the following Formula (15), Formula (16) and Formula (17), a cyano group, a carboxyl group, an ester group or an amide group; or X and Y may be bound to each other to form a 5-membered ring:

-E-R$^7$ (15)

wherein E is an oxygen atom or a sulfur atom; and R$^7$ is a hydrogen atom, a hydrocarbon group, an acyl group or a polyalkylene glycol group;

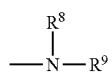
(16)

wherein R$^8$ and R$^9$, which may be identical or different, are each a hydrogen atom, a hydrocarbon group, an acyl group or a polyalkylene glycol group;

(17)

wherein R$^{10}$ to R$^{12}$, which may be identical or different, are each a hydrogen atom, a hydrocarbon group, an acyl group, a cyano group, a carboxyl group, an ester group or an amide group.

The Polymer (III) of the invention can be produced from a corresponding epoxy-terminated polymer represented by the Formula (8). As described above, the weight average molecular weight of the group represented by A can be determined as the value obtained by subtracting the molecular weight of an epoxy group, which is 42, and the molecular weight of the group represented by R, from the weight average molecular weight of the epoxy-terminated polymer.

The polyalkylene glycol group for X and Y in Formula (14) are preferably a group represented by the following Formula (18):

(18)

wherein R$^{13}$ is an alkylene group; R$^{14}$ is a hydrogen atom or an alkyl group; and r is an integer from 1 to 10,000. Here, the polyalkylene glycol group also includes the case where r in Formula (18) is 1.

The polyalkylene glycol group for R$^7$ to R$^9$ in Formulas (15) and (16) is a group represented by the following Formula (19):

(19)

wherein R$^{13}$ is an alkylene group; R$^{14}$ is a hydrogen atom or an alkyl group; and r is an integer from 1 to 10,000.

Here, the polyalkylene glycol group includes the case where r in Formula (19) is 1.

The alkylene group for R$^{13}$ is preferably an alkylene group having 1 to 20 carbon atoms. Examples of the alkylene group include a methylene group, an ethylene group, an ethylethylene group, a dimethylethylene group, a phenylethylene group, a chloromethylethylene group, an aryloxymethylethylene group, a propylene group, a trimethylene group, a hexamethylene group, a cyclohexylene group and the like. R$^7$ may be a single alkylene group or a mixture of two or more species of alkylene groups.

The alkyl group for R$^{14}$ is preferably a straight-chained, branched or cyclic alkyl group having 1 to 18 carbon atoms. Specific examples of the alkyl group include those listed for R of Formula (14).

The acyloxy group for X and Y in Formula (14) is preferably an acyloxy group having 2 to 15 carbon atoms, and may be bound with a functional group containing heteroatoms. Examples of the acyloxy group include an acetoxy group, a propionyloxy group, a 3-carboxypropionyloxy group, a 3-carboxy-2-propenoyloxy group, an acryloyloxy group, a methacryloyloxy group, a hexanoyloxy group, a benzoyloxy group, a trifluoromethylbenzoyloxy group, a 3-nitrobenzoyloxy group, a carboxybenzoyloxy group, a naphthyloxy group, a perfluoroheptanoyloxy group, a perfluorooctanoyloxy group and the like.

The hydrocarbon group for $R^7$ to $R^{12}$ in Formula (15), Formula (16) and Formula (17) is preferably an alkyl group, an alkenyl group, an aralkyl group or an aryl group, and may be bound with a functional group containing heteroatoms.

The alkyl group in this case is preferably a straight-chained, branched or cyclic alkyl group having 1 to 18 carbon atoms. Examples of the alkyl group include a methyl group, an ethyl group, a propyl group, a butyl group, a pentyl group, a hexyl group, an octyl group, a cyclopentyl group, a cyclohexyl group, a cyclooctyl group, a dihydroxypropyl group, a 2,2-bis(hydroxymethyl)-3-hydroxypropane, a tetradecyl group, an octadecyl group, a cyclopropylmethyl group, a cyclohexylmethyl group, a bromodecyl group, a trifluoroethyl group, a hexafluoro-2-propyl group, a perfluorooctyl group and the like.

The alkenyl group is preferably a straight-chained or branched alkenyl group having 2 to 6 carbon atoms. Examples of the alkenyl group include a vinyl group, an allyl group, a fluoroallyl group, an isopropenyl group, a pentenyl group, a hexenyl group and the like.

The aralkyl group is preferably an aralkyl group having 7 to 15 carbon atoms. Examples of the aralkyl group include a benzyl group, a difluorobenzyl group, a pentafluorophenylmethyl group, a bis(4-methoxyphenyl)methyl group, a phenethyl group, a benzhydryl group, a phenylpropyl group and the like.

The aryl group is preferably an aryl group having 6 to 15 carbon atoms. Examples of the aryl group include a phenyl group, a dichlorophenyl group, a methoxyphenyl group, a methoxycarbonylphenyl group, a nitrophenyl group, a hexafluorophenyl group, a tolyl group, a xylyl group, a naphthyl group and the like.

The acyl group for $R^7$ to $R^{12}$ in Formula (15), Formula (16) and Formula (17) is preferably an acyl group having 2 to 15 carbon atoms. Examples of the acyl group include an acetyl group, a propionyl group, a carboxypropionyl group, a carboxypropenoyl group, an acryloyl group, a methacryloyl group, an octanoyl group, a benzoyl group, a trifluoromethylbenzoyl group, a nitrobenzoyl group, a carboxybenzoyl group, a naphthoyl group, a perfluoroheptanoyl group, a perfluorooctanoyl group and the like.

The ester group for X and Y in Formula (14) and for $R^{10}$ to $R^{12}$ in Formula (17) is preferably an alkoxycarbonyl group or an aryloxycarbonyl group having 2 to 20 carbon atoms. Examples of the alkoxycarbonyl group or aryloxycarbonyl group include a methoxycarbonyl group, an ethoxycarbonyl group, a propoxycarbonyl group, a butoxycarbonyl group, a cyclohexyloxycarbonyl group, a butylcyclohexyloxycarbonyl group, a cyclopentylethoxycarbonyl group, a vinyloxycarbonyl group, an allyloxycarbonyl group, a perfluorohexyloxycarbonyl group, a perfluorooctyloxycarbonyl group, a benzyloxycarbonyl group, a phenoxycarbonyl group, a fluorophenoxycarbonyl group, a (methoxycarbonylphenyl)phenoxycarbonyl group, a naphthoxycarbonyl group and the like.

The amide group for X and Y in Formula (14) and for $R^{10}$ to $R^{12}$ in Formula (17) may be exemplified by a carbamoyl group, an N-methylcarbamoyl group, an N,N-dimethylcarbamoyl group, an N-(hydroxyethyl)carbamoyl group, an N,N-dibutylcarbamoyl group, a pyrrolidinylcarbonyl group, a piperidinylcarbonyl group or the like.

The divalent group represented by —X—Y— in the case where X and Y are bound to form a 5-membered ring is preferably any of the following groups:

—O—CO—O—

—O—CR$^{15}$R$^{16}$—O—

—O—CO—CHL— wherein L is a hydrogen atom, a cyano group, an ester group, or a carboxyl group; and $R^{15}$ and $R^{16}$ are each a hydrogen atom, an alkyl group or an aryl group.

The ester group for L in this case is preferably an alkoxycarbonyl group or an aryloxycarbonyl group having 2 to 20 carbon atoms. Specific examples of the ester group include those listed for X and Y in Formula (14) and for $R^{10}$ to $R^{12}$ in Formula (17).

The alkyl group represented by $R^{15}$ and $R^{16}$ is preferably a straight-chained, branched or cyclic alkyl group having 1 to 18 carbon atoms. Specific examples of the alkyl group include those listed for R in Formula (14).

The aryl group represented by $R^{15}$ and $R^{16}$ is preferably an aryl group having 6 to 15 carbon atoms, and examples thereof include a phenyl group, a dichlorophenyl group, a methoxyphenyl group, a nitrophenyl group, a tolyl group, a xylyl group, a naphthyl group and the like.

<Process of Producing Polymer (III)>

The Polymer (III) represented by Formula (14) can be produced from an epoxy-terminated polymer represented by the corresponding Formula (8). The process of producing the epoxy-terminated polymer and the content of epoxy group are as described above.

[Process of Producing (III-1) a Polymer Having a Hydroxyl Group for Either X or Y with Respect to Formula (14)]

[Process of Producing (III-1a) a Polymer Having a Hydroxyl Group for Either X or Y and the Group Represented by Formula (15) for the Other]

A polymer having a hydroxyl group for either X or Y and the group represented by Formula (15) for the other can be obtained by reacting the starting material epoxy-terminated polymer with a compound represented by the following Formula (20) (hereinafter, referred to as reacting agent A) in the presence of an acid or base catalyst:

$$\text{H-E-R}^7 \qquad (20)$$

wherein E and $R^7$ are each the same atom or group as that defined in Formula (15).

Examples of the Formula (20) include water; alcohols such as methanol, ethanol, propanol, octanol, allyl alcohol, cyclohexanol, propenyl alcohol, hexenol, bromodecanol, trifluoroethanol, hexafluoro-2-propanol, perfluorooctanol, benzyl alcohol, difluorobenzyl alcohol, pentafluorophenylmethanol, bis(4-methoxyphenyl)methanol, phenethyl alcohol, phenylpropyl alcohol, phenol, dichlorophenol, methoxyphenol, methoxycarbonylphenol, nitrophenol, hexafluorophenol, methylphenol, dimethylphenol, naphthyl alcohol and the like; polyhydric alcohols such as glycerin, butanetriol, pentaerythritol and the like; thioalcohols such as thiomethanol, thioethanol and the like; carboxylic acids such as acetic acid, propionic acid, maleic acid, malonic acid, hexanoic acid, octanoic acid, acrylic acid, methacrylic acid, benzoic acid, trifluoromethylbenzoic acid, nitrobenzoic acid, phthalic acid, naphthylic acid, perfluoroheptanoic acid, perfluorooctanoic acid and the like; and polyalkylene glycols such as monoethylene glycol, diethylene glycol, triethylene glycol, polyethylene glycol, phenylethylene glycol, monopropylene glycol, dipropylene glycol, tripropylene glycol, polypropylene glycol, propanediol, chloropropanediol, bromopropanediol, methoxypropanediol, allyloxypropanediol, butanediol, hexanediol, 1,4-cyclohexamethanediol and the like. These may be used individually or in combination of two or more species. The polyethylene glycol and polypropylene glycol are understood to include all of bifunctional, trifunctional and tetrafunctional compounds.

Examples of the acid catalyst include mineral acids such as hydrochloric acid, sulfuric acid, phosphoric acid and the like; sulfonic acids such as p-toluenesulfonic acid and the like; solid acids such as Amberlist-15 (registered trademark); and Lewis acids such as boron trifluoride ether complex, boron trichloride, boron tribromide, aluminum trichloride, aluminum tribromide, tin tetrachloride, zinc dichloride and the like.

Examples of the base catalyst include hydroxides, carbonates and hydrogen carbonates of alkali metals such as lithium, sodium, potassium, cesium and the like; hydroxides, carbonates and hydrogen carbonates of alkaline earth metals such as magnesium, calcium and the like; organic amines such as pyridine, 4-dimethylaminopyridine, triethylamine and the like; weakly basic ion exchange resins such as Amberlist-21 (registered trademark), Amberlist-93 (registered trademark) and the like; and the like.

The amount of the acid or base catalyst to be used is preferably 0.01- to 10-folds by weight, more preferably 0.1- to 5-folds by weight, and most preferably 0.5- to 2-folds by weight, with respect to the epoxy-terminated polymer. These acid or base catalysts may be used individually or in combination of two or more species.

For the reaction solvent, those inert to the starting material epoxy-terminated polymer can be used, and examples thereof include aliphatic hydrocarbons such as n-hexane and the like; alicyclic hydrocarbons such as cyclohexane and the like; aromatic hydrocarbons such as toluene, xylene and the like; esters such as ethyl acetate and the like; ketones such as acetone, methyl ethyl ketone, methyl isobutyl ketone, diethyl ketone, methyl propyl ketone and the like; ethers such as tetrahydrofuran, 1,4-dioxane and the like; halogenated hydrocarbons such as chloroform, dichloroethane, trichloroethane, dichlorobenzene and the like; and the like. As long as the starting material epoxy-terminated polymer is not insoluble in the solvent, aromatic hydrocarbons such as toluene, xylene and the like are preferred. The amount of the solvent to be used depends on the solubility of the starting material, but the amount is preferably 0.8- to 100-folds by weight, more preferably 1- to 50-folds by weight, and even more preferably 2- to 20-folds by weight, with respect to the starting material epoxy-terminated polymer.

The reaction can be carried out, for example, as follows. An epoxy-terminated polymer, a reacting agent A, and an acid or base catalyst are charged into a reactor and mixed, and the temperature is elevated until the mixture homogeneously dissolves. Here, the reacting agent A may be used in advance as a salt of an alkali metal or an alkaline earth metal. The reaction temperature is preferably a temperature at which the epoxy-terminated polymer used dissolves. The reaction temperature is preferably 25 to 300° C., more preferably 50 to 250° C., and even more preferably 80 to 200° C. Depending on the compound and solvent used, the reaction temperature may exceed the boiling point, and thus appropriate reaction apparatus such as autoclave should be selected. The reaction time may vary depending on the reaction conditions such as the amount of catalyst used, reaction temperature, reactivity of the polymers and the like, but is usually from a few minutes to 50 hours.

After the reaction, the desired polymer can be obtained by removing excessive catalyst, reacting agent A and reaction solvent through simple operations such as crystallization, washing and the like. The reaction can be also carried out using the starting epoxy-terminated polymer obtained directly from the production process without isolation and purification.

For the process of producing a polymer having hydroxyl groups for both X and Y with respect to Formula (14), a method of reacting the epoxy-terminated polymer with water in the co-presence of a compatibilizing solvent such as alcohol is preferable.

[Process of Producing (III-1b) a Polymer Having a Hydroxyl Group for Either X or Y and a Group Represented by Formula (16) for the Other]

A polymer having a hydroxyl group for either X or Y and the group represented by Formula (16) for the other can be obtained by reacting the epoxy-terminated polymer, which is the starting material, with a compound represented by the following Formula (21). The reaction may be carried out in the co-presence of an acid or base catalyst.

(21)

wherein $R^8$ and $R^9$ are each the same atom or group as that defined in Formula (16).

Examples of Formula (21) include ammonia, methylamine, ethylamine, methylpropylamine, ethanolamine, diethanolamine, ethylpropylamine, butylamine, decylamine, octadecylamine, pyrrolidine, piperidine, piperazine, hexamethyleneimine, ethylenediamine, diaminopropane, diaminobutane, diethylenetriamine, N-(aminoethyl)propanediamine, iminobispropylamine, spermidine, spermine, triethylenetetraamine, cyclopropylamine, cyclobutylamine, N-methylcyclohexylamine, diaminocyclohexane, benzylamine, tris(aminopropyl)amine, tris(aminoethyl)amine, aminomethylheptanediamine, aniline, chloroaniline, toluidine, aminophenol, methylenedianiline, phenylenediamine, aminonaphthalene, Jeffamines (registered trademark) and the like.

Jeffamine (registered trademark) is understood to include all of polyalkylene glycols containing amino groups at the terminals.

The acid or base catalyst and the amount of use thereof, the reaction solvent and the amount of use thereof are as described for the case of (III-1a).

The reaction can be carried out in the same manner as in the case of (III-1a), but the reaction also proceeds in the absence of the acid or base catalyst.

[Process of Producing (III-1c) a Polymer Having a Hydroxyl Group for Either X or Y and the Group Represented by Formula (17) for the Other]

A polymer having a hydroxyl group for either X or Y and the group represented by Formula (17) for the other can be obtained by reacting an epoxy-terminated polymer, which is the starting material, with an organic metal compound represented by the following Formula (22):

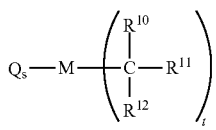

(22)

wherein $R^{10}$ to $R^{12}$ are each the same atom or group as that defined in Formula (17); M is an alkali metal, an alkaline earth metal, an aluminum atom, a silicon atom, or a tin atom; Q is a halogen atom; s is an integer from 1 to 4; and t is an integer from 0 to 3.

The halogen atom represented by Q may be exemplified by a fluorine atom, a chlorine atom, a bromine atom or an iodine atom.

The alkali metal represented by M may be exemplified by a lithium atom, a sodium atom, a potassium atom, a rubidium atom or a cesium atom.

The alkaline earth metal represented by M may be exemplified by a beryllium atom, a magnesium atom, a calcium atom, a strontium atom or a barium atom.

Examples of the organic metal compound represented by Formula (21) include enolates such as sodium enolate of ethyl acetate, sodium enolate of diethyl malonate, potassium enolate of malononitrile, lithium enolate of diethyl succinate, sodium enolate of ethyl 2-cyanoacetate and the like; organic metal compounds such as methyllithium, n-butyllithium, tert-butyllithium, diethylzinc, tripropylaluminum and the like; and the like.

Production of such organic metal compounds can be carried out using general methods.

The reaction can be carried out in the same manner as in the case of (III-1a). In this case, the reaction can be carried out without using an acid or base catalyst. Furthermore, after the reaction, the reaction mixture can be treated with water or a lower alcohol such as methanol, ethanol or the like to remove metals.

The reaction solvent and the amount of use thereof are the same as those for the case of (III-1a).

[Process of Producing (III-1D) a Polymer Having a Hydroxyl Group for Either X or Y, and a Cyano Group, a Carboxyl Group, an Ester Group or an Amide Group for the Other]

A polymer having a hydroxyl group for either X or Y and a cyano group for the other can be obtained by reacting an epoxy-terminated, which is the starting material, with a cyanating agent.

The cyano group of the resulting cyano group-containing polymer can be converted to a carboxyl group by hydrolysis. Further, this carboxyl group can be derived into an ester group by esterifying the carboxyl group, and can be derived into an amide group by amidating the carboxyl group. Such hydrolysis, esterification and amidation can be carried out by using general methods.

The cyanating agent may be exemplified by sodium cyanide, potassium cyanide, trimethylsilyl cyanide, diethylaluminum cyanide, acetone cyanohydrin or the like.

The amount of the cyanating agent to be used is preferably 0.9- to 20-folds by weight, more preferably 1- to 10-folds by weight, and even more preferably 1.1- to 10-folds by weight, with respect to the starting material epoxy-terminated polymer.

The reaction can be carried out in the same manner as in the case of (III-1a). In this case, the reaction can be carried out without using the acid or base catalyst.

The reaction solvent and the amount of use thereof are the same as those for the case of (III-1a).

[Process of Producing (III-2) a Polymer Having a Polyethylene Glycol Group for Either X or Y with Respect to Formula (14)]

A polymer having a polyethylene glycol group for either X or Y with respect to Formula (14) can be obtained by using the polymer obtained by the above-described process of production, which has a hydroxyl group for either X or Y with respect to Formula (14) (hereinafter, referred to as Polymer A) as the starting material, and reacting the hydroxyl group of the polymer with an epoxy compound.

The epoxy compound that is addition polymerized with the hydroxyl group may be exemplified by propylene oxide, ethylene oxide, 1,2-butylene oxide, 2,3-butylene oxide, styrene oxide, cyclohexene oxide, epichlorohydrin, epibromohydrin, methyl glycidyl ether, allyl glycidyl ether or the like. These may be used in combination of two or more species. Among these, preferred are propylene oxide, ethylene oxide, 1,2-butylene oxide, 2,3-butylene oxide and styrene oxide, and more preferred are propylene oxide and ethylene oxide.

The catalyst used for the reaction in the invention may be exemplified by alkali metal hydroxides. Further, phosphazenium compounds, phosphine oxide compounds, and phosphazene compounds (hereinafter, referred to as compounds having P=N bonding) also can be used.

Examples of the alkali metal hydroxide include calcium hydroxide, sodium hydroxide, lithium hydroxide, rubidium hydroxide, cesium hydroxide and the like.

Examples of the phosphazenium compound include tetrakis[tris(dimethylamino)phosphoranylideneamino]phosphonium hydroxide, tetrakis[tris(dimethylamino)phosphoranylideneamino]phosphonium methoxide, tetrakis[tris(dimethylamino)phosphoranylideneamino]phosphonium methoxide, tetrakis[tri(pyrrolidin-1-yl)phosphoranylideneamino]phosphonium tert-butoxide and the like.

Examples of the phosphine oxide include tris[tris(dimethylamino)phosphoranylideneamino]phosphine oxide, tris[tris(diethylamino)phosphoranylideneamino]phosphine oxide and the like.

Examples of the phosphazene compound include 1-tert-butyl-2,2,2-trimethylphosphazene, 1-(1,1,3,3-tetramethylbutyl)-2,2,4,4,4-pentaisopropyl-$2\lambda^5,4\lambda^5$-catenadi(phosphazene), 1-tert-butyl-2,2,2-triallylphosphazene, 1-cyclohexyl-2,2,4,4,4-pentaallyl-$2\lambda^5,4\lambda^5$-catenadi(phosphazene), 1-ethyl-2,4,4,4-tribenzyl-2-tribenzylphosphoranylideneamino-$2\lambda^5$, $4\lambda^5$-catenadi(phosphazene), 1-methyl-2,2,2-tricyclopentylphosphazene, 1-propyl-2,2,4,4,4-cyclohexyl-$2\lambda^5,4\lambda^5$-catenadi(phosphazene) and the like.

The amount of the catalytic alkali metal hydroxide to be used is preferably in the range of 0.05 to 0.5 moles, and more preferably in the range of 0.1 to 0.3 moles, based on 1 mole of the starting material polymer A.

The amount of the catalytic compound having P=N bonding to be used is preferably $1 \times 10^{-4}$ to $5 \times 10^{-1}$ moles, more preferably $5 \times 10^{-4}$ to $1 \times 10^{-1}$ moles, and even more preferably $1 \times 10^{-3}$ to $1 \times 10^{-2}$ moles, based on 1 mole of the starting material polymer A, in the aspects of the rate of polymerization, economic efficiency and the like.

The temperature at which an epoxy compound is addition polymerized to the starting material Polymer A is preferably in the range of 15 to 130° C., more preferably 40 to 120° C., and even more preferably 50 to 110° C., in the aspects of the rate of polymerization and inhibition of side reactions. When the addition polymerization of epoxy compound is to be carried out at a temperature lower than the above range, it is desirable to increase the concentration of the compound having P═N bonding with respect to the starting material Polymer A, to the above-mentioned range.

The pressure for the addition polymerization of epoxy compound is preferably 882 kPa or less from the viewpoint of inhibiting side reactions. The addition polymerization of epoxy compound is usually carried out in a pressure resistant reactor. The reaction of the epoxy compound may be started under reduced pressure or under the atmospheric pressure. When the reaction is started under the atmospheric pressure, it is desirably carried out in the presence of an inert gas such as nitrogen, helium or the like. The reaction pressure is more preferably 686 kPa or less, and even more preferably 490 kPa or less.

When propylene oxide is used as the epoxy compound, the reaction pressure is preferably 490 kPa or less.

For feeding the epoxy compound to the reaction, a method in which a portion of the needed amount of the epoxy compound is fed all at once and the remaining portion is continuously fed, a method in which all of the epoxy compound is continuously fed all of the epoxy compound, or the like may be used. In the method of feeding a portion of the needed amount of the epoxy compound all at once, it is preferable that the initial reaction temperature for the polymerization reaction of epoxy compound is set at a temperature lower than the above-described temperature range, and after charging the epoxy compound, the reaction temperature is gradually increased.

For the polymerization using propylene oxide and ethylene oxide in combination as the epoxy compounds, mention may be made of (a) an ethylene oxide capping reaction in which propylene oxide is polymerized first, and then ethylene oxide is block-copolymerized thereto; (b) a random reaction in which propylene oxide and ethylene oxide are randomly copolymerized; and (c) a triblock copolymerization reaction in which propylene oxide is polymerized first, subsequently ethylene oxide is polymerized, and then propylene oxide is polymerized. Among these, the preferred polymerization is the ethylene oxide capping reaction and the triblock copolymerization reaction.

The maximum pressure for the addition polymerization reactor is affected by the rate of charging the epoxy compound, the polymerization temperature, the amount of catalyst, and the like. The rate of charging the epoxy compound is preferably controlled such that the maximum pressure for the addition polymerization reactor does not go beyond 882 kPa. When charging of the epoxy compound is completed, the internal pressure of the addition polymerization reactor gradually decreases. It is desirable to continue the addition polymerization reaction until no change in the internal pressure is confirmed. Taking reference to the hydroxyl group value (OHV) of the polyalkylene glycol group-containing polymer, it is desirable to continue the addition polymerization until the OHV reaches 2 to 200 mg KOH/g.

In regard to the addition polymerization reaction of the epoxy compound, a solvent may be used. Examples of the solvent include aliphatic hydrocarbons such as pentane, hexane, heptane and the like; aromatic hydrocarbons such as toluene, xylene and the like; ethers such as diethyl ether, tetrahydrofuran, dioxane and the like; aprotonic polar solvents such as dimethylsulfoxide, N,N-dimethylformamide and the like; and the like.

Next, the process of purifying the polyalkylene glycol group-containing polymer produced as described above will be explained. The alkali metal hydroxides or the compounds having P═N bonding that residually remain in the polyalkylene glycol group-containing polymer produced, can be removed by methods of neutralization with mineral acids such as hydrochloric acid, phosphoric acid and the like, organic acids such as acetic acid and the like, carbon dioxide, and the like; removal by adsorption with an adsorbent; washing with water or water/organic solvent; ion exchange using an ion exchange resin; and the like.

[Process of Producing (III-3) a Polymer Having an Acyloxy Group for Either X or Y with Respect to Formula (14)]

A polymer having an acyloxy group for either X or Y with respect to Formula (14) can be obtained by using the Polymer A as the starting material and acylating the hydroxyl group or the like thereof. The acylation can be carried out by a general method in which the Polymer A is reacted with a corresponding acid halide or acid anhydride in the presence of a base catalyst.

Examples of the acid halide include acetyl chloride, propionyl bromide, acryloyl chloride, methacryloyl chloride, hexanoyl bromide, octanoyl iodide, benzoyl chloride, 4-trifluoromethylbenzoyl iodide, 3-nitrobenzoyl bromide, naphthyl chloride, perfluoroheptenoyl bromide, perfluorooctenoyl iodide and the like.

Examples of the acid anhydride include anhydrous acetic acid, anhydrous propionic acid, anhydrous acrylic acid, anhydrous methacrylic acid, anhydrous phthalic acid, anhydrous maleic acid, anhydrous succinic acid and the like.

As the base catalyst, the catalysts exemplified for (III-1a) can be mentioned.

[Process of Producing (III-4) a Polymer Having X and Y Bound to Each Other to Form a 5-Membered Ring with Respect to Formula (14)]

[Process of Producing (III-4a) a Polymer Having —O—CO—O— as the Divalent Group Represented by —X—Y—]

A polymer having —O—CO—O— as the divalent group represented by —X—Y— can be obtained by reacting the starting material epoxy-terminated polymer with carbon dioxide in the presence of a catalyst.

Examples of the catalyst include alkali metal halides such as lithium chloride, lithium bromide, sodium chloride, sodium bromide, sodium iodide, potassium chloride, potassium bromide, potassium iodide, cesium chloride and the like; alkali metal hydroxides such as lithium hydroxide, sodium hydroxide, potassium hydroxide, cesium hydroxide and the like; tertiary ammonium salts such as triethylamine perchlorate and the like; quaternary ammonium salts such as tetrabutylammonium bromide and the like; basic anion exchange resins containing a quaternary ammonium salt as an active group; magnesium oxide; and the like.

According to the invention, the amount of the catalyst to be used is not particularly limited, but the amount is preferably 0.1 to 200% by weight, and more preferably 1.0 to 50% by weight, based on the total weight of the starting material epoxy-terminated polymer and carbon dioxide. These catalysts may be used individually or in combination of two or more species.

The reaction in the invention can be carried out without solvent, but also can be carried out in the presence of a solvent, if necessary. The solvent and the amount of use thereof are the same as those in the case for (III-1a).

The reaction can be carried out in any of the liquid phase, gas phase and liquid-gas mixed phase. Further, the reaction can be also carried out under any of the conditions of ambient pressure, overpressure and underpressure. From the viewpoint of reaction efficiency, the reaction is preferably carried out in the liquid phase.

In regard to the liquid phase reaction, when the reaction is carried out at a reaction temperature higher than the boiling point of the starting material or the product, the reaction can be also carried out under the conditions of overpressure generated by a gas inert to the starting material and the reaction product (for example, argon, nitrogen, helium or the like).

The reaction temperature is not particularly limited, but is preferably 0 to 250° C., and more preferably 50 to 200° C.

The reaction time is not particularly limited, but is preferably about a few minutes to 30 hours, and more preferably about 0.5 to 15 hours.

The feed composition of the starting material epoxy-terminated polymer and carbon dioxide to be added is not particularly limited, but for example, in order to achieve a high conversion rate for the epoxy-terminated polymer, it is preferable to increase the molar ratio of carbon dioxide to the epoxy-terminated polymer. The molar ratio of carbon dioxide to the epoxy-terminated polymer according to the invention is preferably in the range of 0.05 to 50, and more preferably in the range of 0.5 to 25.

After the main reaction, the produced terminal carbonate is isolated and purified by purification methods such as crystallization, washing and the like.

Further, the polymer having —O—CO—O— as the divalent group represented by —X—Y— can be also synthesized by carbonatizing a polymer having hydroxyl groups for both X and Y with respect to Formula (14) (referred to as Polymer B) using a carbonatizing agent. The carbonatizing agent may be exemplified by phosgene, diphenyl carbonate, dimethyl carbonate, methyl chloroformate, phenyl chloroformate or the like. For the carbonatization, a base catalyst and a solvent may be co-present. The base catalyst and the amount of use thereof, the reaction solvent and the amount of use thereof are the same as those in the case of (III-1a).

The reaction is conducted by mixing the Polymer B, carbonatizing agent and base catalyst, and heating the mixture with stirring. The reaction temperature is preferably a temperature at which the polymer used melts, but the temperature is preferably 25° C. to 300° C., more preferably 50° C. to 250° C., and even more preferably 80° C. to 200° C. Depending on the compound and solvent used, the reaction temperature may be higher than the boiling point; therefore, an appropriate reaction apparatus such as autoclave should be selected. The reaction time varies depending on the reaction conditions such as the amount of catalyst used, reaction temperature, reactivity of the polymers, and the like, but the time is usually from a few minutes to 50 hours. In the production process of the invention, less side products are generated, and the desired polymer can be obtained by removing the excess catalyst and the excess reaction solvent after the reaction, through simple operations such as crystallization, washing and the like.

[Process of Producing (III-4b) a Polymer Having —O—$CR^{15}R^{16}$—O— as the Divalent Group Represented by —X—Y—]

A polymer having —O—$CR^{15}R^{16}$—O— as the divalent group represented by —X—Y— can be obtained by reacting the epoxy group of the starting material epoxy-terminated polymer with a carbonyl compound in the presence of a catalyst. The carbonyl compound used herein is a carbonyl compound represented by $R^{15}R^{16}C=O$, which corresponds to the above-described structure, and examples thereof include formaldehyde, acetaldehyde, propionaldehyde, benzaldehyde, acetone, methyl ethyl ketone, isobutyl methyl ketone, acetophenone, benzophenone and the like. The amount of the carbonyl compound to be used is preferably in the range of 1 to 100 moles, more preferably 1.1 to 50 moles, and even more preferably 1.2 to 20 moles, based on 1 mole of the starting material epoxy-terminated polymer.

The catalyst used for the present reaction may be exemplified by base catalysts and benzylpyridinium salts. The base catalyst and the amount of use thereof are the same as those in the case of (III-1a).

Examples of the benzylpyridinium salt include methoxybenzylcyanopyridinium salts, benzylcyanopyridium salts and the like. The benzylpyridinium salt used as the catalyst is used in an amount preferably in the range of 0.0001 to 1 mole, and more preferably in the range of 0.001 to 0.1 moles, based on 1 mole of the starting material epoxy-terminated polymer.

The reaction conditions are not particularly limited, but for example, the reaction can be carried out at room temperature to 80° C., with stirring for 5 to 120 minutes.

The reaction in the invention can be carried out without using a solvent, but it is also possible to use a solvent. The solvent and the amount of use thereof are the same as those in the case of (III-1a). The polymer having —O—$CR^{15}R^{16}$—O— as the divalent group represented by —X—Y— can be also synthesized by acetalizing the hydroxyl groups of the Polymer B with a carbonyl compound represented by $R^{15}R^{16}C=O$. The reaction can be carried out by a general method for the acetalization reaction of a carbonyl compound using an alcohol.

[Process of Producing (III-4c) a Polymer Having —O—CO—CHL- as the Divalent Group Represented by —X—Y—]

A polymer having —O—CO—CHL- as the divalent represented by —X—Y— can be obtained by synthesizing a polymer having a hydroxyl group for either X or Y and a group represented by the following Formula (23) for the other with respect to Formula (14) (referred to as Polymer C) by the method for (III-1c), and heating the resulting polymer in the presence of an acid or base catalyst:

(23)

wherein L is the atom or group as described above; and $R^{17}$ is a hydrogen atom or an alkyl group.

The alkyl group for $R^{17}$ is preferably a straight-chained, branched or cyclic alkyl group having 1 to 18 carbon atoms. Specific examples of the alkyl group include those exemplified for R in Formula (14).

The reaction is conducted by heating Polymer C and the catalyst in the presence of a solvent. The acid or base catalyst and the amount of use thereof, the reaction solvent and the amount of use thereof are the same as those in the case of (III-1a).

The reaction can be carried out, for example, as follows. Polymer C and an acid or base catalyst are added to a reactor and mixed, and the temperature is elevated until the polymer homogenously melts. The reaction temperature is preferably a temperature at which the polymer used melts. The temperature is preferably 25° C. to 300° C., more preferably 50° C. to 250° C., and even more preferably 80° C. to 200° C. Depending on the compound and solvent used, the reaction temperature may be higher than the boiling point; therefore, an appropriate reaction apparatus such as autoclave should be selected. The reaction time varies depending on the reaction conditions such as the amount of the catalyst used, reaction temperature, reactivity of the polymers and the like, but the time is usually from a few minutes to 50 hours.

After the reaction, the desired polymer can be obtained by removing the excess catalyst and the excess reaction solvent through simple operations such as crystallization, washing and the like.

<Use of Polymers (I) to (III)>

The polymer of the invention described above, a composition containing the above-mentioned polymer, a resin composition containing the above-mentioned polymer and other thermoplastic resin, or the above-mentioned polymer is useful as an antistatic agent, an adhesive and a coating composition, and has an excellent antistatic effect.

Here, the amount of the polymer of the invention contained in the aforementioned composition, resin composition, antistatic agent, adhesive and coating composition is preferably 0.5 to 20% by weight, and particularly preferably 1.0 to 10% by weight.

Examples of the other thermoplastic resin in the resin composition include polyolefin resins such as polyethylene, polypropylene and the like; polystyrene resins such as polystyrene, acrylonitrile/butadiene/styrene copolymer (ABS resin) and the like; acrylic resins such as polymethyl methacrylate, polybutyl acrylate and the like; rubber-like (co) polymers such as polybutadiene, polyisoprene and the like; polyester resins such as polyethylene terephthalate, polybutylene terephthalate and the like; polyamide resins; polyacetal resins; polycarbonate resins; thermoplastic polyurethane resins; fluoro resins; and mixtures of two or more of these.

The above-mentioned composition or resin composition may contain at least one selected from the group consisting of salts of alkali metals or alkaline earth metals, surfactants and other polymeric antistatic agents (polymeric antistatic agents other than the antistatic agents comprising the polymer of the invention). According to these components, the antistatic property of the composition or of the resin composition can be further improved.

Preferred examples of the salts of alkali metals or alkaline earth metals include monocarboxylic acids or dicarboxylic acids having 1 to 20 carbon atoms (for example, formic acid, acetic acid, propionic acid, oxalic acid, succinic acid, etc.), sulfonic acids having 1 to 20 carbon atoms (for example, methanesulfonic acid, p-toluenesulfonic acid, etc.), salts of alkali metals and alkaline earth metals with organic acids such as thiocyanic acid and the like, hydrohalic acids (for example, hydrochloric acid, hydrobromic acid, etc.), and salts of inorganic acids such as hydrobromic acid, perchloric acid, sulfuric acid, phosphoric acid and the like. Among these, preferred ones are halides such as lithium chloride, sodium chloride, potassium chloride and the like; acetates such as potassium acetate and the like; and perchlorates such as potassium perchlorate and the like.

The content of the salts of alkali metals or alkaline earth metals in the composition or resin composition is usually 0.001 to 3-% by weight, preferably 0.01 to 2% by weight, based on the total amount of the polymers and resins.

As the surfactant, nonionic, anionic, cationic or zwitterionic surfactants can be used. Examples of the nonionic surfactant include polyethylene glycol type nonionic surfactants such as higher alcohol ethylene oxide adducts, fatty acid ethylene oxide adducts, higher alkylamine ethylene oxide adducts, polypropylene glycol ethylene oxide adducts and the like; polyhydric alcohol type nonionic surfactants such as polyethylene oxide, fatty acid esters of glycerin, fatty acid esters of pentaerythrite, fatty acid esters of sorbate or sorbitan, alkyl ethers of polyhydric alcohol, aliphatic amides of alkanolamine and the like; and the like. Examples of the anionic surfactant include carbonates such as alkali metal salts of high fatty acids; sulfuric acid ester salts such as high alcohol sulfuric acid ester salts, higher alkylether sulfuric acid ester salts and the like, sulfonates such as alkylbenzene sulfonates, alkyl sulfonates, paraffin sulfonates and the like; phosphoric acid ester salts such as higher alcohol phosphoric acid ester salts; and the like. Examples of the cationic surfactant include quaternary ammonium salts such as alkyltrimethylammonium salts and the like. Examples of the zwitterionic surfactant include amino acid type zwitterionic surfactants such as higher alkylaminopropionates and the like; betaine type zwitterionic surfactants such as higher alkyldimethylbetaine, higher alkyldihydroxyethylbetaine and the like; and the like. These may be used individually or in combination of two or more species.

Among the above-mentioned surfactants, anionic surfactants are preferred, and sulfonates such as alkylbenzene sulfonates, alkylsulfonates, paraffin sulfonates and the like are particularly preferred.

The content of the surfactant in the composition or resin composition is usually 0.001 to 5% by weight, preferably 0.01 to 3% by weight, based on the total amount of the polymers and resins.

As the other polymeric antistatic agent, for example, known polymeric antistatic agents such as polyether ester amide and the like can be used, and the known polyether ester amide may be exemplified by the polyether ester amides formed from the polyoxyalkylene adducts of bisphenol A described in JP-A No. 7-10989.

As other polymeric antistatic agents, block polymers having a repeating structure comprising 2 to 50 combined units of polyolefin blocks and hydrophilic polymer blocks can be used, and for example, the block polymers described in U.S. Pat. No. 6,552,131 can be mentioned.

The content of the other polymeric antistatic agent in the composition or resin composition is usually 0 to 40% by weight, preferably 5 to 20% by weight, based on the total amount of the polymers and resins.

The composition or resin composition may also contain a compatibilizing agent. By using the compatibilizing agent, the compatibility of the polymer of the invention with other thermoplastic resins can be improved. Such compatibilizing agent may be exemplified by modified vinyl polymers having at least one functional group (polar group) selected from the group consisting of a carboxyl group, an epoxy group, an amino group, a hydroxyl group and a polyoxyalkylene group, such as the polymers described in JP-A No. 3-258850; modified vinyl polymers having sulfonyl group described in JP-A No. 6-345927; block polymers having a polyolefin moiety and an aromatic vinyl polymer moiety; or the like.

The content of the compatibilizing agent in the composition or resin composition is usually 0.1 to 15% by weight, preferably 1 to 10% by weight, based on the total amount of the polymers and resins.

The composition or resin composition may arbitrarily contain additives for other resins in accordance with the use, within the scope of not impairing the effect given by the polymer of the invention. Such additives for resins may be exemplified by pigment, dye, filler, glass fiber, carbon fiber, lubricant, plasticizer, releasing agent, antioxidant, flame retardant, UV absorbent, antibacterial agent, or the like.

The molded product obtained by molding the resin composition has excellent antistatic property as well as good coatability and printability. For the method of molding the resin composition, mention may be made of injection molding, compression molding, calendar molding slush molding, rotational molding, extrusion molding, blow molding, film molding (casting, tenter, inflation methods, etc.), and the molding product can be formed by any method in accordance with the purpose.

The method for coating the molded product may include, for example, air spray coating, airless spray coating, static spray coating, immersion coating, roller coating, brushing and the like, without being limited to these. As the paint, for example, paints generally used for coating of plastics such as polyester melamine resin paint, epoxy melamine resin paint, acrylic melamine resin paint, acrylic urethane resin paint and the like can be used. The thickness of the coating film can be appropriately selected in accordance with the purpose, but the thickness is usually 10 to 50 μm (thickness of dried film).

The method of printing on the molded product may be any of the printing methods generally used for printing on plastics, and for example, gravure printing, flexographic printing, screen printing, offset printing and the like can be mentioned. As the ink used in such printing methods, those usually used in printing on plastics can be used.

The polymers of the invention is useful as a releasing agent for toner, a pigment dispersant, a lubricant for vinyl chloride resins, an emulsion composition and other applications as described below.

[Releasing Agent for Toner]

Polymers (I) to (III) according to the invention are suitable as a releasing agent for toner and impart an anti-offset property to a fixing roll. Specifically, the polymers improve image sharpness. This releasing agent is used as a component of the toner for static charge image development, together with a binding resin (a) and a colorant (b), and optionally a static charge controlling agent and the like. The weight average molecular weight of the group represented by A of the polymer used as the releasing agent is preferably in the range of 500 to 5,000, and more preferably in the range of 800 to 3,000.

The binding resin (a) may be any of those comprising the thermoplastic resins generally added to the developer for static charge image, and is not particularly limited. For example, mention may be made of those comprising styrene resins, styrene-acrylic ester-acrylic acid copolymers, acrylic resins, styrene-butadiene resins, ketone resins, maleic acid resins, polyester resins, polyvinyl acetate resins, coumarone resins, phenolic resins, silicone resins, polyurethane, epoxy resins, terpene resins, polyvinyl butyral, polybutyl methacrylate, polyvinyl chloride, polyethylene, polypropylene, polybutadiene, ethylene-vinyl acetate copolymers, rosin resins and the like.

Among these, styrene-acrylic acid ester copolymers, polyester aromatic resins and epoxy resins having appropriate softening points (90° C. to 120° C.) and good fixability are particularly preferred.

The colorant (b) may be any of those generally added to the developer for static charge image and are not particularly limited. For example, mention may be made of pigments or dyes such as carbon black, phthalocyanine blue, aniline blue, arcooil blue, chrome yellow, ultramarine blue, quinoline yellow, lamp black, Rose Bengal, diazo yellow, Rhodamine B lake, Carmine 6B, and quinacridone derivatives, and these are used individually or in combination of two or more species.

The mixing ratio of the releasing agent for toner of the invention is usually such that the ratio by weight of binding resin/colorant/static charge controlling agent/releasing agent of the invention is about binding resin 100/colorant 1 to 10/static charge controlling agent 0 to 5/releasing agent of the invention about 0.5 to 40, and preferably the ratio by weight of binding resin 100/colorant 1 to 6/static charge controlling agent 0.5 to 2/releasing agent of the invention 10 to 20.

[Pigment Dispersant]

Polymers (I) to (III) according to the invention are suitable as a pigment dispersant, and their excellent wettability on various pigments improves sustainability. Specifically, the polymers allow the use of masterbatches of high concentration. This dispersant is mixed with pigments and then mixed with the resins to be colored. Subsequently, the mixture is kneaded and granulated in an extruder to be used as dry colors, color compounds or masterbatches. The mixing ratio of the pigment dispersant is usually in the range of 25 to 200 parts by weight, preferably 50 to 150 parts by weight, based on 100 parts by weight of pigment.

The weight average molecular weight of the group represented by A of the Polymers (I) to (III) that are used as pigment dispersants is preferably in the range of 1,000 to 10,000, and more preferably in the range of 2,000 to 6,000.

The resin to be colored may be exemplified by polyolefinic resins such as polyethylene, polypropylene, polybutene-1, poly-4-methylpentene-1, ethylene-propylene copolymers, ethylene vinyl acetate copolymers and the like; styrene resins such as polystyrene, ABS and the like; polycarbonate resins obtained from bisphenol-A and phosgene; polyester resins such as polyethylene terephthalate, polybutylene terephthalate and the like; thermoplastic resins such as polyamide resins, polyphenylene oxide resins, polyvinyl chloride and the like; and thermosettable resins such as phenolic resins, epoxy resins and the like.

In particular, the pigment dispersant of the invention can be used suitably for thermoplastic resins. As the pigment that can be used, all traditionally known pigments effective in coloration of synthetic resins can be applied. Specific examples of the pigment include metals such as aluminum, silver, gold and the like; carbonates such as calcium carbonate, barium carbonate and the like; oxides such as $ZnO$, $TiO_2$ and the like; hydroxides such as $Al_2O_3.nH_2O$, $Fe_2O_3.nH_2O$ and the like; sulfates such as $CaSO_4$, $BaSO_4$ and the like; nitrates such as $Bi(OH)_2NO_3$ and the like; chlorides such as $PbCl_2$ and the like; chromates such as $CaCrO_4$, $BaCrO_4$ and the like; chromites, manganates and permanganates such as $CoCrO_4$ and the like; borates such as $Cu(BO)_2$ and the like; uranates such as $Na_2U_2O_7.6H_2O$ and the like; nitrites such as $K_3Co(NO_2)_6.3H_2O$ and the like; silicates such as $SiO_2$ and the like; arsenates and arsenites such as $CuAsO_3.Cu(OH)_2$ and the like; acetates such as $Cu(C_2H_3O_2)_2.Cu(OH)_2$ and the like; phosphates such as $(NH_4)_2MnO_2(P_2O_7)_2$ and the like; inorganic pigments such as aluminates, molybdenates, zincates, antimonates, tungstates, selenides, titanates, ferrocyanates, phthalates, CaS, ZnS, CdS and the like, natural organic pigments such as cochineal.lake, Madder.lake and the like, nitroso pigments such as Naphthol.Green Y, Naphthol.Green B and the like; nitro pigments such as Naphthol Yellow S, Pigment.Chlorine 2G and the like; Permanent.Red 4R; azo pigments such as Hansa Yellow, Brilliant.Carmine 68, Scarlet 2R and the like; and organic pigments, for example, basic dye lakes such as Malachine.Green, Rhodamine B and the like, acidic dye lakes such as acids Green lake, Eosin lake and the like, mordant dye lakes such as alizarin.lake, purpurin.lake and the like, vat dye pigments such as Thio.Indigo.Red B, Indanthrene.orange and the like, phthalocyanine pigments such as Phthalocyanine Blue, Phthalocyanine Green and the like.

The pigment dispersant of the invention can be used for the coloration by any method among a dry color method, a color compound method, or a masterbatch method. Among these, the masterbatch method can be particularly preferably used.

[Lubricant for Vinyl Chloride Resins]

Polymers (I) to (III) according to the invention are suitable as a lubricant for vinyl chloride resins, and they have excellent lubricant balance and thus have sustainability. Specifically, the productivity is improved, and such improvement leads to reduction of the consumed electric power. In the polyvinyl chloride composition employing the lubricant of the invention, the mixing ratio of the lubricant is in the range of 0.05 parts by weight to 5 parts by weight, and preferably in the range of 0.1 parts by weight to 3 parts by weight, based on 100 parts by weight of polyvinyl chloride. The weight average molecular weight of the group represented by A of the polymer used as lubricant is preferably in the range of 400 to 10,000, and more preferably in the range of 500 to 5,000.

The Polymer (I) to (III) used as a lubricant are preferably a polymer having a carboxyl group for either X or Y with respect to Formula (14).

The polyvinyl chloride resin of the invention containing the additives for polyvinyl chloride resins may be either polyvinyl chloride or a mixture of polyvinyl chloride with polyethylene, polypropylene, ABS resin, MBS resin, ethylene-vinyl acetate copolymer, polymethyl methacrylate or the like.

Also, the composition may further contain a heat resistant stabilizer. The heat resistant stabilizer may be any material showing a stabilizing effect on polyvinyl chloride resins, and for example, lead compounds, cadmium compounds, barium compounds, calcium compounds, zinc compounds, organic tin compounds, epoxy compounds, chelators, and mixtures of these are used. The polyvinyl chloride composition containing the lubricant according to the invention may further contain other lubricant, filler, pigment, dye, plasticizer, antistatic agent or weather resistant stabilizer.

The composition containing the lubricant according to the invention has excellent initial activity. Thus, the adhesiveness to metals is reduced, and the composition can be stably molded, thereby continuous operation possibly being carried out for a long time.

[Emulsion Composition]

Polymers (I) to (III) according to the invention are suitable as an emulsion composition. An emulsion composition having excellent lubricability, rub resistance, mold releasability and antibacterial property and having excellent storage stability can be obtained by stirring the polymer in a molten state and water at a high speed using a homomixer, a homogenizer or a disperser under high pressure.

The weight average molecular weight of the group represented by A of the Polymers (I) to (III) used as the emulsion composition is preferably in the range of 400 to 20,000, and more preferably in the range of 500 to 10,000, and the group represented by A of Polymer (III) has the constitutional unit derived from ethylene preferably in the range of 75 to 100% by mole, and more preferably in the range of 90 to 100% by mole.

The Polymers (I) to (III) used as the emulsion composition are preferably polymers containing a polyalkylene glycol group or a nitrogen-containing substituent for either X or Y with respect to Formula (14). Specific examples of the polyalkylene glycol group include polyethylene glycol or polypropylene glycol. Specific examples of the nitrogen-containing substituent include those formed from aliphatic straight-chained polyamines containing primary and secondary amino groups, which are represented by formula $NH_2-(C_2H_4NH)_n-NH_2$, such as ethylenediamine, diethylenetriamine, tetraethylenepentamine, hexaethyleneheptamine and the like.

Further, the emulsion composition may contain, if necessary, halogen ions or organic anions for the purpose of improving the storage stability of the dispersion system. Specific examples of the halogen ion include the ions of chlorine, iodine and bromine, while specific examples of the organic anion include methosulfate, ethosulfate, methophosphate and ethophosphate.

In addition, the emulsion composition may also contain, if necessary, cationic surfactants for the purpose of improving the storage stability of the dispersion system.

Specific examples of the cationic surfactant include distearyldimethylammonium chloride, stearyltrimethylammonium chloride, capryltrimethylammonium chloride, myristyltrimethylammonium chloride, cetyltrimethylammonium chloride, behenyltrimethylammonium chloride, lauryltrimethylammonium chloride, N-stearyl-N,N,N-tri(polyoxyethylene)ammonium chloride (addition of 3 moles in total of ethylene oxide), cetylbenzyldimethylammonium chloride, cetyltriethylammonium bromide, hexadecyloctadecyldimethylammonium chloride, stearamidopropyldimethylamine, and also other alkyl (alkyl group having 8 to 28 carbon atoms) dimethylbenzylammonium salts, dialkyl (alkyl group having 8 to 28 carbon atoms) methylhydroxyethylammonium salts, and the like.

The particle size of the emulsion composition according to the invention refers to the diameter based on the volume average. The particle size is preferably 10 nm to 20 μm.

The ink composition, coating composition and fiber treatment composition containing the emulsion composition of the invention exhibit good dispersibility in an acid environment, and have excellent lubricability, rub resistance, mold releasability, durability and water resistance.

[Oxygen Trapping Composition]

Polymers (I) to (III) according to the invention are suitable as an oxygen trapping composition, and in particular, they can impart an oxygen blocking property to polyester resins when contained in the polyester resins such as PET and the like. Thus, the storage stability of oxygen-sensitive materials contained in, for example, PET bottles and the like can be improved.

For the resin used in such applications, Polymer (I) is particularly effective, and inter alia, a copolymer of the structural unit represented by Formula (2) with polyester is most effective. Oxygen trapping is achieved when a polyolefin segment represented by A of Formula (2) radically reacts with oxygen to form a hydroxyl group via a peroxo radical. Therefore, polyolefins containing more tertiary carbons, for example, polypropylene, C3-C2 copolymers are more effective. The weight average molecular weight of the polyolefin segment is preferably 400 to 10,000. The weight average molecular weight of Polymer (I) used as the oxygen trapping composition is not particularly limited, but it is in general 10,000 to 500,000. The content of the polyolefin segment in the Polymer (I) used as the oxygen trapping composition is 0.1% by weight to 20% by weight, and preferably 0.5% by weight to 10% by weight.

[Other Uses]

Polymers (I) to (III) according to the invention can be widely used for the applications where known low molecular weight polyethylene such as wax and the like are used. Here, if necessary, various additives may be added and used.

For example, when Polymers (I) to (III) according to the invention are used as a coating material modifying agent, the coating surface can be modified. For example, the polymers have an excellent matting effect and can improve the abrasion resistance of the coating, thus possibly imparting high quality look to wood paints and improving the durability.

When Polymers (I) to (III) according to the invention are used as a glossing agent for car wax, floor polish and the like, the glossing agent has excellent gloss and can improve the coating film properties.

Polymers (I) to (III) according to the invention are suitable as a mixing agent for natural waxes such as crayons, candles and the like, and can improve the surface hardness and softening point.

Polymers (I) to (III) according to the invention are suitable as a releasing agent for resin molding, and can impart mold releasability to thermoplastic resins or thermosettable resins to improve the molding cycle.

Polymers (I) to (III) according to the invention have excellent compatibility with rubber and impart mold releasability to rubber, thus being suitable as a rubber processing aid for viscosity adjustment. When used as the rubber processing aid, the polymers improve the dispersibility of fillers and pigments, and impart mold releasability and fluidity to the rubber. Thus, the polymers can improve the molding cycle and extrusion properties upon rubber molding.

Polymers (I) to (III) according to the invention are suitable as a paper quality-improving agent for improving the smoothness of paper and surface modification. When used as a paper quality-improving agent, the polymers can improve the moisture resistance, gloss, surface hardness, anti-blocking property and abrasion resistance, and can impart a high quality feel to the paper, thereby improving durability.

Polymers (I) to (III) according to the invention are suitable as an abrasion resistance-improving agent for ink, and when used as an abrasion resistance-improving agent, the polymers can improve abrasion resistance and heat resistance at the ink surface.

Polymers (I) to (III) according to the invention are suitable as a fiber processing aid, and when used as a fiber processing aid upon fiber resin processing, the polymers can impart flexibility and smoothness to the fiber.

Polymers (I) to (III) according to the invention are suitable as a hot melt additive, and can impart heat resistance and fluidity to hot melt adhesives. The polymers can improve the quality of hot melt adhesives in the areas where heat resistance is required, such as automobiles, construction materials and the like.

Polymers (I) to (III) according to the invention are suitable as an electric insulator, and for example, can improve electric insulating property and heat resistance of film condensers.

Polymers (I) to (III) according to the invention are suitable as an antifogging agent for polyolefin film, and have excellent compatibility with resins, thus inhibiting bleed-out at the resin surface. Specifically, the polymers impart an antifogging effect to films as well as improve durability. Such a polymer containing polyalkylene glycol groups at the terminals is advantageous in the aspect of effectiveness.

Polymers (I) to (III) according to the invention are suitable as a thickening agent (gelling agent) for oily compounds, and are useful for the production of creams, ointments, lotions and gels exclusive to the cosmetic or pharmaceutical fields. When the polymers are used, they have excellent shape retention and thus have stability over time at high temperatures and pigment dispersibility. Also, oily cosmetic materials having good sense of use can be obtained, which can be utilized for medical applications such as sunburn preventing agent, massage oil, lipstick, lip cream and ointment. For the application as the thickening agent (gelling agent) for oily compounds, the polymers can be also used as grease, a thixotropy improving agent and a Theological property improving agent for paints, and they are effective for the prevention of paint-sagging and the adjustment of paint fluidity. Such polymer further containing polyalkylene glycol groups at the terminals is advantageous in the aspect of effectiveness.

Polymers (I) to (III) according to the invention are suitable as a lipid vesicle which remains stably at high temperatures, and can be utilized for the improvement of the consistency of cosmetic compounds such as lipstick and dermatological compounds. Such polymer further containing polyalkylene glycol groups at the terminals is advantageous in the aspect of effectiveness.

Polymers (I) to (III) according to the invention are useful as an excellent hydrophilizing agent for fibers, fabrics, non-woven fabrics, films, molded articles and the like, and can be utilized for the personal hygienic field such as diapers. Such polymer further containing polyalkylene glycol groups at the terminals is advantageous in the aspect of effectiveness, and the effect is exhibited when such polymer is added upon melting of a polymer.

Polymers (I) to (III) according to the invention are useful as an excellent water repellant or anti-fouling agent against low surface tension fluids for thermoplastic resins, particularly for fibers, fabrics, non-woven fabrics, films, molded articles and the like. The polymers can be also utilized in disposable non-woven protective clothing for the medical field and coating field. Examples of the thermoplastic resin include polyolefins, polyesters, polyamides and polyacrylates, in particular. Such polymer further containing perfluoro groups or perfluoroacyl groups at the terminals is advantageous in the aspect of effectiveness, and the effect is manifested when such polymer is added upon melting of a polymer.

Polymers (I) to (III) according to the invention are suitable as a molding aid for agrochemical preparations and the like, and their moderately low water-solubility allows controlled release of the active ingredients of the agrochemicals. Such a polymer further containing polyalkylene glycol groups at the terminals is advantageous in the aspect of effectiveness.

Polymers (I) to (III) according to the invention are suitable as an asphalt additive, and can be used for the production of an asphalt capable of use for heating type pavement materials with excellent anti-peeling property. Such a polymer further containing polyalkylene glycol groups or amines at the terminals is advantageous in the aspect of effectiveness.

EXAMPLES

Hereinafter, the invention will be described in more detail with reference to Examples and the like, but the scope of the invention is not intended to be limited to these Examples and the like.

In addition, the weight average molecular weight Mw and Mw/Mn were measured using GPC according to the method described herein. For the melting point (Tm), the peak top temperature obtained by measuring with DSC was used.

Synthesis Example 1

Synthesis of Double Bond-Terminated Ethylenic Polymer (P-1)

Compound (24) used as catalyst was synthesized according to Synthesis Example 6 of JP-A No. 2003-73412, and double bond-terminated polyethylene at one end was synthesized according to Example 8 of the same publication of patent application.

To a 2000 mL-stainless autoclave thoroughly purged with nitrogen, 1000 mL of heptane was charged at room temperature, and the system was heated to 150° C. Subsequently, the autoclave was pressurized with ethylene to 30 kg/cm$^2$G, and the temperature was maintained. To the autoclave, 0.5 mL (0.5 mmol) of a hexane solution of MMAO (Tosoh Finechem Corporation) (1.00 mmol/mL in terms of aluminum atoms) was fed with pressure, and then 0.5 mL (0.0001 mmol) of a toluene solution (0.0002 mmol/mL) of the following Compound (24) was fed with pressure to initiate polymerization. Under an ethylene gas atmosphere, polymerization was carried out at 150° C. for 30 minutes, and then the polymerization was terminated by feeding a small amount of methanol. The obtained polymer solution was added to 3 liters of methanol containing a small amount of hydrochloric acid to precipitate out the polymer. The polymer was washed with methanol and then dried under reduced pressure at 80° C. for 10 hours.

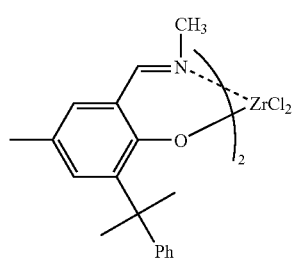

(24)

The obtained polymer product was homopolyethylene, the content of terminal vinyl group at one end (U) was 92% when calculated from $^1$H-NMR measurement of integral value for the terminal methyl group, including the impurity polyethylene saturated at both terminals, $S_A$=3.49, and the integral value for the vinyl group $S_B$=3.00. The results of the $^1$H-NMR measurement and the properties of double bond-terminated ethylenic polymer (P-1) (single product) were as follows.

$^1$H-NMR δ(C$_6$D$_6$) 0.81 (t, 3H, J=6.9 Hz), 1.10-1.45 (m), 1.93 (m, 2H), 4.80 (dd, 1H, J=9.2, 1.6 Hz), 4.86 (dd, 1H, J 17.2, 1.6 Hz), 5.60-5.72 (m, 1H)

Melting point (Tm) 123° C.
Mw=1900, Mw/Mn=2.24 (GPC)

Synthesis Example 2

Synthesis of Epoxy-Terminated Polymer (E-1)

100 g of the above-described double bond-terminated ethylenic polymer (P-1) (108 mmol of vinyl group in terms of Mn 850), 300 g of toluene, 0.85 g (2.6 mmol) of Na$_2$WO$_4$, 0.60 g (1.3 mmol) of CH$_3$(nC$_8$H$_{17}$)$_3$NHSO$_4$, and 0.11 g (1.3 mmol) of phosphoric acid were introduced into a 500-mL separable flask, and were heated under reflux with stirring for 30 minutes to completely melt the polymer product. After adjusting the internal temperature to 90° C., 37 g (326 mmol) of aqueous 30 wt % hydrogen peroxide was added dropwise over 3 hours and then stirred at internal temperature of 90 to 92° C. for 3 hours. Subsequently, with the temperature being maintained at 90° C., 34.4 g (54.4 mmol) of aqueous 25 wt % sodium thiosulfate was added and stirred for 30 minutes, and it was confirmed with a peroxide test paper that the peroxide in the system was completely decomposed. Subsequently, at internal temperature of 90° C., 200 g of dioxane was added to crystallize the product, and the solids were collected by filtration and washed with dioxane. The obtained solids were stirred in aqueous 50% methanol at room temperature, and the solids were collected by filtration and washed with methanol. The aforementioned solids were further stirred in 400 g of methanol, collected by filtration and washed with methanol. The solids were dried at room temperature under reduced pressure of 1 to 2 hPa, and thus 96.3 g of epoxy-terminated polymer (E-1) as a white solid (yield 99%, olefin conversion rate 100%).

This epoxy-terminated polymer (E-1) was subjected to $^1$H-NMR measurement, and it was found from the integral value for the terminal methyl group (shift value: 0.88 ppm), including the impurity polyethylene saturated at both terminals, $S_C$=3.6, and the integral value for the methylene group and methyne group at the base of the epoxy group (shift value: 2.38, 2.66, 2.80-2.87 ppm), $S_D$=3.0, $S_E$=0, that the content of the terminal epoxy group (Ep) was 90%. The results of the $^1$H-NMR measurement and the properties of the terminal epoxy group-containing polymer (E-1) (single product) were as follows.

$^1$H-NMR δ(C$_2$D$_2$Cl$_4$) 0.88 (t, 3H, J=6.92 Hz), 1.18-1.66 (m), 2.38 (dd, 1H, J=2.64, 5.28 Hz), 2.66 (dd, 1H, J=4.29, 5.28 Hz) 2.80-2.87 (m, 1H)

Melting temperature (Tm) 121° C.
Mw=2058, Mw/Mn=1.84 (GPC)

Structural Formula of the Epoxy-Terminated Polymer (E-1):

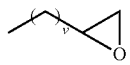

(25)

Synthesis Example 3

Synthesis of Double Bond-Terminated Ethylenic Polymer (P-2)

15.4 g (56.1 mmol) of 5-chloro-3-cumylsalicylaldehyde, 60 mL of toluene and 4.42 g (40% methanol solution, 56.9 mmol) of methylamine were introduced into a sufficiently dried and nitrogen-purged 100-mL reactor, and were stirred at room temperature for 5 hours. This reaction solution was concentrated under reduced pressure to obtain 16.0 g (yield 99%) of a red-brown oil represented by the following Formula (26).

$^1$H-NMR δ(CDCl$_3$) 1.71 (s, 6H), 3.33 (s, 3H), 7.10-7.44 (m, 7H), 8.16 (s, 1H), 13.8 (s, 1H)

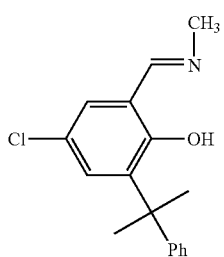

(26)

12.1 g (42.0 mmol) of the Compound (26) and 150 mL of diethyl ether were introduced into a sufficiently dried and argon-purged 500-mL reactor, cooled to −78° C. and stirred. 27.8 mL (n-hexane solution, 1.57 M, 43.7 mmol) of n-butyllithium was added dropwise thereto over 30 minutes, and the mixture was stirred at the same temperature for 2 hours, slowly heated to room temperature and stirred for another 3 hours at room temperature to prepare a lithium salt. This solution was added dropwise to 150 mL of a tetrahydrofuran solution containing 4.84 g (20.8 mol) of $ZrCl_4(THF)_2$ complex cooled to −78° C. After completion of dropwise addition, stirring was continued while the temperature was slowly elevated to room temperature. After stirring for further 12 hours at room temperature, the reaction liquid was distilled to remove the solvent. The obtained solids were dissolved in 200 mL of methylene chloride, and the insolubles were removed with a glass filter. The filtrate was concentrated under reduced pressure, and the precipitated solids were re-immersed in 80 mL of diethyl ether and 150 mL of n-hexane and dried under reduced pressure to obtain 11.4 g (yield 75%) of a compound represented by the following Formula (27) as a yellow powder.

$^1$H-NMR δ($CDCl_3$) 1.67 (s, 6H), 1.92 (s, 6H), 2.30 (s, 6H), 7.00-7.60 (m, 12H), 7.70 (s, 2H), 7.79 (s, 2H)

FD-mass analysis: 734

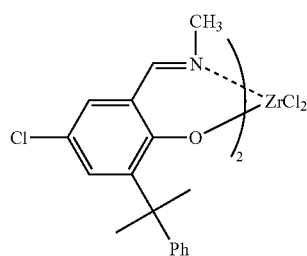

(27)

To a 1000 mL-stainless autoclave thoroughly purged with nitrogen, 450 mL of heptane was introduced and 100 liters/hr of propylene was flowed in at room temperature for 15 minutes to saturate the liquid phase and the gas phase, and the system was heated to 80° C. Subsequently, the autoclave was pressurized with propylene to 4 kg/cm$^2$G, and the temperature was maintained. Ethylene was further introduced to reach 8 kg/cm$^2$G, and the temperature was maintained. To the autoclave, 0.25 mL (0.25 mmol) of a hexane solution of MMAO (Tosoh Finechem Corporation) (1.00 mmol/mL in terms of aluminum atoms) was fed with pressure, and then 1.0 mL (0.0003 mmol) of a toluene solution (0.0003 mmol/mL) of Compound (27) was fed with pressure to initiate polymerization. Under an ethylene gas atmosphere, polymerization was carried out at 80° C. for 15 minutes, and then the polymerization was terminated by feeding 5 mL of methanol. The solvent in the obtained polymer slurry was distilled off to obtain the product. After drying under reduced pressure at 80° C. for 10 hours, 38.86 g of the copolymer was obtained. The polymerization activity was 518 kg/mmol-Zr·h, and the product had Mw=1380 and Mw/Mn=2.20 as calculated in terms of polyethylene, and the content of terminal vinyl group at one end measured by $^1$H-NMR was 99 mol %. The properties were as follows.

$^1$H-NMR δ($C_6D_6$) 0.81 (t, 3H, J=6.9 Hz), 1.10-1.45 (m), 1.95 (m, 2H), 4.84 (dd, 1H, J=9.2, 1.6 Hz), 4.91 (dd, 1H, J=17.2, 1.6 Hz), 5.67-5.78 (m, 1H)

Melting point (Tm) 116° C.

Mw=1490, Mw/Mn=2.5 (GPC)

Content of terminal vinyl group at one end=99% (calculated from $^1$H-NMR).

Synthesis Example 4

Synthesis of Epoxy-Terminated Polymer (E-2)

Epoxy-terminated polymer (E-2) was obtained in the same manner as in Synthesis Example 2, except that the starting material was changed to the above-described homopolyethylene. The properties were as follows.

$^1$H-NMR δ($C_2D_2Cl_4$) 0.88 (t, 3H, J=6.6 Hz), 1.04-1.50 (m), 2.38 (dd, 1H, J=2.6, 5.3 Hz), 2.66 (dd, 1H, J=4.0, 5.3 Hz), 2.80-2.87 (m, 1H)

Melting point (Tm) 119° C.

Mw=1583, Mw/Mn=1.84 (GPC)

Hardness (degree of penetration) 0.1 mm

Melt viscosity 86 cp (140° C.)

Softening point 125° C.

Temperature for 5% weight reduction 323° C. (TGA)

Content of terminal epoxy group=98% (calculated from $^1$H-NMR).

Synthesis Example 5

Synthesis of Double Bond-Terminated Ethylenic Polymer (P-3)

[Preparation of Solid Component (A)]

Under a nitrogen flow, 30 g of silica ($SiO_2$) dried at 150° C. for 5 hours was suspended in 466 mL of toluene, and then 134.3 mL of a solution of methylaluminoxane in toluene (3.08 mmol/mL in terms of Al atoms) was added dropwise at 25° C. over 30 minutes. After completion of the dropwise addition, the temperature was elevated to 114° C. over 30 minutes, and reaction was carried out at that temperature for 4 hours. Subsequently, the temperature was decreased to 60° C., and the supernatant liquid was removed by decantation. The solid component thus obtained was washed three times with toluene, and then toluene was added to prepare a slurry of the solid component (A) in toluene. A portion of the obtained solid component (A) was taken to examine the concentration, and it was found that the slurry concentration was 0.150 g/mL, and the Al concentration was 1.179 mmol/ml.

[Preparation of Solid Catalyst Component (B)]

150 mL of toluene was placed in a nitrogen-purged 300-mL glass flask, and the above-prepared toluene slurry of the solid component (A) (1.91 g in terms of the solid portion) was introduced therein with stirring. Subsequently, 50.0 mL of a toluene solution of Compound (24) (0.0012 mmol/mL in terms of Zr atoms) was added dropwise over 15 minutes, and the mixture was allowed to react at room temperature for 1 hour. Then, the supernatant liquid was removed by decantation, the remaining portion was washed three times with heptane, and 100 mL of heptane was added thereto to prepare a slurry of the solid catalyst component (B) in heptane. A portion of the obtained heptane slurry of the solid catalyst component (B) was taken to examine the concentration, and it was found that the Zr concentration was 0.058 mmol/ml, and the Al concentration was 14.8 mmol/ml.

450 mL of heptane was introduced into a 1000 mL stainless autoclave which had been sufficiently purged with nitrogen, and 100 liters/hr of ethylene was flowed in at room temperature for 15 minutes to saturate the liquid phase and the gas phase. Subsequently, 23 NL of propylene was introduced, and the temperature was elevated to 80° C. Then, the pressure was increased to 8 kg/cm$^2$G with ethylene, and the temperature was maintained. To the autoclave, 0.5 mL (0.5 mmol) of a solution of triisobutylaluminum in decane (1.00 mmol/mL in terms of aluminum atoms) was fed with pressure, and then 0.0001 mmol of the solid catalyst component. (B) in terms of Zr atoms was fed with pressure to initiate polymerization. While the pressure was maintained by continuously supplying ethylene gas, polymerization was carried out at 80° C. for 60 minutes, and then 5 mL of methanol was fed with pressure to terminate the polymerization. After cooling, the monomer was depressurized. The obtained polymer slurry was mixed with 2 L of methanol with stirring and then filtered. The resulting product was dried under reduced pressure at 80° C. for 10 hours to obtain 53.2 g of double bond-terminated polymer (P-3) which is an ethylene-propylene copolymer. The product had Mw=1730, Mw/Mn=1.68, and a melting point of 108° C., and the ratio of vinyl group/vinylene group/vinylidene group as measured by $^1$H-NMR was 78.4/17.6/3.9.

Synthesis Example 6

Synthesis of Double Bond-Terminated Ethylenic Polymer (P-4)

The polymerization was carried out in the same manner as in Synthesis Example 5, except that the amount of propylene introduced was changed to 28 NL, to obtain 41.4 g of double bond-terminated polymer (P-4) which is an ethylene-propylene copolymer. The product had Mw=1310, Mw/Mn=1.66, and a melting point of 97.5° C., and the ratio of vinyl group/vinylene group/vinylidene group as measured by $^1$H-NMR was 70.6/24.6/4.8.

Synthesis Example 7

Synthesis of Epoxy-Terminated Polymer (E-3)

The same operation as in Synthesis Example 2 was carried out, except that the double bond-terminated polymer was changed to terminal unsaturated ethylene-propylene copolymer (P-3) obtained in Synthesis Example 5 (Mw=1730, Mn=994), to obtain 23.9 g (olefin conversion rate 100%, yield 94%) of epoxy-terminated polymer (E-3) as a white solid.

$^1$H-NMR δ(C$_2$D$_2$Cl$_4$) 0.80-0.88 (m), 0.9-1.6 (m), 2.37-2.40 (1H, dd, J=2.64, 5.28 Hz), 2.50 (m), 2.66 (1H, dd, J=3.96, 5.28 Hz), 2.80-2.86 (1H, m), 2.94 (m)
Mw=1720, Mw/Mn=1.58 (GPC)
Melting point (Tm) 99.7° C.
Hardness (degree of penetration) 0.2 mm
Melt viscosity 32 cp (140° C.)
Softening point 114.5° C.
Temperature for 5% weight reduction 334° C. (TGA).

Synthesis Example 8

Synthesis of Epoxy-Terminated Polymer (E-4)

The same operation as in Synthesis Example 2 was carried out, except that the double bond-terminated polymer was changed to the terminal unsaturated ethylene-propylene copolymer (P-4) obtained in Synthesis Example 6 (Mw=1310, Mn=790), to obtain 9.53 g (olefin conversion rate 100%, yield 94%) of epoxy polymer (E-4) as a white solid.

$^1$H-NMR δ(C$_2$D$_2$Cl$_4$) 0.80-0.88 (m), 0.9-1.6 (m), 2.37-2.40 (1H, dd, J=2.97, 5.28 Hz), 2.50 (m), 2.66 (1H, dd, J=3.96, 5.28 Hz), 2.80-2.86 (1H, m), 2.95 (m)
Mw=1470, Mw/Mn=1.54 (GPC)
Melting point (Tm) 73.6° C.
Melt viscosity 19 cp (140° C.)
Softening point 101.5° C.
Temperature for 5% weight reduction 322° C. (TGA).

Example 1

Preparation of α,β-dihydroxy Polymer (D-1)

100 g of double bond-terminated polymer (P-1) obtained in Synthesis Example 1 (108 mmol of vinyl group in terms of Mn 850), 300 g of toluene, 1.79 g (5.4 mmol) of Na$_2$WO$_4$, 1.27 g (2.7 mmol) of CH$_3$(nC$_8$H$_{17}$)$_3$NHSO$_4$ and 0.23 g (2.7 mmol) of phosphoric acid were introduced into a 1000-mL separable flask and heated under reflux for 30 minutes with stirring to completely melt the polymer product. The internal temperature was adjusted to 90° C., then 37 g (326 mmol) of aqueous 30 wt % hydrogen peroxide was added dropwise over 3 hours, and then the mixture was stirred at internal temperature of 90 to 92° C. for 3 hours. It was confirmed from $^1$H-NMR that the terminal olefins were 100% converted to epoxy groups. Subsequently, keeping the temperature at 90° C., 34.4 g (54.4 mmol) of aqueous 25 wt % sodium thiosulfate was added and stirred for 30 minutes. It was confirmed by using a peroxide test paper that the peroxide in the system was completely decomposed. After the reaction mixture was cooled to 80° C., 2-propanol was slowly added over 30 minutes to crystallize the product. The slurry liquid was stirred at 65° C. for 1 hour, and then the solids were collected by filtration and washed with 2-propanol. The obtained solids were stirred in aqueous 50 wt % methanol solution at room temperature, and the solids were collected by filtration and washed with methanol. The solids were further stirred in 400 g of methanol, collected by filtration and washed with methanol. The solids were dried at 60° C. under reduced pressure of 1 to 2 hPa to obtain 106.6 g of a polymer having hydroxyl groups for both X and Y with respect to Formula (14) (A: the group formed by ethylene polymerization (Mw=2015), R: hydrogen atom), namely, an α,β-dihydroxy polymer (D-1) as a white solid (yield 99%, olefin conversion rate 100%, epoxy conversion rate 100%). The properties are as follows.

$^1$H-NMR δ(C$_2$D$_2$Cl$_4$) 0.89 (t, 3H, J=6.9 Hz), 1.05-1.84 (m), 3.41 (dd, 1H, J=5.9, 9.9 Hz), 3.57-3.63 (m, 2H)
Melting point (Tm) 122° C.
Hardness (degree of penetration) 0 mm
Melt viscosity 214 cp (140° C.)
Softening point 129° C.
Temperature for 5% weight reduction 297° C. (TGA).

Example 2

Preparation of α,β-dihydroxy Polymer (D-2)

The reaction was carried out in the same manner as in Example 1, except that double bond-terminated ethylenic polymer (P-1) of the starting materials was changed to the double bond-terminated ethylene polymer (P-2), to obtain a polymer having hydroxyl groups for both X and Y with respect to Formula (14) (A: a group formed by ethylene polymerization (Mw=1540), R: hydrogen atom), namely, an α,β-dihydroxy polymer (D-2). The properties are as follows.

$^1$H-NMR δ(C$_2$D$_2$Cl$_4$) 0.88 (t, 3H, J=6.9 Hz), 1.13-1.70 (m), 3.41 (dd, 1H, J=6.9, 10.9 Hz), 3.57-3.63 (m, 2H)
Melting point (Tm) 119° C.
Hardness (degree of penetration) 0.1 mm
Softening point 125.5° C.
Melt viscosity 84 cp (140° C.)
Temperature for 5% weight reduction 366.4° C. (TGA).

Example 3

Synthesis Example 1 for Polyether Resin 98.6 g (88 mmol) of epoxy-terminated polymer (E-1) obtained in Synthesis Example 2 (Mn=1119), 30.6 g (51 mmol) of polyethylene glycol (PEG) 600 (Mn=598) and 434 g of toluene were introduced all at once into a flask equipped with a thermometer, a stirring rod, a nitrogen inlet tube and a condenser, and the temperature was elevated to 130° C. Azeotropic dehydration was carried out while distilling toluene. After distilling off 147 g of toluene, the temperature was lowered to 110° C., 1.4 g (9.9 mmol) of boron trifluoride diethyl ether complex was added, and the mixture was allowed to react for 11 hours. Subsequently, the reaction liquid was added dropwise into 790 g of methanol, and a white solid was precipitated out.

This white solid was filtered, washed with methanol and dried to obtain 108.7 g of Copolymer (1). This Copolymer (1) was subjected to $^1$H-NMR, and it was found from a comparison of the integral value for the terminal methyl group derived from the epoxy-terminated polymer (E-1) (shift value: 0.88 ppm) and the integral value for the alkylene group of PEG600 (shift value: 3.52-3.79 ppm), that the copolymer had a composition of epoxy-terminated polymer (E-1): PEG600=2 moles: 1 mole. It was found from the measurement of $^{13}$C-NMR that carbons bound to the PEG600 terminal hydroxyl groups (shift value: 61.7 ppm) existed, and from the fact that the integral value for the carbon was about a half of the integral value for the carbons of the terminal methyl group derived from the epoxy-terminated polymer (E-1) (shift value: 13.8 ppm), it was found that the polymer was made by bimolecular ring-opening polymerization of the epoxy-terminated polymer (E-1) at one end of PEG. The properties are as follows.

$^1$H-NMR δ($C_2D_2Cl_4$) 0.88 (t, 6H, J=6.6 Hz), 1.00-1.57 (m), 3.52-3.79 (m, 52H)

The analysis results of $^{13}$C-NMR are shown below.

$^{13}$C-NMR: δ($C_6D_4Cl_2$) 13.8, 22.6, 25.6, 29.2, 29.3, 29.6, 29.7, 29.9, 31.9, 33.6, 61.7, 64.7, 69.1, 70.3, 70.5, 70.6, 70.7, 71.1, 72.6, 76.0, 81.3

Melting point (Tm) 121° C.

Example 4

Synthesis Example 2 for Polyether Resin 6.13 g (10.25 mmol) of PEG600 (Mn=598), 19.73 g (17.6 mmol) of the epoxy-terminated polymer (E-1) (Mn=1119) and 69 g of toluene were introduced all at once into a flask equipped with a thermometer, a stirring rod, a nitrogen inlet tube and a condenser, and the temperature was elevated to 130° C. Azeotropic dehydration was carried out while distilling toluene. After distilling off 19 g of toluene, the temperature was decreased to 110° C., 0.56 g (3.9 mmol) of boron trifluoride diethyl ether complex was added, and the mixture was allowed to react for 7.5 hours. Subsequently, the reaction liquid was added dropwise in 158 g of methanol, and a white solid was precipitated out.

This white solid was filtered, washed with methanol and dried to obtain 20.1 g of Copolymer (2). This Copolymer (2) was subjected to $^1$H-NMR, and it was found from a comparison of the integral value for the terminal methyl group derived from the epoxy-terminated polymer (E-1) (shift value: 0.88 ppm) and the integral value for the alkylene group of PEG600 (shift value: 3.52-3.79 ppm), that the copolymer had a composition of epoxy-terminated polymer (E-1): PEG600=4 moles: 1 mole. The properties are as follows.

$^1$H-NMR δ($C_2D_2Cl_4$) 0.88 (t, 12H, J=6.6 Hz), 1.00-1.57 (m), 3.52-3.79 (m, 52H)

Melting point (Tm) 121° C.

Example 5

Synthesis Example 3 for Polyether Resin 17.9 g (17.9 mmol) of PEG1000 (Mn=1000) and 6.7 g (35.8 mmol) of aqueous 30 wt % KOH solution were introduced all at once into a flask equipped with a thermometer, a stirring rod, a nitrogen inlet tube and a condenser, and the temperature was elevated to 100° C. to carry out dehydration. After the dehydration, the temperature was elevated to 120° C., and 30.7 g (27 mmol) of the epoxy-terminated polymer (E-1) (Mn=1119) was added. The mixture was allowed to react for 18 hours, and then at 120° C., the reaction product was taken out and cooled.

After cooling, 100 mL of distilled water was added to the obtained solid, and hydrochloric acid was added dropwise to conduct neutralization. After the neutralization, the solid was filtered, washed with distilled water and dried to obtain 34.8 g of Copolymer (3) as a white solid. This Copolymer (3) was subjected to $^1$H-NMR measurement, and it was found from a comparison of the integral value for the terminal methyl group derived from the epoxy-terminated polymer (E-1) (shift value: 0.88 ppm) and the integral value for the alkylene group of PEG1000 (shift value: 3.52-3.65 ppm), that the copolymer had a composition of epoxy-terminated polymer (E-1): PEG1000=4 moles: 1 mole. It was also found from atomic absorption spectrometry that the copolymer contained 1.3% by weight of K fraction. The properties are as follows.

$^1$H-NMR δ($C_2D_2Cl_4$) 0.88 (t, 12H, J=6.6 Hz), 1.18-1.5 (m), 3.52-3.65 (m, 90H)

Melting point (Tm) 124° C.

Example 6

Synthesis Example 4 for Polyether Resin

The reaction was carried out in the same manner as in Example 3, except that PEG1000 was used instead of PEG600 in Example 3, to obtain Copolymer (4). This Copolymer (4) was subjected to $^1$H-NMR measurement, and it was found that the copolymer had a composition of epoxy-terminated polymer (E-1): PEG1000=2 moles: 1 mole. The properties are as follows.

$^1$H-NMR δ($C_2D_2Cl_4$) 0.88 (t, 6H, J=6.6 Hz), 1.18-1.5 (m), 3.52-3.65 (m, 90H)

Example 7

Synthesis Example 5 for Polyether Resin

The reaction was carried out in the same manner as in Example 4, except that the epoxy-terminated polymer (E-3) was used instead of epoxy-terminated polymer (E-1) in Example 4, to obtain Copolymer (5). This Copolymer (5) was subjected to $^1$H-NMR measurement, and it was found that the copolymer had a composition of epoxy-terminated polymer (E-3): PEG600=4 moles: 1 mole. The properties are as follows.

$^1$H-NMR δ($C_2D_2Cl_4$) 0.82-0.92 (m), 1.00-1.70 (m), 3.25-3.76 (m)

Melting point (Tm) 108° C.

Example 8

Synthesis Example for Polyurethane Resin 5.03 g (8.36 mmol) of PEG600 (Mn=598), 3.5 g (ca 0.7 mmol) of Copolymer (2) (Mn=ca 5000), and 40 g of toluene were introduced all at once into a flask equipped with a thermometer, a stirring rod, a nitrogen inlet tube and a condenser, and the temperature was elevated to 130° C. Azeotropic dehydration was carried out while distilling toluene. After distilling off 13 g of toluene, the temperature was lowered to 110° C., 1.58 g (9.4 mmol) of hexamethylene diisocyanate and 0.01 g of dibutyltin dilaurate as a catalyst were added, and the mixture was allowed to react for 3.5 hours. Subsequently, the reaction liquid was concentrated in an evaporator to obtain 9.39 g of Copolymer (6). This Copolymer (6) was a thermoplastic polyurethane resin. This Copolymer (6) was subjected to $^1$H-NMR measurement, and it was found from a comparison of the integral value for the terminal methyl group derived from the epoxy-terminated polymer (E-1) (shift value: 0.86 ppm) and the integral value for the methylene group adjacent to the nitrogen atom in a carbamate bond (shift value: 3.10 ppm), and from a comparison of the integral value for the terminal methyl group of the epoxy-terminated polymer (E-1) (shift value: 0.86 ppm) and the integral value for the methylene group adjacent to the oxygen atom in a carbamate bond (shift value: 4.14 ppm), that the copolymer had a composition of Copolymer (2): hexamethylene diisocyanate: PEG600=1 mole: 13 moles: 12 moles. The properties are as follows.

$^1$H-NMR $\delta(C_2D_2Cl_4)$ 0.86 (t, 12H, J=6.6 Hz), 1.05-1.4 (m), 1.47 (t, 50H, J=5.6 Hz), 3.10 (t, 50H, J=5.6 Hz), 3.4-3.74 (m), 4.14 (t, 50H, J=5.6 Hz)

Melting point (Tm) 121° C.

Example 9

The epoxy-terminated polymer (E-1) synthesized in Synthesis Example 2 was used as a starting material.

4.18 g (11.3 mmol) of decamethylcyclopentasiloxane, 3.0 g of xylene and 0.23 g of KOH were introduced into a 25-mL flask, and heated to a temperature of 120° C. After confirming that KOH was dissolved, 1.0 g of the epoxy-terminated polymer (E-1) (0.89 mmol in terms of Mn 1100) was added to the solution, and the mixture was stirred at 120° C. for 20 hours. Subsequently, a small amount of 85% phosphoric acid was added to terminate the reaction. After cooling, acetone was added to crystallize the reaction product, and then the mixture was left to stand for about 30 minutes to precipitate a solid. The supernatant liquid was removed by decantation. This operation was repeated several times, and the obtained entity was dried under reduced pressure to obtain 1.2 g of a pale yellow solid at an epoxy conversion rate of 100%. This polyolefin-containing polysiloxane (1) was subjected to $^{29}$Si-NMR measurement, and it was found from the absence of a terminal silanol group that a polyethylene chain (A) derived from the epoxy-terminated polymer (E-1) and a polysiloxane chain (B) formed an A-B-A block copolymer. The polyolefin-containing polysiloxane was also subjected to $^1$H-NMR measurement, and it was found from a comparison of the integral value for the terminal methyl group derived from the epoxy-terminated polymer (E-1) (shift value: 0.88 ppm) and the integral value for the methyl group derived from dimethylsiloxane (shift value: 0.07 ppm), that the number of siloxane segments (m) was 55. Thus, the obtained polyolefin-containing polysiloxane (1) had following structure with respect to Formula (9).

A: a group formed by ethylene polymerization (Mw=2015), R: hydrogen atom, $R^5$, $R^6$: methyl group, G: group represented by Formula (10) (A: a group formed by ethylene polymerization (Mw=2015), R: hydrogen atom), m: 55.

The properties are as follows.

$^1$H-NMR $\delta(C_2D_2Cl_4)$ 0.07 (s, 332H), 0.89 (t, 6H, J=6.9 Hz), 1.00-1.85 (m), 3.30 (dd, 2H, J=5.6, 9.6 Hz), 3.58 (m, 4H)

$^{29}$Si-NMR $\delta(C_2D_2Cl_4)$ −22 ppm

Melting point (Tm) 122° C.

Example 10

As the starting material, the α,β-dihydroxy polymer (D-1) synthesized in Example 1 was used.

1.0 g of the α,β-dihydroxy polymer (D-1) (0.91 mmol in terms of Mn 1100), 4.18 g (11.3 mmol) of decamethylcyclopentasiloxane, 3.0 g of octane and 0.10 g (0.67 mmol) of CsOH were introduced into a 25-mL flask, heated to a temperature of 120° C., and stirred for 20 hours. Then, a small amount of 85% phosphoric acid was added to terminate the reaction. After cooling, acetone was added to crystallize the reaction product, then the mixture was left to stand for about 30 minutes to precipitate a solid, and the supernatant liquid was removed by decantation. This operation was repeated several times, and the obtained entity was dried under reduced pressure to obtain 1.3 g of a polyolefin-containing polysiloxane having an average number of siloxane segments (m) of 80 (with respect to Formula (9), A: a group formed by ethylene polymerization (Mw=2015), R: hydrogen atom, $R^5$, $R^6$: methyl group, G: group represented by Formula (10) (A: a group formed by ethylene polymerization (Mw=2015), R: hydrogen atom), m: 80) as a pale yellow solid at an epoxy conversion rate of 100%. The properties are as follows.

$^1$H-NMR $\delta(C_2D_2Cl_4)$ 0.07 (s, 480H), 0.89 (t, 6H, J=6.9 Hz), 1.00-1.85 (m), 3.30 (dd, 2H, J=5.6, 9.6 Hz), 3.58 (m, 4H)

$^{29}$Si-NMR $\delta(C_2D_2Cl_4)$ −22 ppm

Melting point (Tm) 120° C.

Example 11

The reaction was carried out in the same manner as in Example 9, except that 85% phosphoric acid was used instead of KOH in Example 9, to obtain a polyolefin-containing polysiloxane having an average number of siloxane segment (m) of 13 (with respect to Formula (9), A: a group formed by ethylene polymerization (Mw=2015), R: hydrogen atom, $R^5$, $R^6$: methyl group, G: group represented by Formula (10) (A: a group formed by ethylene polymerization (Mw=2015), R: hydrogen atom), m: 13) at an epoxy conversion rate of 100%. The properties are as follows.

$^1$H-NMR $\delta(C_2D_2Cl_4)$ 0.07 (s, 76H), 0.89 (t, 6H, J=6.9 Hz), 1.00-1.85 (m), 3.30 (dd, 2H, J=6.9, 10.9 Hz), 3.58 (m, 4H)

$^{29}$Si-NMR $\delta(C_2D_2Cl_4)$ −22 ppm

Melting point (Tm) 121° C.

Example 12

The reaction was carried out in the same manner as in Example 9, except that the epoxy-terminated polymer (E-2) was used instead of the epoxy-terminated polymer (E-1) in Example 9, to obtain a polyolefin-containing polysiloxane having an average number of siloxane segments (m) of 108 (with respect to Formula (9), A: a group formed by ethylene polymerization (Mw=1540), R: hydrogen atom, $R^5$, $R^6$: methyl group, G: group represented by Formula (10) (A: a group formed by ethylene polymerization (Mw=1540), R: hydrogen atom), m: 108) at an epoxy conversion rate of 100%. The properties are as follows.

$^1$H-NMR $\delta(C_2D_2Cl_4)$ 0.07 (s, 646H), 0.89 (t, 6H, J=6.9 Hz), 1.00-1.85 (m), 3.30 (dd, 2H, J=6.9, 10.6 Hz), 3.58 (m, 4H)

Melting point (Tm) 118° C.

Example 13

The reaction was carried out in the same manner as in Example 10, except that the α,β-dihydroxy polymer (D-2)

was used instead of the α,β-dihydroxy polymer (D-1) in Example 10, to obtain a polyolefin-containing polysiloxane having an average number of siloxane segments (m) of 117 (with respect to Formula (9), A: a group formed by ethylene polymerization (Mw=1540), R: hydrogen atom, $R^5$, $R^6$: methyl group, G: group represented by Formula (10) (A: a group formed by ethylene polymerization (Mw=1540), R: hydrogen atom), m: 117) at an epoxy conversion rate of 100%. The properties are as follows.

$^1$H-NMR δ($C_2D_2Cl_4$) 0.07 (s, 704H), 0.89 (t, 6H, J=6.9 Hz), 1.00-1.85 (m), 3.30 (dd, 2H, J=6.9, 10.6 Hz), 3.58 (m, 4H)

Melting point (Tm) 119° C.

Example 14

The reaction was carried out in the same manner as in Example 9, except that the epoxy-terminated polymer (E-3) obtained in Synthesis Example 7 was used instead of the epoxy-terminated polymer (E-1) in Example 9, to obtain a polyolefin-containing polysiloxane having an average number of siloxane segments (m) of 9 (with respect to Formula (9), A: a group formed by copolymerization of ethylene and propylene (Mw=1697), R: hydrogen atom, $R^5$, $R^6$: methyl group, G: group represented by Formula (10) (A: a group formed by copolymerization of ethylene and propylene (Mw=1697), R: hydrogen atom), m: 9) at an epoxy conversion rate of 100%, from a comparison of the integral value for the protons at the base of the hydroxyl group generated by the reaction between the epoxy-terminated polymer (E-3) and a cyclic polysiloxane (shift value: 3.39 ppm) and the integral value for the methyl group derived from dimethylsiloxane (shift value: 0.07 ppm).

$^1$H-NMR δ($C_2D_2Cl_4$) 0.07 (s, 53H), 0.8-1.8 (m), 1.00-1.85 (m), 3.39 (dd, 2H, J=6.9, 10.8 Hz), 3.58 (m, 4H)

Melting point (Tm) 111° C.

Example 15

The reaction was carried out in the same manner as in Example 9, except that the epoxy-terminated polymer (E-4) obtained in Synthesis Example 8 was used instead of the epoxy-terminated polymer (E-1) in Example 9, to obtain a polyolefin-containing polysiloxane having an average number of siloxane segments (m) of 5 (with respect to Formula (9), A: a group formed by copolymerization of ethylene and propylene (Mw=1267), R: hydrogen atom, $R^5$, $R^6$: methyl group, G: group represented by Formula (10) (A: a group formed by copolymerization of ethylene and propylene (Mw=1267), R: hydrogen atom), m: 5) at an epoxy conversion rate of 100%.

$^1$H-NMR δ($C_2D_2Cl_4$) 0.07 (s, 27H), 0.8-1.8 (m), 1.00-1.85 (m), 3.39 (dd, 2H, J=6.9, 10.9 Hz), 3.58 (m, 4H)

Melting point (Tm) 105° C.

Example 16

The epoxy-terminated polymer (E-1) synthesized in Synthesis Example 2 was used as the starting material.

100 g (250 mmol) of polyethylene glycol (average molecular weight 400) and 70 g of toluene were introduced into a 500-mL separable flask, and stirred at 110° C. for 30 minutes. Subsequently, 50 g of the epoxy-terminated polymer (E-1) (45 mmol in terms of Mn 1120) was added to this solution, and the mixture was stirred at 110° C. for 8 hours. Then, 1 mol/L aqueous hydrochloric acid was added to terminate the reaction, acetone was further added to crystallize the reaction product, and then the resulting solid was collected by filtration. The obtained solid was washed with stirring with a mixed solution of a saturated aqueous solution of sodium hydrogen carbonate and acetone, and further washed with stirring one time with an aqueous acetone solution and twice with acetone, and then the resulting solid was collected by filtration. Subsequently, the solid was dried under reduced pressure at room temperature, to obtain 60 g of a corresponding polymer (with respect to Formula (14), A: a group formed by ethylene polymerization (Mw=2015), R: hydrogen atom, one of X and Y being a hydroxyl group and the other being a polyethylene glycol group (average molecular weight 400)) as a white solid, at an epoxy conversion rate of 100%. The properties are as follows.

$^1$H-NMR δ($C_2D_2Cl_4$) 0.87 (t, 3H, J=6.9 Hz), 0.95-1.58 (m), 3.30 (dd, 1H, J=7.6, 9.9 Hz), 3.46 (dd, 1H, J=3.3, 9.9 Hz), 3.53-3.77 (m)

Melting point 121° C.

Example 17

The reaction was carried out in the same manner as in Example 16, except that 2-methoxyethanol was used instead of the polyethylene glycol having an average molecular weight of 400 in Example 16, to obtain a corresponding polymer (with respect to Formula (14), A: a group formed by ethylene polymerization (Mw=2015), R: hydrogen atom, one of X and Y being a hydroxyl group and the other being a 2-methoxyethoxy group) at an epoxy conversion rate of 100%. The properties are as follows.

$^1$H-NMR δ($C_2D_2Cl_4$) 0.88 (t, 3H, J=6.9 Hz), 0.96-1.63 (m), 3.30 (dd, 1H, J=7.6, 9.9 Hz), 3.33 (s, 3H), 3.47 (dd, 1H, J=3.3, 9.9 Hz), 3.47-3.54 (m, 2H), 3.58-3.64 (m, 2H), 3.67-3.77 (m, 1H)

IR (cm$^{-1}$) 3430, 2919, 1474, 1116, 719

Melting point (Tm) 121° C.

Example 18

The reaction was carried out in the same manner as in Example 16, except that tetraethylene glycol was used instead of the polyethylene glycol having an average molecular weight of 400 in Example 16, to obtain a corresponding polymer (with respect to Formula (14), A: a group formed by ethylene polymerization (Mw=2015), R: hydrogen atom, one of X and Y being a hydroxyl group and the other being a 11-hydroxy-3,6,9-trioxaundecyloxy group) at an epoxy conversion rate of 100%. The properties are as follows.

$^1$H-NMR δ($C_2D_2Cl_4$) 0.88 (t, 3H, J=6.9 Hz), 0.97-1.60 (m), 3.30 (dd, 1H, J=7.3, 9.9 Hz), 3.47 (dd, 1H, J=3.3, 9.9 Hz), 3.53-3.77 (m, 17H)

Melting point 120° C.

Example 19

The reaction was carried out in the same manner as in Example 16, except that polyethylene glycol having an average molecular weight of 600 was used instead of the polyethylene glycol having an average molecular weight of 400 in Example 16, to obtain a corresponding polymer (with respect to Formula (14), A: a group formed by ethylene polymerization (Mw=2015), R: hydrogen atom, one of X and Y being a hydroxyl group and the other being a polyethylene glycol group (average molecular weight 600)) at an epoxy conversion rate of 100%. The properties are as follows.

$^1$H-NMR δ($C_2D_2Cl_4$) 0.88 (t, 3H, J=6.9 Hz), 0.96-1.77 (m), 3.30 (dd, 1H, J=7.6, 9.9 Hz), 3.47 (dd, 1H, J=3.3, 9.9 Hz), 3.38-3.80 (m)

Melting point (Tm) 121° C.

Example 20

The reaction was carried out in the same manner as in Example 16, except that polyethylene glycol having an average molecular weight of 1000 was used instead of the polyethylene glycol having an average molecular weight of 400 in Example 16, to obtain a corresponding polymer (with respect to Formula (14), A: a group formed by ethylene polymerization (Mw=2015), R: hydrogen atom, one of X and Y being a hydroxyl group and the other being a polyethylene glycol group (average molecular weight 1000)) at an epoxy conversion rate of 100%. The properties are as follows.

$^1$H-NMR δ($C_2D_2Cl_4$) 0.88 (t, 3H, J=6.9 Hz), 0.95-1.80 (m), 3.30 (dd, 1H, J=7.6, 9.9 Hz), 3.46 (dd, 1H, J=3.3, 9.9 Hz), 3.37-3.79 (m)

Melting point (Tm) 121° C.

Example 21

The reaction was carried out in the same manner as in Example 16, except that polypropylene glycol having an average molecular weight of 400 was used instead of the polyethylene glycol having an average molecular weight of 400 in Example 16, to obtain a corresponding polymer (with respect to Formula (14), A: a group formed by ethylene polymerization (Mw=2015), R: hydrogen atom, one of X and Y being a hydroxyl group and the other being a polypropylene glycol group (average molecular weight 400)) at an epoxy conversion rate of 100%. The properties are as follows.

$^1$H-NMR δ($C_2D_2Cl_4$) 0.88 (t, 3H, J=6.6 Hz), 0.95-1.57 (m), 3.18-3.74 (m), 3.78-3.93 (m, 1H)

Melting point (Tm) 121° C.

Example 22

The reaction was carried out in the same manner as in Example 16, except that polypropylene glycol having an average molecular weight of 1000 was used instead of the polyethylene glycol having an average molecular weight of 400 in Example 16, to obtain a corresponding polymer (with respect to Formula (14), A: a group formed by ethylene polymerization (Mw=2015), R: hydrogen atom, one of X and Y being a hydroxyl group and the other being a polypropylene glycol group (average molecular weight 1000)) at an epoxy conversion rate of 100%. The properties are as follows.

$^1$H-NMR δ($C_2D_2Cl_4$) 0.88 (t, 3H, J=6.6 Hz), 0.95-1.58 (m), 3.17-3.73 (m), 3.78-3.93 (m, 1H)

Melting point (Tm) 121° C.

Example 23

The reaction was carried out in the same manner as in Example 16, except that PolyFox™636 Fluorosurfactant (OMNOVA SOLUTIONS, INC.) represented by the following Formula (28) was used instead of the polyethylene glycol having an average molecular weight of 400, 1,2,4-trichlorobenzene was used instead of toluene and the reaction temperature was changed to 180° C. in Example 16, to obtain a corresponding vicinal-substitution type of functional group-containing polymer (with respect to Formula (14), A: a group formed by ethylene polymerization (Mw=2015), R: hydrogen atom, one of X and Y being a hydroxyl group and the other being a fluorine-containing polyether group) at an epoxy conversion rate of 100%. The properties are as follows.

$^1$H-NMR δ($C_2D_2Cl_4$) 0.88 (t, 3H, J=6.9 Hz), 1.00-1.70 (m), 3.05-3.85 (m)

Melting point (Tm) 121° C.

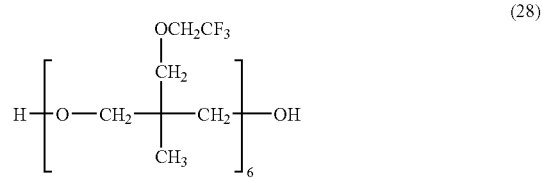

(28)

Example 24

The reaction was carried out in the same manner as in Example 16, except that phenol was used instead of the polyethylene glycol having an average molecular weight of 400 and potassium carbonate was used instead of potassium hydroxide in Example 16, to obtain a corresponding vicinal-substitution type of functional group-containing polymer (with respect to Formula (14), A: a group formed by ethylene polymerization (Mw=2015), R: hydrogen atom, one of X and Y being a hydroxyl group and the other being a phenoxy group) at an epoxy conversion rate of 100%. The properties are as follows.

$^1$H-NMR δ($C_2D_2Cl_4$) 0.88 (t, 3H, J=6.9 Hz), 1.00-1.60 (m), 3.80-3.99 (m, 3H), 6.83-6.88 (m, 3H), 7.19-7.24 (m, 2H)

Melting point (Tm) 121° C.

Example 25

0.85 g of the same epoxy-terminated polymer (E-1) as the one used in Example 16 (0.75 mmol in terms of Mn 1120), 0.50 g (4.8 mmol) of diethanolamine and 1.5 g of toluene were introduced into a 50-mL flask, and stirred at 120° C. for 8 hours. Subsequently, water was added to terminate the reaction, acetone was further added to crystallize the reaction product, and the resulting solid was collected by filtration.

The obtained solid was washed with stirring one time with an aqueous acetone solution and also three times with acetone, and then the resulting solid was collected by filtration. Subsequently, the solid was dried under reduced pressure at room temperature, to obtain 0.86 g of a corresponding polymer (with respect to Formula (14), A: a group formed by ethylene polymerization (Mw=2015), R: hydrogen atom, one of X and Y being a hydroxyl group and the other being a bis(2-hydroxyethyl)amino group) as a white solid, at an epoxy conversion rate of 100%. The properties are as follows.

$^1$H-NMR δ($C_2D_2Cl_4$) 0.88 (t, 3H, J=6.6 Hz), 0.95-1.92 (m), 2.38-2.85 (m, 6H), 3.54-3.71 (m, 5H)

Melting point (Tm) 121° C.

Example 26

The reaction was carried out in the same manner as in Example 25, except that 2-aminoethanol was used instead of diethanolamine in Example 25, to obtain a corresponding polymer (with respect to Formula (14), A: a group formed by ethylene polymerization (Mw=2015), R: hydrogen atom, one of X and Y being a hydroxyl group and the other being a 2-hydroxyethylamino group) at an epoxy conversion rate of 100%. The properties are as follows.

$^1$H-NMR δ($C_2D_2Cl_4$) 0.88 (t, 3H, J=6.6 Hz), 0.97-1.73 (m), 2.50-2.63 (m, 1H), 2.72-2.88 (m, 3H), 3.62-3.73 (m, 3H)

Melting point (Tm) 121° C.

Example 27

The reaction was carried out in the same manner as in Example 25, except that aniline was used instead of diethanolamine in Example 25, to obtain a corresponding polymer (with respect to Formula (14), A: a group formed by ethylene polymerization (Mw=2015), R: hydrogen atom, one of X and Y being a hydroxyl group and the other being a phenylamino group) at an epoxy conversion rate of 100%. The properties are as follows.

$^1$H-NMR δ($C_2D_2Cl_4$) 0.88 (t, 3H, J=6.9 Hz), 0.96-1.62 (m), 3.01 (dd, 1H, J=7.6, 12.9 Hz), 3.23 (dd, 1H, J=3.3, 12.9 Hz), 3.73-3.85 (m, 1H), 6.56-6.72 (m, 3H), 7.05-7.17 (m, 2H)

Melting point (Tm) 121° C.

Example 28

The reaction was carried out in the same manner as in Example 25, except that m-aminophenol was used instead of diethanolamine in Example 25, to obtain a corresponding polymer (with respect to Formula (14), A: a group formed by ethylene polymerization (Mw=2015), R: hydrogen atom, one of X and Y being a hydroxyl group and the other being a 3-hydroxyphenylamino group) at an epoxy conversion rate of 100%. The properties are as follows.

$^1$H-NMR δ($C_2D_2Cl_4$) 0.88 (t, 3H, J=6.6 Hz), 0.97-1.69 (m), 2.98 (dd, 1H, J=8.2, 12.5 Hz), 3.20 (dd, 1H, J=3.0, 12.5 Hz), 3.70-3.83 (m, 1H), 6.06-6.27 (m, 3H), 6.96 (t, 1H, J=7.9 Hz)

Melting point (Tm) 121° C.

Example 29

The reaction was carried out in the same manner as in Example 25, except that p,p'-methylenedianiline was used instead of diethanolamine in Example 25, to obtain a corresponding polymer (with respect to Formula (14), A: a group formed by ethylene polymerization (Mw=2015), R: hydrogen atom, one of X and Y being a hydroxyl group and the other being a 4-(4-aminophenylmethyl)phenylamino group) at an epoxy conversion rate of 100%. The properties are as follows.

$^1$H-NMR δ($C_2D_2Cl_4$) 0.88 (t, 3H, J=6.6 Hz), 0.95-1.61 (m), 2.98 (dd, 1H, J=7.6, 12.9 Hz), 3.20 (dd, 1H, J=4.0, 12.9 Hz), 3.72 (s, 2H), 3.60-3.74 (m, 1H), 6.50-6.59 (m, 4H), 6.88-6.98 (m, 4H)

Melting point (Tm) 121° C.

Example 30

The reaction was carried out in the same manner as in Example 25, except that ethylenediamine was used instead of diethanolamine in Example 25, to obtain a corresponding polymer (with respect to Formula (14), A: a group formed by ethylene polymerization (Mw=2015), R: hydrogen atom, one of X and Y being a hydroxyl group and the other being a 2-aminoethylamino group) at an epoxy conversion rate of 100%. The properties are as follows.

$^1$H-NMR δ($C_2D_2Cl_4$) 0.88 (t, 3H, J=6.9 Hz), 0.96-1.61 (m), 3.05-3.97 (m, 7H)

Melting point (Tm) 121° C.

Example 31

The reaction was carried out in the same manner as in Example 25, except that triethylenetetramine was used instead of diethanolamine in Example 25, to obtain a corresponding polymer (with respect to Formula (14), A: a group formed by ethylene polymerization (Mw=2015), R: hydrogen atom, one of X and Y being a hydroxyl group and the other being a 8-amino-3,6-diazaoctylamino group) at an epoxy conversion rate of 100%. The properties are as follows.

$^1$H-NMR δ($C_2D_2Cl_4$) 0.88 (t, 3H, J=6.9 Hz), 0.92-1.57 (m), 3.03-3.94 (m, 15H)

Melting point (Tm) 122° C.

Example 32

The reaction was carried out in the same manner as in Example 25, except that tetraethylenepentamine was used instead of diethanolamine in Example 25, to obtain a corresponding polymer (with respect to Formula (14), A: a group formed by ethylene polymerization (Mw=2015), R: hydrogen atom, one of X and Y being a hydroxyl group and the other being an 11-amino-3,6,9-triazaundecylamino group) at an epoxy conversion rate of 100%. The properties are as follows.

$^1$H-NMR δ($C_2D_2Cl_4$) 0.88 (t, 3H, J=6.6 Hz), 0.94-1.63 (m), 2.92-3.85 (m, 19H)

Melting point (Tm) 123° C.

Example 33

The reaction was carried out in the same manner as in Example 25, except that tris(2-aminoethyl)amine was used instead of diethanolamine in Example 25, to obtain a corresponding polymer (with respect to Formula (14), A: a group formed by ethylene polymerization (Mw=2015), R: hydrogen atom, one of X and Y being a hydroxyl group and the other being an N,N-bis(2-aminoethyl)-2-aminoethylamino group) at an epoxy conversion rate of 100%. The properties are as follows.

$^1$H-NMR δ($C_2D_2Cl_4$) 0.88 (t, 3H, J=6.9 Hz), 0.93-1.65 (m), 2.82-3.65 (m, 15H)

Melting point (Tm) 120° C.

Example 34

The reaction was carried out in the same manner as in Example 25, except that a polyoxypropylenediamine (polyoxypropylene having amines at both terminals, Jeffamine D400 (registered trademark)) having a molecular weight of about 400 was used instead of diethanolamine and the reaction temperature was changed to 150° C. in Example 25, to obtain a corresponding polymer (with respect to Formula (14), A: a group formed by ethylene polymerization (Mw=2015), R: hydrogen atom, one of X and Y being a hydroxyl group and the other being an ω-amino(polyoxypropylene)amino group) at an epoxy conversion rate of 100%. The properties are as follows.

$^1$H-NMR δ($C_2D_2Cl_4$) 0.88 (t, 3H, J=6.9 Hz), 0.96-1.83 (m), 3.24-3.92 (m)

Melting point (Tm) 121° C.

Example 35

828 mg of the polymer obtained in Example 17 (with respect to Formula (14), A: a group formed by ethylene polymerization (Mw=2015), R: hydrogen atom, one of X and Y being a hydroxyl group and the other being a 2-methoxyethoxy group), 695 mg of anhydrous succinic acid, 417 mg of pyridine and 5.0 g of toluene were introduced into a 50-mL flask, and stirred at 110° C. for 6 hours. Subsequently, 1 N hydrochloric acid was added to terminate the reaction, acetone was further added to crystallize the reaction product, and the resulting solid was collected by filtration. The obtained solid was washed with stirring twice with an aqueous acetone solution and three times with acetone, and then the resulting solid was collected by filtration. Subsequently, the solid was dried under reduced pressure at room temperature, to obtain 727 mg of a corresponding polymer (with respect to Formula (14), A: a group formed by ethylene polymerization (Mw 2015), R: hydrogen atom, one of X and Y being a 3-carboxypropionyloxy group and the other being a 2-methoxyethoxy group) as a solid, at a hydroxyl conversion rate of 100%. The properties are as follows.

$^1$H-NMR δ($C_2D_2Cl_4$) 0.88 (t, 3H, J=6.6 Hz), 0.96-1.62 (m), 2.61 (s, 4H), 3.34 (s, 3H), 3.46-3.58 (m, 6H), 4.92-5.04 (m, 1H)

Melting point (Tm) 121° C.

Example 36

204 mg of the polymer obtained in Example 17 (with respect to Formula (14), A: a group formed by ethylene polymerization (Mw=2015), R: hydrogen atom, one of X and Y being a hydroxyl group and the other being a 2-methoxyethoxy group) and 2.2 g of n-nonanoic acid were introduced into a 25-mL flask, and stirred at 150° C. for 8 hours. Water was added to terminate the reaction, acetone was further added to crystallize the reaction product, and the resulting solid was collected by filtration. The obtained solid was washed with stirring with a mixed solution of a saturated aqueous solution of sodium hydrogen carbonate and acetone, and further washed with stirring twice with an aqueous acetone solution and three times with acetone, and then the resulting solid was collected by filtration. The solid was dried under reduced pressure at room temperature, to obtain 186 mg of a corresponding polymer (with respect to Formula (14), A: a group formed by ethylene polymerization (Mw=2015), R: hydrogen atom, one of X and Y being a nonanoyloxy group and the other being a 2-methoxyethoxy group) as a solid, at a hydroxyl conversion rate of 100%. The properties are as follows.

$^1$H-NMR δ($C_2D_2Cl_4$) 0.88 (t, 3H, J=6.9 Hz), 0.95-1.73 (m), 2.26 (t, 2H, J=7.3 Hz), 3.32 (s, 3H), 3.43-3.62 (m, 6H), 4.90-5.03 (m, 1H)

IR (cm$^{-1}$) 2905, 1739, 1471, 1168, 719

Melting point (Tm) 117° C.

Example 37

The reaction was carried out in the same manner as in Example 36, except that perfluorooctanoic acid was used instead of n-nonanoic acid in Example 36, to obtain a corresponding polymer (with respect to Formula (14), A: a group formed by ethylene polymerization (Mw=2015), R: hydrogen atom, one of X and Y being a perfluorooctanoyloxy group and the other being a 2-methoxyethoxy group) as a solid at a hydroxyl conversion rate of 100%. The properties are as follows.

$^1$H-NMR δ($C_2D_2Cl_4$) 0.88 (t, 3H, J=6.9 Hz), 0.97-1.78 (m), 3.31 (s, 3H), 3.44-3.62 (m, 6H), 5.12-5.25 (m, 1H)

IR (cm$^{-1}$) 2961, 1780, 1460, 1217, 719

Melting point (Tm) 120° C.

Example 38

For the epoxy-terminated polymer of the starting materials, the epoxy-terminated polymer (E-2) synthesized in Synthesis Example 4 was used.

16 g (245 mmol) of KOH, 100 g (250 mmol) of polyethylene glycol (average molecular weight 400) and 70 g of toluene were introduced into a 500-mL separable flask, and stirred at 110° C. for 30 minutes. Subsequently, 38.7 g of the epoxy-terminated polymer (E-2) (45 mmol in terms of Mn 860) was added to this solution, and was stirred at 110° C. for 8 hours. Subsequently, a 1 mol/L aqueous hydrochloric acid solution was added to terminate the reaction, acetone was further added to crystallize the reaction product, and the resulting solid was collected by filtration. The obtained solid was washed with stirring with a mixed solution of a saturated aqueous solution of sodium hydrogen carbonate and acetone, and further washed one time with an aqueous acetone solution and twice with acetone, and then the resulting solid was collected by filtration. The solid was dried under reduced pressure at room temperature, to obtain 50 g of a corresponding polymer (with respect to Formula (14), A: a group formed by ethylene polymerization (Mw=1540), R: hydrogen atom, one of X and Y being a hydroxyl group and the other being a polyethylene glycol group (average molecular weight 400)) as a white solid, at an epoxy conversion rate of 100%. The properties are as follows.

$^1$H-NMR δ($C_2D_2Cl_4$) 0.88 (t, 3H, J=6.9 Hz), 0.95-1.78 (m), 3.30 (dd, 1H, J=7.6, 9.9 Hz), 3.47 (dd, 1H, J=3.3, 9.9 Hz), 3.50-3.78 (m)

Melting point (Tm) 118° C.

Example 39

The reaction was carried out in the same manner as in Example 38, except that 2-methoxyethanol was used instead of the polyethylene glycol having an average molecular weight of 400 in Example 38, to obtain a corresponding polymer (with respect to Formula (14), A: a group formed by ethylene polymerization (Mw=1540), R: hydrogen atom, one of X and Y being a hydroxyl group and the other being a 2-methoxyethoxy group) at an epoxy conversion rate of 100%. The properties are as follows.

$^1$H-NMR δ($C_2D_2Cl_4$) 0.88 (t, 3H, J=6.9 Hz), 0.95-1.78 (m), 3.30 (dd, 1H, J=7.6, 9.9 Hz), 3.34 (s, 3H), 3.47 (dd, 1H, J=3.3, 9.9 Hz), 3.47-3.55 (m, 2H), 3.57-3.64 (m, 2H), 3.66-3.78 (m, 1H)

Melting point (Tm) 119° C.

Example 40

The reaction was carried out in the same manner as in Example 38, except that polyethylene glycol having an average molecular weight of 600 was used instead of the polyethylene glycol having an average molecular weight of 400 in Example 38, to obtain a corresponding polymer (with respect to Formula (14), A: a group formed by ethylene polymerization (Mw=1540), R: hydrogen atom, one of X and Y being a hydroxyl group and the other being a polyethylene glycol group (average molecular weight 600)) at an epoxy conversion rate of 100%. The properties are as follows.

$^1$H-NMR δ($C_2D_2Cl_4$) 0.88 (t, 3H, J=6.9 Hz), 0.95-1.56 (m), 3.30 (dd, 1H, J=7.6, 9.9 Hz), 3.47 (dd, 1H, J=3.3, 9.9 Hz), 3.50-3.77 (m)

Melting point (Tm) 118° C.

Example 41

The reaction was carried out in the same manner as in Example 38, except that polyethylene glycol having an average molecular weight of 1000 was used instead of the polyethylene glycol having an average molecular weight of 400 in Example 38, to obtain a corresponding polymer (with respect to Formula (14), A: a group formed by ethylene polymerization (Mw=1540), R: hydrogen atom, one of X and Y being a hydroxyl group and the other being a polyethylene glycol group (average molecular weight 1000)) at an epoxy conversion rate of 100%. The properties are as follows.

$^1$H-NMR δ($C_2D_2Cl_4$) 0.88 (t, 3H, J=6.9 Hz), 1.05-1.57 (m), 3.17-3.72 (m), 3.79-3.92 (m, 1H)

Melting point (Tm) 119° C.

Example 42

The reaction was carried out in the same manner as in Example 38, except that dipropylene glycol was used instead of polyethylene glycol having an average molecular weight of 400 in Example 38, to obtain a corresponding polymer (with respect to Formula (14), A: a group formed by ethylene polymerization (Mw=1540), R: hydrogen atom, one of X and Y being a hydroxyl group and the other being a 2-methyl-5-hydroxy-3-oxahexyl group) at an epoxy conversion rate of 100%. The properties are as follows.

$^1$H-NMR δ($C_2D_2Cl_4$) 0.88 (t, 3H, J=6.6 Hz), 0.97-1.57 (m), 3.18-3.77 (m, 8H), 3.81-3.95 (m, 1H)

Melting point (Tm) 119° C.

Example 43

0.65 g of the epoxy-terminated polymer (E-2) used in Example 38 (0.75 mmol in terms of Mn 860), 0.50 g (4.8 mmol) of diethanolamine, and 1.5 g of toluene were introduced into a 50-mL flask, and were stirred at 120° C. for 8 hours. Subsequently, water was added to terminate the reaction, acetone was further added to crystallize the reaction product, and the resulting solid was collected by filtration. The obtained solid was washed, with stirring, one time with an aqueous acetone solution and three times with acetone, and the resulting solid was collected by filtration.

The solid was dried under reduced pressure at room temperature to obtain 0.67 g of a corresponding polymer (with respect to Formula (14), A: a group formed by ethylene polymerization (Mw=1540), R: hydrogen atom, one of X and Y being a hydroxyl group and the other being a bis(2-hydroxyethyl)amino group) as a white solid, at an epoxy conversion rate of 100%. The properties are as follows.

$^1$H-NMR δ($C_2D_2Cl_4$) 0.88 (t, 3H, J=7.3 Hz), 0.94-1.57 (m), 2.49 (dd, 1H, J=9.2, 13.5 Hz), 2.58-2.88 (m, 5H), 3.53-3.78 (m, 5H)

Melting point (Tm) 118° C.

Example 44

The reaction was carried out in the same manner as in Example 43, except that ethylenediamine was used instead of diethanolamine in Example 43, to obtain a corresponding polymer (with respect to Formula (14), A: a group formed by ethylene polymerization (Mw=1540), R: hydrogen atom, one of X and Y being a hydroxyl group and the other being a 2-aminoethylamino group) at an epoxy conversion rate of 100%. The properties are as follows.

$^1$H-NMR δ($C_2D_2Cl_4$) 0.88 (t, 3H, J=6.9 Hz), 0.95-1.60 (m), 3.28-4.27 (m, 7H)

Melting point (Tm) 120° C.

Example 45

The reaction was carried out in the same manner as in Example 43, except that triethylenetetramine was used instead of diethanolamine in Example 43, to obtain a corresponding polymer (with respect to Formula (14), A: a group formed by ethylene polymerization (Mw=1540), R: hydrogen atom, one of X and Y being a hydroxyl group and the other being an 8-amino-3,6-diazaoctylamino group) at an epoxy conversion rate of 100%. The properties are as follows.

$^1$H-NMR δ($C_2D_2Cl_4$) 0.88 (t, 3H, J=6.9 Hz), 0.96-1.73 (m), 2.85-4.20 (m, 15H)

Melting point (Tm) 120° C.

Example 46

The reaction was carried out in the same manner as in Example 43, except that pentaethylenehexamine was used instead of diethanolamine in Example 43, to obtain a corresponding polymer (with respect to Formula (14), A: a group formed by ethylene polymerization (Mw=1540), R: hydrogen atom, one of X and Y being a hydroxyl group and the other being a 14-amino-3,6,9,12-tetraazatetradecylamino group) at an epoxy conversion rate of 100%. The properties are as follows.

$^1$H-NMR δ($C_2D_2Cl_4$) 0.88 (t, 3H, J=6.9 Hz), 0.94-1.57 (m), 2.60-3.87 (m, 23H)

Melting point (Tm) 119° C.

Example 47

The reaction was carried out in the same manner as in Example 19, except that the epoxy-terminated polymer (E-3) was used instead of the epoxy-terminated polymer (E-1) in Example 19, to obtain a corresponding polymer (with respect to Formula (14), A: a group formed by copolymerization of ethylene and propylene (Mw=1687), R: hydrogen atom, one of X and Y being a hydroxyl group and the other being a polyethylene glycol group (average molecular weight 600)) at an epoxy conversion rate of 100%. The properties are as follows.

$^1$H-NMR δ($C_2D_2Cl_4$) 0.77-0.92 (m), 0.95-1.60 (m), 3.30 (dd, 1H, J=7.6, 9.9 Hz), 3.47 (dd, 1H, J=3.3, 9.9 Hz), 3.51-3.88 (m)

Melting point (Tm) 109° C.

Example 48

The reaction was carried out in the same manner as in Example 25, except that the epoxy-terminated polymer (E-3) was used instead of the epoxy-terminated polymer (E-1) in Example 25, to obtain a corresponding polymer (with respect to Formula (14), A: a group formed by copolymerization of ethylene and propylene (Mw=1687), R: hydrogen atom, one of X and Y being a hydroxyl group and the other being a bis(2-hydroxyethyl)amino group) at an epoxy conversion rate of 100%. The properties are as follows.

$^1$H-NMR δ($C_2D_2Cl_4$) 0.82-0.93 (m), 0.95-1.70 (m), 2.46 (dd, 1H, J=9.6, 13.2 Hz), 2.61 (dd, 1H, J=3.0, 13.2 Hz), 2.65-2.86 (m, 4H), 3.54-3.72 (m, 5H)

Melting point (Tm) 109° C.

Example 49

The reaction was carried out in the same manner as in Example 19, except that the epoxy-terminated polymer (E-4) was used instead of the epoxy-terminated polymer (E-1) in Example 19, to obtain a corresponding polymer (with respect to Formula (14), A: a group formed by copolymerization of ethylene and propylene (Mw=1267), R: hydrogen atom, one of X and Y being a hydroxyl group and the other being a polyethylene glycol group (average molecular weight 600)) at an epoxy conversion rate of 100%. The properties are as follows.

$^1$H-NMR δ($C_2D_2Cl_4$) 0.82-0.93 (m), 0.95-1.65 (m), 3.30 (dd, 1H, J=7.3, 9.9 Hz), 3.47 (dd, 1H, J=3.3, 9.9 Hz), 3.50-3.78 (m)

Melting point (Tm) 52° C.

Example 50

The reaction was carried out in the same manner as in Example 25, except that the epoxy-terminated polymer (E-4) was used instead of the epoxy-terminated polymer (E-1) in Example 25, to obtain a corresponding polymer (with respect to Formula (14), A: a group formed by copolymerization of ethylene and propylene (Mw=1267), R: hydrogen atom, one of X and Y being a hydroxyl group and the other being a bis(2-hydroxyethyl)amino group) at an epoxy conversion rate of 100%. The properties are as follows.

$^1$H-NMR δ($C_2D_2Cl_4$) 0.80-0.90 (m), 0.90-1.56 (m), 2.46 (dd, 1H, J=9.2, 13.5 Hz), 2.61 (dd, 1H, J=3.3, 13.5 Hz), 2.61-2.84 (m, 4H), 3.58-3.68 (m, 5H)

Melting point (Tm) 81° C.

Example 51

10 g of the α,β-dihydroxy polymer (D-1) obtained in Example 1 and 80 g of toluene were introduced into a 500-mL flask equipped with a nitrogen inlet tube, a thermometer, a cooling tube and a stirring device, and while heating in an oil bath at 125° C. with stirring, the solids were completely dissolved. After cooling to 90° C., 148 mg of 85% KOH that had been dissolved in 5.0 g of water in advance was added to the flask, and the contents were mixed under reflux for 2 hours. Subsequently, the temperature in the flask was slowly increased to 120° C., and water and toluene were distilled off. Furthermore, water and toluene in the flask were completely distilled off by reducing the pressure in the flask while supplying minimal nitrogen into the flask. After cooling to room temperature, the solids solidified in the flask were broken and taken out.

The entire amount of the obtained solids and 200 g of dehydrated toluene were introduced into a 1.5-L stainless steel pressurized reactor equipped with a heating device, a stirring device, a thermometer, a manometer and a safety valve, and after purging the gas phase with nitrogen, the contents were heated to 100° C. with stirring. After 30 minutes, 11.8 g of ethylene oxide was added, and the temperature was slowly elevated to 130° C. over 3 hours. After further maintaining at 130° C. for 7 hours, the contents were cooled to room temperature to obtain a slurry liquid. Toluene in the slurry liquid was distilled off to obtain 19.5 g of Copolymer (7) having polyethylene glycol groups for both X and Y with respect to Formula (14) (A: a group formed by ethylene polymerization (Mw=2015), R: hydrogen atom). Based on the $^1$H-NMR measurements of the obtained polymer, it was found from a comparison of the integral value for the terminal methyl group of the polyethylene group (A) (shift value: 0.88 ppm) and the integral value for the alkylene group of the PEG moiety (shift value: 3.34-3.72 ppm) with respect to Formula (14), that 26 ethylene glycol units on the average are bonded to X and Y in combination.

$^1$H-NMR δ($C_2D_2Cl_4$) 0.88 (3H, t, J=6.75 Hz), 1.04-1.66 (m), 3.34-3.72 (m)

Melting point (Tm) 120° C.

Example 52

20.0 g of the polymer obtained in Example 25 (with respect to Formula (14), A: a group formed by ethylene polymerization (Mw=2015), R: hydrogen atom, one of X and Y being a hydroxyl group and the other being a bis(2-hydroxyethyl)amino group) and 100 g of toluene were introduced into a 500-mL flask equipped with a nitrogen inlet tube, a thermometer, a cooling tube and a stirring device, and while heating in an oil bath at 125° C. with stirring, the solids were completely dissolved. After cooling to 90° C., 411 mg of 85% KOH that had been dissolved in 5.0 g of water in advance was added to the flask, and the contents were mixed under reflux for 2 hours. Subsequently, the temperature in the flask was slowly increased to 120° C., and water and toluene were distilled off. Furthermore, water and toluene in the flask were further distilled off by reducing the pressure in the flask while supplying minimal nitrogen into the flask, elevating the internal temperature further to 150° C. and then maintaining at that temperature for 4 hours. After cooling to room temperature, the solids solidified in the flask were broken and taken out.

18.0 g of the obtained solids and 200 g of dehydrated toluene were introduced into a 1.5-L stainless steel pressurized reactor equipped with a heating device, a stirring device, a thermometer, a manometer and a safety valve, and after purging the gas phase with nitrogen, the temperature was elevated to 130° C. with stirring. After 30 minutes, 18.0 g of ethylene oxide was added, and the temperature was maintained at 130° C. for another 5 hours and then cooled to room temperature to obtain a slurry liquid. The slurry liquid was separated by filtration to obtain a toluene solution and solids.

Toluene in the toluene solution was distilled off and dried to obtain 7.7 g of a polymer having a polyethylene glycol group for either X or Y and an amino group represented by the moiety Formula (16) (with respect to Formula (16), polyethylene glycol groups for both $R^8$ and $R^9$) for the other between X and Y, with respect to Formula (14) (A: a group formed by ethylene polymerization (Mw=2015), R: hydrogen atom). Based on $^1$H-NMR measurement of the obtained polymer, it was found from a comparison of the integral value for the terminal methyl group of the polyolefin group A (shift value: 0.88 ppm) and the integral value for the alkylene group of the PEG moiety (shift value: 3.33-3.72 ppm), that 31 ethylene glycol units on the average were bonded to X or Y and R8 and R9 in combination. 0.2 g of the polymer was mixed with 3.8 g of water and stirred for 10 minutes while boiling, then further stirred ultrasonically for 10 minutes, and cooled to room temperature to obtain transparent micelles. The average particle size was measured using a Microtrack JPA manufactured by Honeywell, Inc., and the average micelle particle size was 15 nm.

$^1$H-NMR δ($C_2D_2Cl_4$) 0.88 (3H, t, J=6.8 Hz), 1.06-1.50 (m), 2.80-3.20 (m), 3.33-3.72 (m)

Melting point (Tm) 73° C.

Toluene was dried from the solids that were not soluble in toluene, to obtain 24.4 g of a polymer having the same structure as that of the polymer obtained from the toluene solution (Copolymer (8) having a polyethylene glycol group for either X or Y and an amino group having polyethylene glycol groups for both $R^8$ and $R^9$ with respect to the moiety Formula (16), for the other between X and Y, with respect to Formula (14) (A: a group formed by ethylene polymerization, R: hydrogen atom or a methyl group)). Based on $^1$H-NMR measurement of the obtained polymer, it was found from a comparison of the integral value for the terminal methyl group of the polyolefin group A (shift value: 0.88 ppm) and the integral value for the alkylene group of the PEG moiety (shift value: 3.32-3.69 ppm), that 25 ethylene glycol units on the average are bonded to X or Y and $R^8$ and $R^9$ in combination.

$^1$H-NMR δ($C_2D_2Cl_4$) 0.88 (3H, t, J=6.8 Hz), 1.04-1.50 (m), 2.80-3.20 (m), 3.32-3.69 (m)

Melting point (Tm) 116° C.

Example 53

19.1 g of the polymer obtained in Example 48 (with respect to Formula (14), A: a group formed by copolymerization of ethylene and propylene (Mw=1687), R: hydrogen atom or a methyl group, one of X and Y being a hydroxyl group and the other being a bis(2-hydroxyethyl)amino group) and 150 g of toluene were introduced into a 500-mL flask equipped with a nitrogen inlet tube, a thermometer, a cooling tube and a stirring device, and while heating in an oil bath at 125° C. with stirring, the solids were completely dissolved. After cooling to 90° C., 330 mg of 85% KOH that had been dissolved in 5.0 g of water in advance was added to the flask, and the contents were mixed under reflux for 2 hours. Subsequently, the temperature in the flask was slowly increased to 120° C., and water and toluene were distilled off. Furthermore, water and toluene in the flask were further distilled off by reducing the pressure in the flask while supplying minimal nitrogen into the flask, elevating the internal temperature further to 150° C. and then maintaining at that temperature for 4 hours. After cooling to room temperature, the solids solidified in the flask were broken and taken out.

18.4 g of the obtained solids and 200 g of dehydrated toluene were introduced into a 1.5-L stainless steel pressurized reactor equipped with a heating device, a stirring device, a thermometer, a manometer and a safety valve, and after purging the gas phase with nitrogen, the temperature was elevated to 130° C. with stirring. After 30 minutes, 18.4 g of ethylene oxide was added, and the temperature was maintained at 130° C. for another 3 hours and then cooled to room temperature to obtain a slurry liquid. The slurry liquid was separated by filtration to obtain a toluene solution and solids.

Toluene in the toluene solution was distilled off and dried to obtain 12.4 g of a polymer having a polyethylene glycol group for either X or Y and an amino group represented by the moiety Formula (16) (with respect to Formula (16), polyethylene glycol groups for both $R^8$ and $R^9$) for the other between X and Y, with respect to Formula (14) (A: a group formed by copolymerization of ethylene and propylene, R: hydrogen atom or a methyl group). Based on $^1$H-NMR measurement of the obtained polymer, it was found from a comparison of the integral value for the methyl group and methylene group of the polyolefin groups A and R (shift values: 0.84-0.91 ppm (methyl group), 1.08-1.51 ppm (methylene group)) and the integral value for the alkylene group of the PEG moiety (shift value: 3.33-3.72 ppm), that the weight ratio of the polyolefin block and the polyethylene glycol block was 34:66. 0.2 g of the polymer was mixed with 0.8 g of water and stirred for 10 minutes at 80° C., then further stirred ultrasonically for 10 minutes, and cooled to room temperature to obtain transparent micelles. The average particle size was measured using a Microtrack JPA manufactured by Honeywell, Inc., and the average micelle particle size was 20 nm.

$^1$H-NMR δ($C_2D_2Cl_4$) 0.84-0.91 (m), 1.08-1.51 (m), 2.80-3.20 (m), 3.33-3.72 (m)

Melting point (Tm) 67° C.

Toluene was dried from the solids that were not soluble in toluene, to obtain 19.6 g of a polymer having the same structure as that of the polymer obtained from the toluene solution (a polymer having a polyethylene glycol group for either X or Y and an amino group having polyethylene glycol groups for both $R^8$ and $R^9$ with respect to the moiety Formula (16) for the other of X and Y, with respect to Formula (14) (A: a group formed by copolymerization of ethylene and propylene, R: hydrogen atom or a methyl group)). Based on $^1$H-NMR measurement of the obtained polymer, it was found from a comparison of the integral value for the methyl group and methylene group of the polyolefin groups A and R (shift values: 0.85-0.92 ppm (methyl group), 1.09-1.51 ppm (methylene group)) and the integral value for the alkylene group of the PEG moiety (shift value: 3.33-3.73 ppm), that the weight ratio of the polyolefin block and the polyethylene glycol block was 62:38.

$^1$H-NMR δ($C_2D_2Cl_4$) 0.85-0.92 (m), 1.09-1.51 (m), 2.70-3.00 (m), 3.33-3.73 (m)

Melting point (Tm) 106° C.

Example 54

2.0 g of the Copolymer (7) synthesized in Example 51, 10 g of toluene and 0.2 g of phthalic acid dichloride were added to a 30-mL flask equipped with a nitrogen inlet tube, a thermometer, a cooling tube and a stirring device. Under the conditions of slight pressurization with nitrogen, the mixture was refluxed for 4 hours. Subsequently, the mixture was stirred at 150° C. for 4 hours while distilling off toluene, then further stirred under reduced pressure for 2 hours while removing the solvent and the generated gases, to obtain 2.1 g of a polymer that the terminal hydroxyl groups of the polyethylene glycol groups of the polymer having polyethylene glycol groups for both X and Y with respect to Formula (14) were further polyesterified with dicarboxylic acid in the reactor.

$^1$H-NMR δ($C_2D_2Cl_4$) 0.88 (t, J=6.8 Hz), 1.13-1.50 (m), 3.31-3.79 (m), 4.42 (t, J=5.3 Hz), 7.48-7.52 (m), 7.69-7.73 (m)

Melting point (Tm) 119° C.

Example 55

Evaluation 1 of Antistatic Property in LLDPE Resin 5 g of the Copolymer (1) obtained in Example 3 (amount of addition 10% by weight), and 0.10 g of sodium perchlorate monohydrate as an alkali salt were added to 45 g of LLDPE (Mitsui Chemicals, Inc., EVOLUE SP2320), and kneaded at 180° C. for 10 minutes in a 4C150-01 type Laboplastmill manufactured by Toyo Seiki Seisaku-sho, Ltd.), and the kneaded product was taken out.

Subsequently, the kneaded product was molded by hot pressing. Molding was carried out such that the product was compressed for 3 minutes while heating to 170° C. with a vacuum hot press and then taken out for quenching to room temperature. Thus, a hot pressed sheet for evaluation having a size of 130 mmφ×0.5 mm was obtained.

The obtained hot pressed sheet was left in a thermostat-hygrostat chamber controlled to a temperature of 23±2° C. and a humidity of 50±5% RH for 24 hours, and the surface resistance value was measured at an applied voltage of 500 V, which was found to be $6.42×10^{12}$Ω. The contact angle of water was 70°.

Comparative Example 1

As a comparison, the cases for LLDPE only, LLDPE with sodium perchlorate (0.2% by weight with respect to the polymer), LLDPE with sodium perchlorate (0.2% by weight with respect to the polymer and PEG600 used in Example 3 (10% by weight with respect to the polymers in total) were also evaluated. As a result, the surface resistance was in the order of $10^{16}$Ω in all cases, and kneading with PEG600 resulted in inhomogeneous molded products only.

Example 56

Evaluation 2 of Antistatic Property in LLDPE Resin

A hot pressed sheet for evaluation was produced in the same manner as in Example 55, except that the Copolymer (2) obtained in Example 4 was used instead of the Copolymer (1), and 0.15 g of sodium perchlorate monohydrate was used, and was subjected to evaluation. The surface resistance value was $2.91 \times 10^{11} \Omega$. The contact angle of water was 52°.

Example 57

Evaluation 3 of Antistatic Property in LLDPE Resin

A hot pressed sheet for evaluation was produced in the same manner as in Example 55, except that the Copolymer (4) obtained in Example 6 was used instead of the Copolymer (1), and 0.15 g of potassium acetate was used instead of sodium perchlorate monohydrate, and was subjected to evaluation. The surface resistance value was $1.37 \times 10^{11} \Omega$. The contact angle of water was 53°.

Example 58

Evaluation 4 of Antistatic Property in LLDPE Resin 45 g of LLDPE (Mitsui Chemicals, Inc., EVOLUE SP2320) and 5 g of the Copolymer (4) obtained in Example 6 (amount of addition 10% by weight) were kneaded at 180° C. for 10 minutes in a 4C150-01 type Laboplastmill manufactured by Toyo Seiki Seisaku-sho, Ltd., and then 0.10 g of sodium perchlorate monohydrate as an alkali salt was added and kneaded for 1 minute. The kneaded product was taken out.

The hot press molding and measurement of surface resistance value were carried out in the same manner as in Example 55, and as a result, the surface resistance value was $8.01 \times 10^{10} \Omega$. The contact angle of water was 56°.

Example 59

Evaluation of Antistatic Property in LLDPE Resin

A hot pressed sheet for evaluation was produced in the same manner as in Example 55, except that the Copolymer (5) obtained in Example 7 was used instead of the Copolymer (1), and 0.15 g of potassium acetate was used instead of sodium perchlorate monohydrate, and was subjected to evaluation. The surface resistance value was $1.91 \times 10^{12} \Omega$. The contact angle of water was 79°.

Example 60

Evaluation 6 of Antistatic Property in LLDPE Resin

A hot pressed sheet for evaluation was produced in the same manner as in Example 55, except that the Copolymer (7) obtained in Example 51 was used instead of the Copolymer (1), and 0.15 g of potassium acetate was used instead of sodium perchlorate monohydrate, and was subjected to evaluation. The surface resistance value was $1.47 \times 10^{11} \Omega$. The contact angle of water was 310.

Example 61

Evaluation 7 of Antistatic Property in LLDPE Resin

A hot pressed sheet for evaluation was produced in the same manner as in Example 55, except that the Copolymer (8) obtained in Example 52 was used instead of the Copolymer (1), and 0.15 g of potassium acetate was used instead of sodium perchlorate monohydrate, and was subjected to evaluation. The surface resistance value was $1.11 \times 10^{9} \Omega$. The contact angle of water was 18°.

Example 62

Evaluation 8 of Antistatic Property in LLDPE Resin

A hot pressed sheet for evaluation was produced in the same manner as in Example 55, except that the Copolymer (6) obtained in Example 8 was used instead of the Copolymer (1), and 0.15 g of sodium perchlorate monohydrate was used, and was subjected to evaluation. The surface resistance value was $2.56 \times 10^{13} \Omega$. The contact angle of water was 640.

Example 63

Evaluation of Antistatic Property in Polypropylene Resin)

2.5 g of the Copolymer (3) obtained in Example 5 (amount of addition 10% by weight), 1000 ppm of IRGANOX 1010 (Nagase & Co., Ltd.), 1000 ppm of IRGAFOS 168 as stabilizers, and 500 ppm of calcium stearate were added to 22.5 g of polypropylene (Mitsui Chemicals, Inc., HomoPP grade F107BV), and the mixture was kneaded at 200° C. for 5 minutes in a 4C150-01 type Laboplastmill manufactured by Toyo Seiki Seisaku-sho, Ltd. The kneaded product was taken out.

Subsequently, the kneaded product was molded by hot pressing. Molding was carried out such that the product was compressed at 9.8 MPa (100 kgf/cm²) for 5 minutes while heating to 200° C., and then quenched to room temperature while compressing at 2.45 MPa (25 kgf/cm²) for 5 minutes. Thus, a hot pressed sheet for evaluation having a size of 95 mm×95 mm×3 mm was obtained.

The obtained hot pressed sheet was left in a thermostat-hygrostat chamber controlled to a temperature of 23±2° C. and a humidity of 50±5% RH for 24 hours, and the surface resistance value was measured at an applied voltage of 500 V, which was found to be $8.76 \times 10^{12} \Omega$. The contact angle of water was also measured, which was found to be 63.50.

Comparative Example 2

A hot pressed sheet for evaluation was produced in the same manner as in Example 55, except that commercial polyether ester amide copolymer (Chiba Specialty Chemicals Co., Ltd., IRGASTAT P18) was used instead of the Copolymer (1), and sodium perchlorate monohydrate was not used, and was subjected to evaluation. The surface resistance value was $3.67 \times 10^{14} \Omega$. The contact angle of water was 95°.

Example 64

The polymer obtained in Example 40 was melted at 150° C. and was neutralized with 40 parts of a 36% aqueous hydrochloric acid solution with stirring. The neutralized molten product was slowly added dropwise to 500 parts of distilled water at 90° C. with stirring at 5000 rpm in a T.K. Homomixer-MARKII (IPROS Corp.), to obtain a white transparent emulsion composition. The obtained emulsion composition was subjected to measurement of the following terms.

1. Dispersed State of Dispersion

The dispersed state was investigated by passing the dispersion through a metallic mesh of 100 meshes. The evaluation results are presented in Table 1.

2. Size (μm) of Particles in Emulsion Composition

The average particle size of 50% by volume was measured with a Microtrack UPA (Honeywell, Inc.), and the evaluation results are presented in Table 1.

3. Rub Resistance A (Ink Composition)

A cationic acrylic emulsion was prepared by the following method.

200.0 parts of distilled water and 0.1 parts of stearyltrimethylammonium chloride were introduced into a reactor, and under a nitrogen stream, the temperature was elevated to 70° C. 0.6 parts of 2,2'-azobis(2-amidinopropane) dihydrochloride was added. Apart from this, an emulsion mixture in which 64.0 parts of methyl methacrylate, 20.0 parts of n-butyl acrylate, and 16.0 parts of a methyl chloride quaternary salt of N,N-dimethylaminopropylacrylamide were emulsified in 40 parts of distilled water using 0.3 parts of stearyltrimethylammonium chloride was prepared. This emulsion mixture was added dropwise into the reactor over 4 hours, and then further maintained at the same temperature for 4 hours. Subsequently, 0.1 parts of 2,2'-azobis(2-amidinopropane) dihydrochloride was added, and further maintained at the same temperature for 3 hours to complete polymerization. As a result, a cationic acrylic emulsion was obtained.

An ink composition was prepared by mixing 10 parts of each of the emulsion compositions described in the following Examples 64 to 67, 100 parts of the cationic acrylic emulsion obtained by the above-described method, and 30 parts of a titanium white pigment dispersion. This composition was coated on a liner paper with a size of 30×150 mm to a thickness of 5 μm and dried at 120° C. for 1 minute. The peel-off state of the ink was observed using a Japan Society for the Promotion of Science type crock meter by setting the load to 20 gf and rubbing the same point 100 times. The evaluation results are presented in Table 1.

4. Rub Resistance B (Coating Agent Composition)

A lubricant coating agent was prepared by mixing 5 parts of each of the emulsion compositions described in the following Examples 64 to 67 and 100 parts of the cationic acrylic emulsion obtained by the above-described method. The present composition was coated on a metal plate (Zinccoat Testpiece Co., Ltd.) having a size of 70×150 mm to a thickness of 3 μm, and dried at 120° C. for 1 minute. The rub resistance coefficient was measured using a stainless steel sphere having a diameter of 10 mm by setting the load to 500 gf and rubbing the same point 50 times.

The results of these evaluations are presented in Table 1.

Example 65

The polymer obtained in Example 41 was melted at 150° C. and was neutralized with 40 parts of a 36% aqueous hydrochloric acid solution with stirring. The neutralized molten product was slowly added dropwise to 500 parts of distilled water at 90° C. with stirring at 5000 rpm in a T.K. Homomixer-MARKII (IPROS Corp.), to obtain a white transparent emulsion composition. The obtained emulsion composition was subjected to measurement of the evaluation terms of Example 64. The evaluation results are presented in Table 1.

Example 66

The polymer obtained in Example 45 was melted at 150° C. and was neutralized with 40 parts of a 36% aqueous hydrochloric acid solution with stirring. The neutralized molten product was slowly added dropwise to 500 parts of distilled water at 90° C. with stirring at 5000 rpm in a T.K. Homomixer-MARKII (IPROS Corp.), to obtain a brownish red emulsion composition. The obtained emulsion composition was subjected to measurement of the evaluation terms of Example 64. The evaluation results are presented in Table 1.

Example 67

The polymer obtained in Example 46 was melted at 150° C. and was neutralized with 40 parts of a 36% aqueous hydrochloric acid solution with stirring. The neutralized molten product was slowly added dropwise to 500 parts of distilled water at 90° C. with stirring at 5000 rpm in a T.K. Homomixer-MARKII (IPROS Corp.), to obtain a brownish red emulsion composition. The obtained emulsion composition was subjected to measurement of the evaluation terms of Example 64. The evaluation results are presented in Table 1.

TABLE 1

|  | Example 64 | Example 65 | Example 66 | Example 67 |
|---|---|---|---|---|
| Molecular weight of A (Mw) | 1540 | 1540 | 1540 | 1540 |
| Polyalkylene glycol group | PEG600 | PEG1000 | | |
| Nitrogen-containing substituent | | | Triethylene tetramine | Pentaethylene hexamine |
| Dispersed state | ○ | ○ | ○ | ○ |
| Particle size (μm) | 10.5 | 5.2 | 8.2 | 6.4 |
| Rub resistance A | ○ | ○ | ○ | ○ |
| Rub resistance B | ○ | ○ | ○ | ○ |

Dispersed state:
○ homogeneously dispersed
x not dispersed even with stirring
Rub resistance A:
○ less than 2% of ink peel-off
x 2% or more of ink peel-off
Rub resistance B:
○ friction coefficient less than 0.1
x friction coefficient 0.1 or more

INDUSTRIAL APPLICABILITY

The novel polymer which can be provided by the present invention and the composition comprising the polymer are useful particularly as antistatic agents. The resin composition comprising the polymer is useful for molded articles required to have antistatic property, or for molded articles required to have good coatability and printability.

The polyolefin-containing polysiloxane provided by the invention has, for example, improved compatibility with cosmetic cakes and oil components compared with conventional materials, and thus the polyolefin-containing polysiloxane has excellent sense of use as a cosmetic material and is useful particularly as an additive for makeup cosmetic materials.

According to the invention, there is provided a polymer which is a wax material having higher heat resistance than conventional materials and is useful as a paint modifier, a glazing agent or a natural wax blending agent, and which is a resin molding processing improving agent and is useful as a releasing agent for resin molding, a rubber processing aid, or a fiber processing aid.

According to the invention, there is provided a polymer which is also useful as a paper quality improving agent, an abrasion resistance improving agent for ink, a hot melt additive, an electric insulator, an antifogging agent for polyolefin film, a thickening agent for oily compounds (gelling agent), a material for lipid vesicles, a hydrophilizing agent for polyolefin, a water repellant, a molding aid for agrochemical preparations, an antistatic agent, a releasing agent for toner, a pigment dispersant, a lubricant for vinyl chloride resins, or an emulsion composition.

The invention claimed is:
1. A polymer having at least a structural unit represented by the following Formula (1):

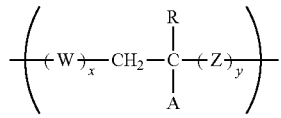
(1)

wherein A is a polymer of ethylene or propylene, the polymer having a weight average molecular weight of 400 to 500,000; R is a hydrogen atom, or an alkyl group or aralkyl group having 1 to 18 carbon atoms; W and Z are each independently an oxygen atom, an NH group or a sulfur atom; and x and y are each 0 or 1, with the proviso that at least one of them is 1,
wherein the polymer having at least a structural unit represented by the formula (1) contains a structural unit represented by Formula (2):

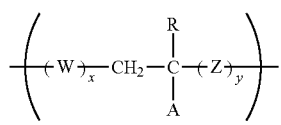
(1)

wherein A and R are as defined in Formula (1); and n is an integer of 1 or greater, and
at least one structural unit selected from the group consisting of structural units represented by Formula (5) and Formula (6):

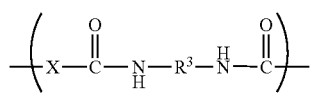
(5)

wherein X is an oxygen atom or an NH group; and $R^3$ is a divalent hydrocarbon group having 1 to 20 carbon atoms which may contain heteroatoms; and

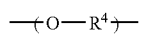
(6)

wherein $R^4$ is a divalent hydrocarbon group having 1 to 20 carbon atoms which may contain heteroatoms.
2. The polymer according to claim 1, wherein said polymer has hydroxyl groups at both terminals.
3. A polymer having at least a structural unit represented by the following Formula (1):

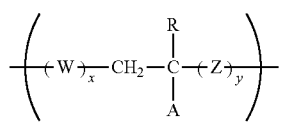
(1)

wherein A is a polymer of ethylene or propylene, the polymer having a weight average molecular weight of 400 to 500,000; R is a hydrogen atom, or an alkyl group or aralkyl group having 1 to 18 carbon atoms; W and Z are each independently an oxygen atom, an NH group or a sulfur atom; and x and y are each 0 or 1, with the proviso that at least one of them is 1,
wherein the polymer having at least a structural unit represented by the Formula (1) is a polysiloxane compound (II) containing the structural unit represented by the following Formula (2):

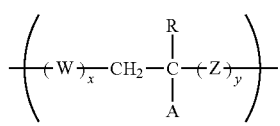
(1)

wherein A and R are as defined in the above-described Formula (1); and n is an integer of 1 or greater.
4. The polymer according to claim 3, wherein the polysiloxane compound is a compound represented by the following Formula (9):

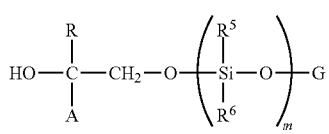
(9)

wherein A and R are as defined in the above-described Formula (1); $R^5$ and $R^6$, which may be identical or different, are each a hydrogen atom, or an alkyl group having 1 to 10 carbon atoms or an aryl group; m is a number from 1 to 3,000; and G is a hydrogen atom, an alkyl group having 1 to 5 carbon atoms, an alkali metal or a group represented by the following Formula (10):

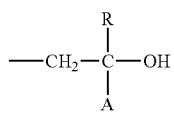
(10)

wherein A and R are as defined in the above Formula (1).
5. A polymer having at least a structural unit represented by the following Formula (1):

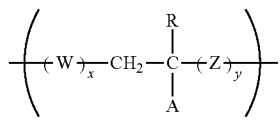
(1)

wherein A is a polymer of ethylene or propylene, the polymer having a weight average molecular weight of 400 to 500,000; R is a hydrogen atom, or an alkyl group or aralkyl group having 1 to 18 carbon atoms; W and Z are each independently an oxygen atom, an NH group or a sulfur atom; and x and y are each 0 or 1, with the proviso that at least one of them is 1,
wherein the polymer having at least a structural unit represented by the Formula (1) is a polymer (III) represented by the following Formula (14):

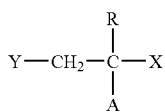

wherein A and R are as defined in the above Formula (1); X and Y are such that one of them is a hydroxyl group or a polyalkylene glycol group, and the other is a group represented by any of the following Formula (15) or Formula (16); and X and Y may be bonded to each other to form a 5-membered ring:

$$-E-R^7 \quad (15)$$

wherein E is an oxygen atom or a sulfur atom; and $R^7$ is a hydrogen atom, a hydrocarbon group, an acyl group or a polyalkylene glycol group;

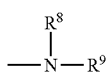

wherein $R^8$ and $R^9$, which may be identical or different, are each a hydrogen atom, a hydrocarbon group, an acyl group or a polyalkylene glycol group.

6. A composition comprising the polymer according to claim 1.

7. A resin composition comprising the polymer according to claim 1 and at least one material selected from the group consisting of salts of alkali metals or alkaline earth metals, surfactants, compatibilizing agents and polymer antistatic agents other than a polymer having a structural unit represented by the following Formula (2):

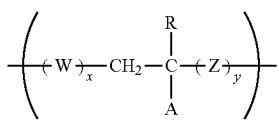

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; and n is an integer of 1 or greater.

8. A resin composition comprising the polymer according to claim 1 and other thermoplastic resin.

9. A resin composition containing the polymer according to claim 1 and other thermoplastic resin, and further at least one material selected from the group consisting of salts of alkali metals or alkaline earth metals, surfactants, compatibilizing agents and polymer antistatic agents other than a polymer having a structural unit represented by the following Formula (2):

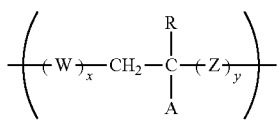

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; and n is an integer of 1 or greater.

10. An antistatic agent containing the polymer according to claim 1.

11. An adhesive containing the polymer according to claim 1.

12. A coating composition containing the polymer according to claim 1.

13. A molded product formed by molding the composition containing the polymer according to claim 1.

14. A molded product obtained by coating or printing on a molded product formed by molding a composition containing the polymer according to claim 1.

15. A cosmetic material containing the polymer according to claim 1.

16. A releasing agent for toner containing the polymer according to claim 1.

17. A pigment dispersant containing the polymer according to claim 1.

18. A lubricant for vinyl chloride resins, containing the polymer according to claim 1.

19. An emulsion composition containing the polymer according to claim 1.

20. An oxygen trapping composition containing the polymer according to claim 1.

21. A composition comprising the polymer according to claim 4.

22. A composition comprising the polymer according to claim 5.

23. A composition comprising the polymer according to claim 2.

24. The polymer according to claim 1, wherein A is a homopolymer of ethylene or a copolymer of ethylene and propylene.

25. The polymer according to claim 3, wherein A is a homopolymer of ethylene or a copolymer of ethylene and propylene.

26. The polymer according to claim 5, wherein A is a homopolymer of ethylene or a copolymer of ethylene and propylene.

27. A resin composition comprising the polymer according to claim 3 and at least one material selected from the group consisting of salts of alkali metals or alkaline earth metals, surfactants, compatibilizing agents and polymer antistatic agents other than a polymer having a structural unit represented by the following Formula (2):

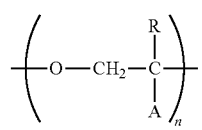

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; and n is an integer of 1 or greater.

28. A resin composition comprising the polymer according to claim 3 and other thermoplastic resin.

29. A resin composition containing the polymer according to claim 3 and other thermoplastic resin, and further at least one material selected from the group consisting of salts of alkali metals or alkaline earth metals, surfactants, compatibilizing agents and polymer antistatic agents other than a polymer having a structural unit represented by the following Formula (2):

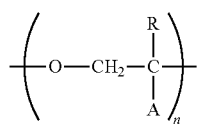

(2)

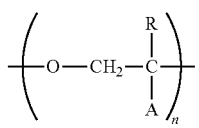

(2)

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; and n is an integer of 1 or greater.

30. An antistatic agent containing the polymer according to claim 3.

31. An adhesive containing the polymer according to claim 3.

32. A coating composition containing the polymer according to claim 3.

33. A molded product formed by molding the composition containing the polymer according to claim 3.

34. A molded product obtained by coating or printing on a molded product formed by molding a composition containing the polymer according to claim 3.

35. A cosmetic material containing the polymer according to claim 3.

36. A releasing agent for toner containing the polymer according to claim 3.

37. A pigment dispersant containing the polymer according to claim 3.

38. A lubricant for vinyl chloride resins, containing the polymer according to claim 3.

39. An emulsion composition containing the polymer according to claim 3.

40. An oxygen trapping composition containing the polymer according to claim 3.

41. A resin composition comprising the polymer according to claim 4 and at least one material selected from the group consisting of salts of alkali metals or alkaline earth metals, surfactants, compatibilizing agents and polymer antistatic agents other than a polymer having a structural unit represented by the following Formula (2):

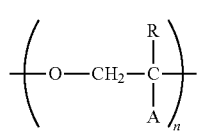

(2)

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; and n is an integer of 1 or greater.

42. A resin composition comprising the polymer according to claim 4 and other thermoplastic resin.

43. A resin composition containing the polymer according to claim 4 and other thermoplastic resin, and further at least one material selected from the group consisting of salts of alkali metals or alkaline earth metals, surfactants, compatibilizing agents and polymer antistatic agents other than a polymer having a structural unit represented by the following Formula (2):

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; and n is an integer of 1 or greater.

44. An antistatic agent containing the polymer according to claim 4.

45. An adhesive containing the polymer according to claim 4.

46. A coating composition containing the polymer according to claim 4.

47. A molded product formed by molding the composition containing the polymer according to claim 4.

48. A molded product obtained by coating or printing on a molded product formed by molding a composition containing the polymer according to claim 4.

49. A cosmetic material containing the polymer according to claim 4.

50. A releasing agent for toner containing the polymer according to claim 4.

51. A pigment dispersant containing the polymer according to claim 4.

52. A lubricant for vinyl chloride resins, containing the polymer according to claim 4.

53. An emulsion composition containing the polymer according to claim 4.

54. An oxygen trapping composition containing the polymer according to claim 4.

55. A resin composition comprising the polymer according to claim 5 and at least one material selected from the group consisting of salts of alkali metals or alkaline earth metals, surfactants, compatibilizing agents and polymer antistatic agents other than a polymer having a structural unit represented by the following Formula (2):

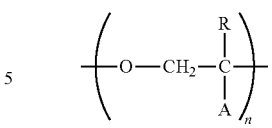

(2)

wherein A is a polymer of an olefin having 2 to 20 carbon atoms, the polymer having a. weight average molecular weight of 400 to 500,000; R is a hydrogen atom, or an alkyl group or aralkyl group having 1 to 18 carbon atoms; and n is an integer of 1 or greater.

56. A resin composition comprising the polymer according to claim 5 and other thermoplastic resin.

57. A resin composition containing the polymer according to claim 5 and other thermoplastic resin, and further at least one material selected from the group consisting of salts of alkali metals or alkaline earth metals, surfactants, compatibilizing agents and polymer antistatic agents other than a polymer having a structural unit represented by the following Formula (2):

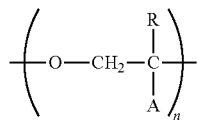 (2)

wherein A is a polymer of an olefin having 2 to 20 carbon atoms, the polymer having a weight average molecular weight of 400 to 500,000; R is a hydrogen atom, or an alkyl group or aralkyl group having 1 to 18 carbon atoms; and n is an integer of 1 or greater.

58. An antistatic agent containing the polymer according to claim 5.

59. An adhesive containing the polymer according to claim 5.

60. A coating composition containing the polymer according to claim 5.

61. A molded product formed by molding the composition containing the polymer according to claim 5.

62. A molded product obtained by coating or printing on a molded product formed by molding a composition containing the polymer according to claim 5.

63. A cosmetic material containing the polymer according to claim 5.

64. A releasing agent for toner containing the polymer according to claim 5.

65. A pigment dispersant containing the polymer according to claim 5.

66. A lubricant for vinyl chloride resins, containing the polymer according to claim 5.

67. An emulsion composition containing the polymer according to claim 5.

68. An oxygen trapping composition containing the polymer according to claim 5.

* * * * *